US008283445B2

(12) United States Patent
Reed

(10) Patent No.: US 8,283,445 B2
(45) Date of Patent: Oct. 9, 2012

(54) EXTRACELLULAR-SIGNAL-REGULATED-KINASE (ERK) HETEROPOLYLIGAND POLYPEPTIDE

(75) Inventor: Thomas David Reed, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 769 days.

(21) Appl. No.: 11/983,235

(22) Filed: Nov. 8, 2007

(65) Prior Publication Data

US 2009/0186379 A1 Jul. 23, 2009

Related U.S. Application Data

(60) Provisional application No. 60/865,589, filed on Nov. 13, 2006.

(51) Int. Cl.
*C07K 14/00* (2006.01)
*A61K 38/00* (2006.01)
*A61K 38/16* (2006.01)

(52) U.S. Cl. .................. 530/350; 514/1.1; 514/21.3

(58) Field of Classification Search .................. None
See application file for complete search history.

(56) References Cited

U.S. PATENT DOCUMENTS

| 7,071,295 | B2 | 7/2006 | Reed |
| 2004/0185556 | A1 | 9/2004 | Reed |
| 2008/0032947 | A1 | 2/2008 | Reed |
| 2008/0050808 | A1 | 2/2008 | Reed et al. |
| 2008/0051360 | A1 | 2/2008 | Reed et al. |
| 2008/0213834 | A1 | 9/2008 | Reed et al. |
| 2008/0220475 | A1 | 9/2008 | Reed et al. |
| 2009/0186379 | A1 | 7/2009 | Reed |
| 2009/0215173 | A1 | 8/2009 | Reed |
| 2009/0215866 | A1 | 8/2009 | Reed |

FOREIGN PATENT DOCUMENTS

| WO | WO 2005/040336 | 5/2005 |
| WO | WO2005116231 | 12/2005 |
| WO | WO 2007/048103 A2 | 4/2007 |
| WO | WO 2007/076166 A2 | 7/2007 |
| WO | WO 2008/119058 A2 | 10/2008 |

OTHER PUBLICATIONS

Chopra et al., J. Biol. Chem. 278:9402-9406, 2003.*
Lawrence, D.S., Handbook of Experimental Pharmacology 167:11-44, 2005.*
Molina et al., J. Biol. Chem. 280:42051-42060, 2005.*
Izumi et al., Circulation Res. 88:1120-1126, 2001.*
Nichols et al., J. Biol. Chem. 275:24613-24621, 2000.*
Adams, et al. 2000 The A-type potassium channel Kv4.2 is a substrate for the mitogen-activated protein kinase ERK J Neurochem 75:2277-87.
Arnaud, et al. 2004 Phosphorylation of Grb2-associated binder 2 on serine 623 by ERK MAPK regulates its association with the phosphatase SHP-2 and decreases STAT5 activation J Immunol 173:3962-71.
Chung, et al. 1997 STAT3 serine phosphorylation by ERK-dependent and -independent pathways negatively modulates its tyrosine phosphorylation Mol Cell Biol 17:6508-16.
Clark-Lewis, et al. 1991 Definition of a consensus sequence for peptide substrate recognition by p44mpk, the meiosis-activated myelin basic protein kinase J Biol Chem 266:15180-4.
Eymin, et al. 2006 p14ARF triggers G2 arrest through ERK-mediated Cdc25C phosphorylation, ubiquitination and proteasomal degradation Cell Cycle 5:759-65.
Fantz, et al. 2001 Docking sites on substrate proteins direct extracellular signal-regulated kinase to phosphorylate specific residues J Biol Chem 276:27256-65.
Garcia, et al. 2002 IEX-1: a new ERK substrate involved in both ERK survival activity and ERK activation Embo J 21:5151-63.
Gille, et al. 1995 ERK phosphorylation potentiates Elk-1-mediated ternary complex formation and transactivation Embo J 14:951-62.
Haycock, et al. 1992 ERK1 and ERK2, two microtubule-associated protein 2 kinases, mediate the phosphorylation of tyrosine hydroxylase at serine-31 in situ Proc Natl Acad Sci U S A 89:2365-9.
Hedges, et al. 2000 Phosphorylation of caldesmon by ERK MAP kinases in smooth muscle Am J Physiol Cell Physiol 278:C718-26.
Hindley, et al. 2002 Extracellular signal regulated kinase (ERK)/mitogen activated protein kinase (MAPK)—independent functions of Raf kinases J Cell Sci 115:1575-81.
Howell, et al. 1991 STY, a tyrosine-phosphorylating enzyme with sequence homology to serine/threonine kinases Mol Cell Biol 11:568-72.
Ishibe, et al. 2004 Paxillin serves as an ERK-regulated scaffold for coordinating FAK and Rac activation in epithelial morphogenesis Mol Cell 16:257-67.
Jacobs, et al. 1999 Multiple docking sites on substrate proteins form a modular system that mediates recognition by ERK MAP kinase Genes Dev 13:163-75.
Jacque, et al. 1998 Modulation of HIV-1 infectivity by MAPK, a virion-associated kinase Embo J 17:2607-18.
Ji et al. 2003 Targeted inhibition of Ca2+/calmodulin-dependent protein kinase II in cardiac longitudinal sarcoplasmic reticulum results in decreased phospholamban phosphorylation at threonine 17 J Biol Chem 278:25063-71.
Kelemen, et al. 2002 Selective in vivo inhibition of mitogen-activated protein kinase activation using cell-permeable peptides J Biol Chem 277:8741-8.
Kolch 2000 Meaningful relationships: the regulation of the Ras/Raf/MEK/ERK pathway by protein interactions Biochem J 351 Pt 2:289-305.
Lefebvre, et al. 2002 Meiotic spindle stability depends on MAPK-interacting and spindle-stabilizing protein (MISS), a new MAPK substrate J Cell Biol 157:603-13.
Lin, et al. 1999 Feedback regulation of beta-arrestin1 function by extracellular signal-regulated kinases J Biol Chem 274:15971-4.

(Continued)

*Primary Examiner* — David J Steadman
(74) *Attorney, Agent, or Firm* — Sterne, Kessler, Goldstein & Fox, P.L.L.C.

(57) ABSTRACT

The invention relates to kinase inhibitor ligands and polyligands. In particular, the invention relates to ligands and polyligands that modulate ERK activity. The ligands and polyligands are utilized as research tools or as therapeutics. The invention includes linkage of the ligands and polyligands to a cellular localization signal, epitope tag and/or a reporter. The invention also includes polynucleotides encoding the ligands and polyligands.

10 Claims, 21 Drawing Sheets

(3 of 21 Drawing Sheet(s) Filed in Color)

OTHER PUBLICATIONS

Matallanas, et al. 2006 Distinct utilization of effectors and biological outcomes resulting from site-specific Ras activation: Ras functions in lipid rafts and Golgi complex are dispensable for proliferation and transformation Mol Cell Biol 26:100-16.

Matsuura, et al. 2005 Identification and characterization of ERK MAP kinase phosphorylation sites in Smad3 Biochemistry 44:12546-53.

Matter, et al. 2002 Signal-dependent regulation of splicing via phosphorylation of Sam68 Nature 420:691-5.

Missero, et al. 2000 Multiple ras downstream pathways mediate functional repression of the homeobox gene product TTF-1 Mol Cell Biol 20:2783-93.

Morton, et al. 2004 Signalling pathways involved in multisite phosphorylation of the transcription factor ATF-2 FEBS Lett 572:177-83.

Oliveira S, Storm G, Schiffelers RM. (2006). Targeted delivery of siRNA. Journal of Biomedicine and Biotechnology 2006, 1-9.

Pandey, et al. 2005 Activation of TRAP/mediator subunit TRAP220/Med1 is regulated by mitogen-activated protein kinase-dependent phosphorylation Mol Cell Biol 25:10695-710.

Rowinsky, EK. (2003). Challenges of developing therapeutics that target signal transduction in patients with gynecologic and other malignancies. Journal of Clinical Oncology 21, 175s-186s.

Sanghera, et al. 1990 Identification of the sites in myelin basic protein that are phosphorylated by meiosis-activated protein kinase p44mpk FEBS Lett 273:223-6.

Schaeffer, et al. 1999 Mitogen-activated protein kinases: specific messages from ubiquitous messengers Mol Cell Biol 19:2435-44.

Songyang, et al. 1996 A structural basis for substrate specificities of protein Ser/Thr kinases: primary sequence preference of casein kinases I and II, NIMA, phosphorylase kinase, calmodulin-dependent kinase II, CDK5, and Erk1 Mol Cell Biol 16:6486-93.

Soond, et al. 2005 ERK-mediated phosphorylation of Thr735 in TNFalpha-converting enzyme and its potential role in TACE protein trafficking J Cell Sci 118:2371-80.

Terret, et al. 2003 DOC1R: a MAP kinase substrate that control microtubule organization of metaphase II mouse oocytes Development 130:5169-77.

Vantaggiato et al. 2006 ERK1 and ERK2 mitogen-activated protein kinases affect Ras-dependent cell signaling differentially. J. of Biol. 5:14.

Veeranna, et al. 1998 Mitogen-activated protein kinases (Erk1,2) phosphorylate Lys-Ser-Pro (KSP) repeats in neurofilament proteins NF-H and NF-M J Neurosci 18:4008-21.

Xu, et al. 2001 Phosphorylation of nuclear phospholipase C beta1 by extracellular signal-regulated kinase mediates the mitogenic action of insulin-like growth factor I Mol Cell Biol 21:2981-90.

Zhang, et al. 2001 UVA induces Ser381 phosphorylation of p90RSK/MAPKAP-K1 via ERK and JNK pathways J Biol Chem 276:14572-80.

U.S. Appl. No. 12/090,462, inventor Reed, Thomas D., filed Oct. 18, 2006.

U.S. Appl. No. 12/532,912, inventors Bachinsky et al., U.S. national phase of International Application No. PCT/US08/058531, filed Mar. 27, 2008.

* cited by examiner

| LIGAND X | LIGAND X |

FIGURE 1A

| LIGAND X | LIGAND X | LIGAND X |

FIGURE 1B

| LIGAND X | LIGAND X | LIGAND X | LIGAND X | LIGAND X |

FIGURE 1C

| LIGAND X | SPACER | LIGAND X |

FIGURE 2A

| LIGAND X | SPACER | LIGAND X | SPACER | LIGAND X |

FIGURE 2B

| LIGAND X | LIGAND X | SPACER | LIGAND X | SPACER | LIGAND X |

FIGURE 2C

| LIGAND X | LIGAND Y |

FIGURE 3A

| LIGAND X | LIGAND Y | LIGAND Z |

FIGURE 3B

| LIGAND X | LIGAND Y | LIGAND X | LIGAND Z | LIGAND A |

FIGURE 3C

| LIGAND A | LIGAND B | LIGAND C | LIGAND D |

FIGURE 3D

| LIGAND A | LIGAND A | LIGAND B | LIGAND C |

FIGURE 3E

| LIGAND B | SPACER | LIGAND A |

FIGURE 4A

| LIGAND Z | SPACER | LIGAND Y | SPACER | LIGAND X |

FIGURE 4B

| LIGAND X | LIGAND Y | SPACER | LIGAND Y | LIGAND X |

FIGURE 4C

| LIGAND A | SPACER | LIGAND B | SPACER | LIGAND C | SPACER | LIGAND D | SPACER | LIGAND E | SPACER | LIGAND F |

FIGURE 4D

| LIGAND X | LIGAND Y | S | LIGAND Z | S | LIGAND A | S | LIGAND B | S | LIGAND C | S | LIGAND D | S | LIGAND E | S | LIGAND F |

FIGURE 4E

| LIGAND C | SPACER | LIGAND Y | SPACER | LIGAND Z | SPACER | LIGAND Y |

FIGURE 4F

| LIGAND X | LIGAND X | LOCALIZATION SIGNAL |

FIGURE 7A

| LOCALIZATION SIGNAL | LIGAND X | LIGAND Y |

FIGURE 7B

| LIGAND X | SPACER | LIGAND X | LOCALIZATION SIGNAL |

FIGURE 7C

| LOCALIZATION SIGNAL | LIGAND X | SPACER | LIGAND Y |

FIGURE 7D

| LIGAND X | SPACER | LIGAND Y | LIGAND B | LOCALIZATION SIGNAL |

FIGURE 7E

| LOCALIZATION SIGNAL | LIGAND A | LIGAND B | LIGAND C | LIGAND D |

FIGURE 7F

| LOCALIZATION SIGNAL | LIGAND Y |

FIGURE 7G

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

FIGURE 8F

| EPITOPE | LIGAND B | LOCALIZATION SIGNAL |

FIGURE 8G

| PROMOTER | LIGAND or POLYLIGAND | EPITOPE | LOCALIZATION SIGNAL | STOP | POLY-A |

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 9B

| PROMOTER | LIGAND or POLYLIGAND | REPORTER | LOCALIZATION SIGNAL | STOP | POLY-A |

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND or POLYLIGAND | LOCALIZATION SIGNAL | STOP | POLY-A |

FIGURE 9E

| PROMOTER | LOCALIZATION SIGNAL | LIGAND or POLYLIGAND | STOP | POLY-A |

FIGURE 9F

| PROMOTER | LIGAND or POLYLIGAND | STOP | POLY-A |

SEQUENCE LISTING

```
<160> NUMBER OF SEQ ID NOS: 115

<210> SEQ ID NO 1
<211> LENGTH: 91
<212> TYPE: PRT
<213> ORGANISM: Artificial Sequence
<220> FEATURE:
<223> OTHER INFORMATION: Synthetic polyligand

<400> SEQUENCE: 1

Met Pro Lys Lys Lys Pro Thr Pro Ile Gln Leu Asn Pro Ala Ala Lys
 1               5                  10                  15
```

```
Gly Arg Lys Pro Arg Asp Leu Glu Leu Pro Ala Ala Ala Thr Gly
            20                  25                  30

Pro Leu Ala Pro Gly Pro Phe Gly Ala Gly Ala Tyr Ser Pro Thr Ala
        35                  40                  45

Pro Thr Tyr Ser Pro Thr Ala Pro Lys Lys Gly Gly Gly Ala
50                  55                  60

Pro Arg Ala Pro Gly Gly Arg Ala Gly Ala Gly Arg Arg Pro Arg
65                  70                  75                  80

Ala Pro Ala Lys Leu Ser Phe Phe Phe Pro Ser
                85                  90

<210> SEQ ID NO 2
<211> LENGTH: 273
<212> TYPE: DNA
<213> ORGANISM: Artificial Sequence
<220> FEATURE:
<223> OTHER INFORMATION: Synthetic polyligand

<400> SEQUENCE: 2
atgcccaaga agaagcccac ccccatccag ctgaaccccg ccgccaaggg caggaagcct      60
agggacctgg agctgccccgc cgccgccgcc accggccccc tggccccccgg ccccttcggc     120 gctggagcct acagccccac cgcccccacc tacagcccca ccgcccccaa gaagaagggc     180
ggcggcggcg cccccagggc cccggccggc aggagggctg cgccggaag gaggcccagg     240 gcccccgcca agctgagctt cttcttcccc agc                                  273

<210> SEQ ID NO 3
<211> LENGTH: 300
<212> TYPE: DNA
<213> ORGANISM: Artificial Sequence
<220> FEATURE:
<223> OTHER INFORMATION: Synthetic polyligand

<400> SEQUENCE: 3
gccggcatgc ccaagaagaa gcccaccccc atccagctga ccccgccgc caagggcagg      60 aagcctaggg acctggagct gccccgccgcc gccgccaccg gcccctggc cccggcccc     120 ttcggcgctg gagcctacag ccccaccgcc cccacctaca gccccaccgc cccaagaag     180 aagggcggcg gcggcccccc cagggccccc ggcggcagga gggctggcgc cggaaggagg     240
cccagggccc ccgccaagct gagcttcttc ttccccagcc ccggggggcgg aggcatcgat     300

<210> SEQ ID NO 4
<211> LENGTH: 306
<212> TYPE: DNA
<213> ORGANISM: Artificial Sequence
<220> FEATURE:
<223> OTHER INFORMATION: Synthetic polyligand

<400> SEQUENCE: 4
gctagcgcca ccatgcctaa gaagaagccc actccgattc aactgaaccc agcagctaag      60 ggggaggaaac caagagacct tgaactccca gcagccgcag ccacgggggcc gctggcccca     120 ggcccgttcg gtgcaggtgc atacagtcca accgcaccta ctactctcc taccgcacct     180 aaaaagaagg gcggcggggg agcgcctcgc gcccccggag gtagacgagc tggggcaggt     240
cgcaggccca gagcaccagc caagctctcc ttcttttttc aagcccccgg gggcggtggc     300
atcgat                                                                306

<210> SEQ ID NO 5
<211> LENGTH: 171
```

```
<212> TYPE: PRT
<213> ORGANISM: Artificial Sequence
<220> FEATURE:
<223> OTHER INFORMATION: Synthetic polyligand

<400> SEQUENCE: 5

Pro Pro Leu Met Ala Pro Pro Phe Tyr Pro Gln Lys Gly Arg Lys Pro
1               5                   10                  15

Arg Asp Leu Glu Leu Pro Leu Ala Ala Ala Lys Gln Ala Glu Ala
            20                  25                  30

Val Thr Ala Pro Arg Gly Ala Gly Ala Lys Asn Ile Val Thr Pro Arg
                35                  40                  45

Ala Pro Pro Ser Gln Gly Lys Gly Gly Gly Thr Leu Ser Pro
        50                  55                  60

Ile Ala Pro Arg Ala Pro Ala Lys Leu Ser Phe Gln Phe Pro Ser Ser
65                  70                  75                  80

Ala Gly Pro Gly Ala Glu Phe Leu Lys Pro Ile Glu Ser Ser Ile Leu
                85                  90                  95

Ala Gln Arg Arg Val Arg Lys Leu Pro Ser Thr Ala Gly Ala Gly Lys
            100                 105                 110

Arg Glu Leu Val Glu Pro Leu Ala Pro Ser Gly Glu Ala Pro Asn Gln
            115                 120                 125

Ala Leu Leu Arg Ala Ala Gly Gly Tyr Ser Pro Thr Ala Pro Thr Tyr
        130                 135                 140

Ser Pro Thr Ala Pro Lys Lys Lys Gly Gly Ala Ala Thr Pro Thr Ala
145                 150                 155                 160

Ala His Ser Gly Ser His Leu Phe Gly Phe Pro
                165                 170

<210> SEQ ID NO 6
<211> LENGTH: 513
<212> TYPE: DNA
<213> ORGANISM: Artificial Sequence
<220> FEATURE:
<223> OTHER INFORMATION: Synthetic polyligand

<400> SEQUENCE: 6 cccccctga tggcccccc cttctacccc cagaagggca ggaagcctag ggacctggag      60
ctgcccctgg ccgccgccgc caagcaggcc gaggccgtga ccgcccccag ggcgctggc   120 gccaagaaca tcgtgacccc cagggccccc cccccagcc agggcaaggg cggcggcggc   180
accctgagcc ccatcgcccc cagggccccc gccaagctga gcttccagtt ccccagcagc   240
gctggccccg gcgccgagtt cctgaagccc atcgagagca gcatcctggc ccagaggagg   300
gtgaggaagc tgcccagcac cgctggcgct ggcaagaggg agctggtgga ccccctggcc   360
cccagcggcg aggcccccaa ccaggccctg ctgagggccg ctggcggcta cagccccacc   420
gcccccacct acagccccac cgcccccaag aagaagggcg gcgccgccac ccccaccgcc   480
gcccacagcg gcagccacct gttcggcttc ccc                                513

<210> SEQ ID NO 7
<211> LENGTH: 540
<212> TYPE: DNA
<213> ORGANISM: Artificial Sequence
<220> FEATURE:
<223> OTHER INFORMATION: Synthetic polyligand

<400> SEQUENCE: 7
gccggccccc ccctgatggc ccccccttc taccccaga agggcaggaa gcctagggac      60
```

```
ctggagctgc ccctggccgc cgccgccaag caggccgagg ccgtgaccgc ccccaggggc    120
gctggcgcca agaacatcgt gaccccccag gccccccccc ccagccaggg caagggcggc    180
ggcggcaccc tgagccccat cgccccccagg gccccgcca agctgagctt ccagttcccc    240
agcagcgctg gccccggcgc cgagttcctg aagcccatcg agagcagcat cctggcccag    300
aggagggtga ggaagctgcc cagcaccgct ggcgctggca gagggagct ggtggagccc    360 ctggccccca gcggcgaggc ccccaaccag gccctgctga gggccgctgg cggctacagc    420
cccaccgccc ccacctacag ccccaccgcc cccaagaaga agggcggcgc cgccaccccc    480
accgccgccc acagcggcag ccacctgttc ggcttccccc cggggggcgg aggcatcgat    540
```

<210> SEQ ID NO 8
<211> LENGTH: 540
<212> TYPE: DNA
<213> ORGANISM: Artificial Sequence
<220> FEATURE:
<223> OTHER INFORMATION: Synthetic polyligand
<400> SEQUENCE: 8

```
gctagccccc ctttgatggc tccgccgttc taccctcaga agggtcggaa accaagggat     60
ctcgaactgc ccctcgctgc cgccgcaaag caggccgaag ctgtgaccgc acctagaggg    120
gcgggtgcga agaacatagt aactccacgg gcacctccgc catcccaggg gaagggcggt    180
ggcgggacgc tgagtccaat cgccccgagg gctcctgcca agttgagttt ccagttcccg    240
tcaagcgccg ggcctggagc tgagtttctc aagcccatag agtccagtat cctcgctcaa    300
cgacgggtga gaaaactgcc ctccacggca ggggcaggta agagagaact ggttgagcct    360
ctggccccta gcggcgaagc gccgaaccaa gcattgcttc gcgctgccgg ggggtattca    420
cccacagcgc ctaccttattc tcccacagcc cctaagaaga agggcggagc ggctacacct    480
acggccgctc atagcggatc tcacctgttt gggtttcccc ccggggagg cggaatcgat    540
```

<210> SEQ ID NO 9
<211> LENGTH: 418
<212> TYPE: PRT
<213> ORGANISM: Homo sapiens
<220> FEATURE:
<221> NAME/KEY: misc_feature
<222> LOCATION: (412)..(412)
<223> OTHER INFORMATION: Xaa can be any naturally occurring amino acid
<400> SEQUENCE: 9

```
Met Gly Asp Lys Gly Thr Arg Val Phe Lys Lys Ala Ser Pro Asn Gly
1               5                   10                  15

Lys Leu Thr Val Tyr Leu Gly Lys Arg Asp Phe Val Asp His Ile Asp
            20                  25                  30

Leu Val Asp Pro Val Asp Gly Val Val Leu Val Asp Pro Glu Tyr Leu
        35                  40                  45

Lys Glu Arg Arg Val Tyr Val Thr Leu Thr Cys Ala Phe Arg Tyr Gly
    50                  55                  60

Arg Glu Asp Leu Asp Val Leu Gly Leu Thr Phe Arg Lys Asp Leu Phe
65                  70                  75                  80

Val Ala Asn Val Gln Ser Phe Pro Pro Ala Pro Glu Asp Lys Lys Pro
                85                  90                  95

Leu Thr Arg Leu Gln Glu Arg Leu Ile Lys Lys Leu Gly Glu His Ala
            100                 105                 110

Tyr Pro Phe Thr Phe Glu Ile Pro Pro Asn Leu Pro Cys Ser Val Thr
        115                 120                 125
```

-continued

Leu Gln Pro Gly Pro Glu Asp Thr Gly Lys Ala Cys Gly Val Asp Tyr
            130                 135                 140

Glu Val Lys Ala Phe Cys Ala Glu Asn Leu Glu Lys Ile His Lys
145                 150                 155                 160

Arg Asn Ser Val Arg Leu Val Ile Arg Lys Val Gln Tyr Ala Pro Glu
                165                 170                 175

Arg Pro Gly Pro Gln Pro Thr Ala Glu Thr Thr Arg Gln Phe Leu Met
            180                 185                 190

Ser Asp Lys Pro Leu His Leu Glu Ala Ser Leu Asp Lys Glu Ile Tyr
            195                 200                 205

Tyr His Gly Glu Pro Ile Ser Val Asn Val His Val Thr Asn Asn Thr
            210                 215                 220

Asn Lys Thr Val Lys Lys Ile Lys Ile Ser Val Arg Gln Tyr Ala Asp
225                 230                 235                 240

Ile Cys Leu Phe Asn Thr Ala Gln Tyr Lys Cys Pro Val Ala Met Glu
                245                 250                 255

Glu Ala Asp Asp Thr Val Ala Pro Ser Ser Thr Phe Cys Lys Val Tyr
            260                 265                 270

Thr Leu Thr Pro Phe Leu Ala Asn Asn Arg Glu Lys Arg Gly Leu Ala
            275                 280                 285

Leu Asp Gly Lys Leu Lys His Glu Asp Thr Asn Leu Ala Ser Ser Thr
290                 295                 300

Leu Leu Arg Glu Gly Ala Asn Arg Glu Ile Leu Gly Ile Ile Val Ser
305                 310                 315                 320

Tyr Lys Val Lys Val Lys Leu Val Val Ser Arg Gly Gly Leu Leu Gly
                325                 330                 335

Asp Leu Ala Ser Ser Asp Val Ala Val Glu Leu Pro Phe Thr Leu Met
            340                 345                 350

His Pro Lys Pro Lys Glu Glu Pro Pro His Arg Glu Val Pro Glu Asn
            355                 360                 365

Glu Thr Pro Val Asp Thr Asn Leu Ile Glu Leu Asp Thr Asn Asp Asp
            370                 375                 380

Asp Ile Val Phe Glu Asp Phe Ala Arg Gln Arg Leu Lys Gly Met Lys
385                 390                 395                 400

Asp Asp Lys Glu Glu Glu Glu Asp Gly Thr Gly Xaa Pro Gln Leu Asn
                405                 410                 415

Asn Arg

<210> SEQ ID NO 10
<211> LENGTH: 505
<212> TYPE: PRT
<213> ORGANISM: Homo sapiens
<220> FEATURE:
<221> NAME/KEY: misc_feature
<222> LOCATION: (90)..(90)
<223> OTHER INFORMATION: Xaa can be any naturally occurring amino acid

<400> SEQUENCE: 10

Met Lys Phe Lys Leu His Val Asn Ser Ala Arg Gln Tyr Lys Asp Leu
1               5                   10                  15

Trp Asn Met Ser Asp Asp Lys Pro Phe Leu Cys Thr Ala Pro Gly Cys
                20                  25                  30

Gly Gln Arg Phe Thr Asn Glu Asp His Leu Ala Val His Lys His Lys
            35                  40                  45

His Glu Met Thr Leu Lys Phe Gly Pro Ala Arg Asn Asp Ser Val Ile
50                  55                  60

```
Val Ala Asp Gln Thr Pro Thr Pro Thr Arg Phe Leu Lys Asn Cys Glu
 65                  70                  75                  80

Glu Val Gly Leu Phe Asn Glu Leu Ala Xaa Pro Phe Glu Asn Glu Phe
                 85                  90                  95

Lys Lys Ala Ser Glu Asp Ile Lys Lys Met Pro Leu Asp Leu Ser
            100                 105                 110

Pro Leu Ala Thr Pro Ile Ile Arg Ser Lys Ile Glu Glu Pro Ser Val
        115                 120                 125

Val Glu Thr Thr His Gln Asp Ser Pro Leu Pro His Pro Glu Ser Thr
    130                 135                 140

Thr Ser Asp Glu Lys Glu Val Pro Leu Ala Gln Thr Ala Gln Pro Thr
145                 150                 155                 160

Ser Ala Ile Val Arg Pro Ala Ser Leu Gln Val Pro Asn Val Leu Leu
                165                 170                 175

Thr Ser Ser Asp Ser Ser Val Ile Ile Gln Gln Ala Val Pro Ser Pro
            180                 185                 190

Thr Ser Ser Thr Val Ile Thr Gln Ala Pro Ser Ser Asn Arg Pro Ile
        195                 200                 205

Val Pro Val Pro Gly Pro Phe Pro Leu Leu His Leu Pro Asn Gly
    210                 215                 220

Gln Thr Met Pro Val Ala Ile Pro Ala Ser Ile Thr Ser Ser Asn Val
225                 230                 235                 240

His Val Pro Ala Ala Val Pro Leu Val Arg Pro Val Thr Met Val Pro
                245                 250                 255

Ser Val Pro Gly Ile Pro Gly Pro Ser Ser Pro Gln Pro Val Gln Ser
            260                 265                 270

Glu Ala Lys Met Arg Leu Lys Ala Ala Leu Thr Gln Gln His Pro Pro
        275                 280                 285

Val Thr Asn Gly Asp Thr Val Lys Gly His Gly Ser Gly Leu Val Arg
    290                 295                 300

Thr Gln Ser Glu Glu Ser Arg Pro Gln Ser Leu Gln Gln Pro Ala Thr
305                 310                 315                 320

Ser Thr Thr Glu Thr Pro Ala Ser Pro Ala His Thr Thr Pro Gln Thr
                325                 330                 335

Gln Ser Thr Ser Gly Arg Arg Arg Ala Ala Asn Glu Asp Pro Asp
            340                 345                 350

Glu Lys Arg Arg Lys Phe Leu Glu Arg Asn Arg Ala Ala Ala Ser Arg
        355                 360                 365

Cys Arg Gln Lys Arg Lys Val Trp Val Gln Ser Leu Glu Lys Lys Ala
    370                 375                 380

Glu Asp Leu Ser Ser Leu Asn Gly Gln Leu Gln Ser Glu Val Thr Leu
385                 390                 395                 400

Leu Arg Asn Glu Val Ala Gln Leu Lys Gln Leu Leu Leu Ala His Lys
                405                 410                 415

Asp Cys Pro Val Thr Ala Met Gln Lys Lys Ser Gly Tyr His Thr Ala
            420                 425                 430

Asp Lys Asp Asp Ser Ser Glu Asp Ile Ser Val Pro Ser Ser Pro His
        435                 440                 445

Thr Glu Ala Ile Gln His Ser Ser Val Ser Thr Ser Asn Gly Val Ser
    450                 455                 460

Ser Thr Ser Lys Ala Glu Ala Val Ala Thr Ser Val Leu Thr Gln Met
465                 470                 475                 480

Ala Asp Gln Ser Thr Glu Pro Ala Leu Ser Gln Ile Val Met Ala Pro
                485                 490                 495
```

```
Ser Ser Gln Ser Gln Pro Ser Gly Ser
        500                 505

<210> SEQ ID NO 11
<211> LENGTH: 793
<212> TYPE: PRT
<213> ORGANISM: Homo sapiens
<220> FEATURE:
<221> NAME/KEY: misc_feature
<222> LOCATION: (789)..(789)
<223> OTHER INFORMATION: Xaa can be any naturally occurring amino acid

<400> SEQUENCE: 11

Met Asp Asp Phe Glu Arg Arg Glu Leu Arg Arg Gln Lys Arg Glu
1               5                   10                  15

Glu Met Arg Leu Glu Ala Glu Arg Ile Ala Tyr Gln Arg Asn Asp Asp
            20                  25                  30

Asp Glu Glu Glu Ala Ala Arg Glu Arg Arg Arg Ala Arg Gln Glu
        35                  40                  45

Arg Leu Arg Gln Lys Gln Glu Glu Ser Leu Gly Gln Val Thr Asp
    50                  55                  60

Gln Val Glu Val Asn Ala Gln Asn Ser Val Pro Asp Glu Glu Ala Lys
65                  70                  75                  80

Thr Thr Thr Thr Asn Thr Gln Val Glu Gly Asp Asp Glu Ala Ala Phe
                85                  90                  95

Leu Glu Arg Leu Ala Arg Arg Glu Glu Arg Arg Gln Lys Arg Leu Gln
            100                 105                 110

Glu Ala Leu Glu Arg Gln Lys Glu Phe Asp Pro Thr Ile Thr Asp Ala
        115                 120                 125

Ser Leu Ser Leu Pro Ser Arg Arg Met Gln Asn Asp Thr Ala Glu Asn
    130                 135                 140

Glu Thr Thr Glu Lys Glu Glu Lys Ser Glu Ser Arg Gln Glu Arg Tyr
145                 150                 155                 160

Glu Ile Glu Glu Thr Glu Thr Val Thr Lys Ser Tyr Gln Lys Asn Asp
                165                 170                 175

Trp Arg Asp Ala Glu Glu Asn Lys Lys Glu Asp Lys Glu Lys Glu Glu
            180                 185                 190

Glu Glu Glu Glu Lys Pro Lys Arg Gly Ser Ile Gly Glu Asn Gln Val
        195                 200                 205

Glu Val Met Val Glu Glu Lys Thr Thr Glu Ser Gln Glu Glu Thr Val
    210                 215                 220

Val Met Ser Leu Lys Asn Gly Gln Ile Ser Ser Glu Glu Pro Lys Gln
225                 230                 235                 240

Glu Glu Glu Arg Glu Gln Gly Ser Asp Glu Ile Ser His His Glu Lys
                245                 250                 255

Met Glu Glu Glu Asp Lys Glu Arg Ala Glu Ala Glu Arg Ala Arg Leu
            260                 265                 270

Glu Ala Glu Glu Arg Glu Arg Ile Lys Ala Glu Gln Asp Lys Lys Ile
        275                 280                 285

Ala Asp Glu Arg Ala Arg Ile Glu Ala Glu Lys Ala Ala Ala Gln
    290                 295                 300

Glu Arg Glu Arg Glu Ala Glu Glu Arg Glu Arg Met Arg Glu Glu
305                 310                 315                 320

Glu Lys Arg Ala Ala Glu Glu Arg Gln Arg Ile Lys Glu Glu Glu Lys
                325                 330                 335

Arg Ala Ala Glu Glu Arg Gln Arg Ile Lys Glu Glu Glu Lys Arg Ala
```

```
                340                 345                 350
Ala Glu Glu Arg Gln Arg Ile Lys Glu Glu Lys Arg Ala Ala Glu
                355                 360                 365

Glu Arg Gln Arg Ala Arg Ala Glu Glu Glu Lys Ala Lys Val Glu
        370                 375                 380

Glu Gln Lys Arg Asn Lys Gln Leu Glu Glu Lys His Ala Met Gln
385                 390                 395                 400

Glu Thr Lys Ile Lys Gly Glu Lys Val Glu Gln Lys Ile Glu Gly Lys
                405                 410                 415

Trp Val Asn Glu Lys Lys Ala Gln Glu Asp Lys Leu Gln Thr Ala Val
                420                 425                 430

Leu Lys Lys Gln Gly Glu Glu Lys Gly Thr Lys Val Gln Ala Lys Arg
        435                 440                 445

Glu Lys Leu Gln Glu Asp Lys Pro Thr Phe Lys Lys Glu Ile Lys
        450                 455                 460

Asp Glu Lys Ile Lys Lys Asp Lys Glu Pro Lys Glu Glu Val Lys Ser
465                 470                 475                 480

Phe Met Asp Arg Lys Lys Gly Phe Thr Glu Val Lys Ser Gln Asn Gly
                485                 490                 495

Glu Phe Met Thr His Lys Leu Lys His Thr Glu Asn Thr Phe Ser Arg
            500                 505                 510

Pro Gly Gly Arg Ala Ser Val Asp Thr Lys Glu Ala Glu Gly Ala Pro
        515                 520                 525

Gln Val Glu Ala Gly Lys Arg Leu Glu Glu Leu Arg Arg Arg Arg Gly
        530                 535                 540

Glu Thr Glu Ser Glu Glu Phe Glu Lys Leu Lys Gln Lys Gln Gln Glu
545                 550                 555                 560

Ala Ala Leu Glu Leu Glu Glu Leu Lys Lys Lys Arg Glu Glu Arg Arg
                565                 570                 575

Lys Val Leu Glu Glu Glu Glu Gln Arg Arg Lys Gln Glu Glu Ala Asp
                580                 585                 590

Arg Lys Leu Arg Glu Glu Glu Glu Lys Arg Arg Leu Lys Glu Glu Ile
                595                 600                 605

Glu Arg Arg Arg Ala Glu Ala Ala Glu Lys Arg Gln Lys Met Pro Glu
        610                 615                 620

Asp Gly Leu Ser Asp Asp Lys Lys Pro Phe Lys Cys Phe Thr Pro Lys
625                 630                 635                 640

Gly Ser Ser Leu Lys Ile Glu Glu Arg Ala Glu Phe Leu Asn Lys Ser
                645                 650                 655

Val Gln Lys Ser Ser Gly Val Lys Ser Thr His Gln Ala Ala Ile Val
                660                 665                 670

Ser Lys Ile Asp Ser Arg Leu Glu Gln Tyr Thr Ser Ala Ile Glu Gly
        675                 680                 685

Thr Lys Ser Ala Lys Pro Thr Lys Pro Ala Ala Ser Asp Leu Pro Val
        690                 695                 700

Pro Ala Glu Gly Val Arg Asn Ile Lys Ser Met Trp Glu Lys Gly Asn
705                 710                 715                 720

Val Phe Ser Ser Pro Thr Ala Ala Gly Thr Pro Asn Lys Glu Thr Ala
                725                 730                 735

Gly Leu Lys Val Gly Val Ser Ser Arg Ile Asn Glu Trp Leu Thr Lys
                740                 745                 750

Thr Pro Asp Gly Asn Lys Ser Pro Ala Pro Lys Pro Ser Asp Leu Arg
        755                 760                 765
```

```
Pro Gly Asp Val Ser Ser Lys Arg Asn Leu Trp Glu Lys Gln Ser Val
    770                 775                 780
Asp Lys Val Thr Xaa Pro Thr Lys Val
785                 790

<210> SEQ ID NO 12
<211> LENGTH: 473
<212> TYPE: PRT
<213> ORGANISM: Homo sapiens
<220> FEATURE:
<221> NAME/KEY: misc_feature
<222> LOCATION: (216)..(216)
<223> OTHER INFORMATION: Xaa can be any naturally occurring amino acid

<400> SEQUENCE: 12

Met Ser Thr Glu Leu Phe Ser Ser Thr Arg Glu Glu Gly Ser Ser Gly
1               5                   10                  15

Ser Gly Pro Ser Phe Arg Ser Asn Gln Arg Lys Met Leu Asn Leu Leu
                20                  25                  30

Leu Glu Arg Asp Thr Ser Phe Thr Val Cys Pro Asp Val Pro Arg Thr
            35                  40                  45

Pro Val Gly Lys Phe Leu Gly Asp Ser Ala Asn Leu Ser Ile Leu Ser
    50                  55                  60

Gly Gly Thr Pro Lys Cys Cys Leu Asp Leu Ser Asn Leu Ser Ser Gly
65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Ser Pro Ala Gln Leu Leu Cys
        115                 120                 125

Ser Thr Pro Asn Gly Leu Asp Arg Gly His Arg Lys Arg Asp Ala Met
130                 135                 140

Cys Ser Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Glu Ile Ser Asp
            180                 185                 190

Glu Leu Met Glu Phe Ser Leu Lys Asp Gln Glu Ala Lys Val Ser Arg
        195                 200                 205

Ser Gly Leu Tyr Arg Ser Pro Xaa Met Pro Glu Asn Leu Asn Arg Pro
210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
            260                 265                 270

Leu Glu Glu Asp Ser Asn Gln Gly His Leu Ile Gly Asp Phe Ser Lys
        275                 280                 285

Val Cys Ala Leu Pro Thr Val Ser Gly Lys His Gln Asp Leu Lys Tyr
290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                325                 330                 335
```

```
Leu Gly Gly His Ile Gln Gly Ala Leu Asn Leu Tyr Ser Gln Glu Glu
            340                 345                 350

Leu Phe Asn Phe Phe Leu Lys Lys Pro Ile Val Pro Leu Asp Thr Gln
        355                 360                 365

Lys Arg Ile Ile Ile Val Phe His Cys Glu Phe Ser Ser Glu Arg Gly
370                 375                 380

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
                405                 410                 415

Arg Asp Phe Phe Pro Glu Tyr Met Glu Leu Cys Glu Pro Gln Ser Tyr
                420                 425                 430

Cys Pro Met His His Gln Asp His Lys Thr Glu Leu Leu Arg Cys Arg
                435                 440                 445

Ser Gln Ser Lys Val Gln Glu Gly Glu Arg Gln Leu Arg Glu Gln Ile
        450                 455                 460

Ala Leu Leu Val Lys Asp Met Ser Pro
465                 470

<210> SEQ ID NO 13
<211> LENGTH: 126
<212> TYPE: PRT
<213> ORGANISM: Homo sapiens
<220> FEATURE:
<221> NAME/KEY: misc_feature
<222> LOCATION: (23)..(23)
<223> OTHER INFORMATION: Xaa can be any naturally occurring amino acid

<400> SEQUENCE: 13

Met Ser Tyr Lys Pro Ile Ala Pro Ala Pro Ser Ser Thr Pro Gly Ser
1               5                   10                  15

Ser Thr Pro Gly Pro Gly Xaa Pro Val Pro Thr Gly Ser Val Pro Ser
            20                  25                  30

Pro Ser Gly Ser Val Pro Gly Ala Gly Ala Pro Phe Arg Pro Leu Phe
        35                  40                  45

Asn Asp Phe Gly Pro Pro Ser Met Gly Tyr Val Gln Ala Met Lys Pro
50                  55                  60

Pro Gly Ala Gln Gly Ser Gln Ser Thr Tyr Thr Asp Leu Leu Ser Val
65                  70                  75                  80

Ile Glu Glu Met Gly Lys Glu Ile Arg Pro Thr Tyr Ala Gly Ser Lys
                85                  90                  95

Ser Ala Met Glu Arg Leu Lys Arg Gly Ile Ile His Ala Arg Ala Leu
            100                 105                 110

Val Arg Glu Cys Leu Ala Glu Thr Glu Arg Asn Ala Arg Thr
        115                 120                 125

<210> SEQ ID NO 14
<211> LENGTH: 428
<212> TYPE: PRT
<213> ORGANISM: Homo sapiens
<220> FEATURE:
<221> NAME/KEY: misc_feature
<222> LOCATION: (324)..(324)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (383)..(383)
```

-continued

<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid

<400> SEQUENCE: 14

Met Asp Pro Ser Val Thr Leu Trp Gln Phe Leu Leu Gln Leu Leu Arg
1               5                   10                  15

Glu Gln Gly Asn Gly His Ile Ile Ser Trp Thr Ser Arg Asp Gly Gly
            20                  25                  30

Glu Phe Lys Leu Val Asp Ala Glu Val Ala Arg Leu Trp Gly Leu
        35                  40                  45

Arg Lys Asn Lys Thr Asn Met Asn Tyr Asp Lys Leu Ser Arg Ala Leu
    50                  55                  60

Arg Tyr Tyr Tyr Asp Lys Asn Ile Ile Arg Lys Val Ser Gly Gln Lys
65                  70                  75                  80

Phe Val Tyr Lys Phe Val Ser Tyr Pro Glu Val Ala Gly Cys Ser Thr
                85                  90                  95

Glu Asp Cys Pro Pro Gln Pro Glu Val Ser Val Thr Ser Thr Met Pro
            100                 105                 110

Asn Val Ala Pro Ala Ala Ile His Ala Ala Pro Gly Asp Thr Val Ser
        115                 120                 125

Gly Lys Pro Gly Thr Pro Lys Gly Ala Gly Met Ala Gly Pro Gly Gly
130                 135                 140

Leu Ala Arg Ser Ser Arg Asn Glu Tyr Met Arg Ser Gly Leu Tyr Ser
145                 150                 155                 160

Thr Phe Thr Ile Gln Ser Leu Gln Pro Gln Pro Pro His Pro Arg
                165                 170                 175

Pro Ala Val Val Leu Pro Asn Ala Ala Pro Ala Gly Ala Ala Ala Pro
            180                 185                 190

Pro Ser Gly Ser Arg Ser Thr Ser Pro Ser Pro Leu Glu Ala Cys Leu
        195                 200                 205

Glu Ala Glu Glu Ala Gly Leu Pro Leu Gln Val Ile Leu Thr Pro Pro
210                 215                 220

Glu Ala Pro Asn Leu Lys Ser Glu Glu Leu Asn Val Glu Pro Gly Leu
225                 230                 235                 240

Gly Arg Ala Leu Pro Pro Glu Val Lys Val Glu Gly Pro Lys Glu Glu
                245                 250                 255

Leu Glu Val Ala Gly Glu Arg Gly Phe Val Pro Glu Thr Thr Lys Ala
            260                 265                 270

Glu Pro Glu Val Pro Pro Gln Glu Gly Val Pro Ala Arg Leu Pro Ala
        275                 280                 285

Val Val Met Asp Thr Ala Gly Gln Ala Gly Gly His Ala Ala Ser Ser
290                 295                 300

Pro Glu Ile Ser Gln Pro Gln Lys Gly Arg Lys Pro Arg Asp Leu Glu
305                 310                 315                 320

Leu Pro Leu Xaa Pro Ser Leu Leu Gly Gly Pro Gly Pro Glu Arg Xaa
                325                 330                 335

Pro Gly Ser Gly Ser Gly Ser Gly Leu Gln Ala Pro Gly Pro Ala Leu
            340                 345                 350

Thr Pro Ser Leu Leu Pro Thr His Thr Leu Thr Pro Val Leu Leu Thr
        355                 360                 365

```
Pro Ser Ser Leu Pro Ser Ile His Phe Trp Ser Thr Leu Xaa Pro
        370                 375                 380

Ile Ala Pro Arg Xaa Pro Ala Lys Leu Ser Phe Gln Phe Pro Ser Ser
385                 390                 395                 400

Gly Ser Ala Gln Val His Ile Pro Ser Ile Ser Val Asp Gly Leu Ser
                405                 410                 415

Thr Pro Val Val Leu Xaa Pro Gly Pro Gln Lys Pro
            420                 425

<210> SEQ ID NO 15
<211> LENGTH: 676
<212> TYPE: PRT
<213> ORGANISM: Homo sapiens
<220> FEATURE:
<221> NAME/KEY: misc_feature
<222> LOCATION: (623)..(623)
<223> OTHER INFORMATION: Xaa can be any naturally occurring amino acid

<400> SEQUENCE: 15

Met Ser Gly Gly Gly Asp Val Val Cys Thr Gly Trp Leu Arg Lys Ser
1               5                   10                  15

Pro Pro Glu Lys Lys Leu Arg Arg Tyr Ala Trp Lys Lys Arg Trp Phe
            20                  25                  30

Ile Leu Arg Ser Gly Arg Met Ser Gly Asp Pro Asp Val Leu Glu Tyr
        35                  40                  45

Tyr Lys Asn Asp His Ser Lys Lys Pro Leu Arg Ile Ile Asn Leu Asn
    50                  55                  60

Phe Cys Glu Gln Val Asp Ala Gly Leu Thr Phe Asn Lys Lys Glu Leu
65                  70                  75                  80

Gln Asp Ser Phe Val Phe Asp Ile Lys Thr Ser Glu Arg Thr Phe Tyr
                85                  90                  95

Leu Val Ala Glu Thr Glu Glu Asp Met Asn Lys Trp Val Gln Ser Ile
            100                 105                 110

Cys Gln Ile Cys Gly Phe Asn Gln Ala Glu Glu Ser Thr Asp Ser Leu
        115                 120                 125

Arg Asn Val Ser Ser Ala Gly His Gly Pro Arg Ser Ser Pro Ala Glu
    130                 135                 140

Leu Ser Ser Ser Gln His Leu Leu Arg Glu Arg Lys Ser Ser Ala
145                 150                 155                 160

Pro Ser His Ser Ser Gln Pro Thr Leu Phe Thr Phe Glu Pro Pro Val
                165                 170                 175

Ser Asn His Met Gln Pro Thr Leu Ser Thr Ser Ala Pro Gln Glu Tyr
            180                 185                 190

Leu Tyr Leu His Gln Cys Ile Ser Arg Arg Ala Glu Asn Ala Arg Ser
        195                 200                 205

Ala Ser Phe Ser Gln Gly Thr Arg Ala Ser Phe Leu Met Arg Ser Asp
    210                 215                 220

Thr Ala Val Gln Lys Leu Ala Gln Gly Asn Gly His Cys Val Asn Gly
225                 230                 235                 240

Ile Ser Gly Gln Val His Gly Phe Tyr Ser Leu Pro Lys Pro Ser Arg
                245                 250                 255

His Asn Thr Glu Phe Arg Asp Ser Thr Tyr Asp Leu Pro Arg Ser Leu
            260                 265                 270

Ala Ser His Gly His Thr Lys Gly Ser Leu Thr Gly Ser Glu Thr Asp
        275                 280                 285

Asn Glu Asp Val Tyr Thr Phe Lys Thr Pro Ser Asn Thr Leu Cys Arg
```

```
            290                 295                 300
Glu Phe Gly Asp Leu Leu Val Asp Asn Met Asp Val Pro Ala Thr Pro
305                 310                 315                 320

Leu Ser Ala Tyr Gln Ile Pro Arg Thr Phe Thr Leu Asp Lys Asn His
                325                 330                 335

Asn Ala Met Thr Val Ala Thr Pro Gly Asp Ser Ala Ile Ala Pro Pro
            340                 345                 350

Pro Arg Pro Lys Pro Ser Gln Ala Glu Thr Pro Arg Trp Gly Ser
        355                 360                 365

Pro Gln Gln Arg Pro Pro Ile Ser Glu Asn Ser Arg Ser Val Ala Ala
        370                 375                 380

Thr Ile Pro Arg Arg Asn Thr Leu Pro Ala Met Asp Asn Ser Arg Leu
385                 390                 395                 400

His Arg Ala Ser Ser Cys Glu Thr Tyr Glu Tyr Pro Gln Arg Gly Gly
                405                 410                 415

Glu Ser Ala Gly Arg Ser Ala Glu Ser Met Ser Asp Gly Val Gly Ser
            420                 425                 430

Phe Leu Pro Gly Lys Met Ile Val Gly Arg Ser Asp Ser Thr Asn Ser
        435                 440                 445

Glu Asp Asn Tyr Val Pro Met Asn Pro Gly Ser Ser Thr Leu Leu Ala
450                 455                 460

Met Glu Arg Ala Gly Asp Asn Ser Gln Ser Val Tyr Ile Pro Met Ser
465                 470                 475                 480

Pro Gly Ala His His Phe Asp Ser Leu Gly Tyr Pro Ser Thr Thr Leu
                485                 490                 495

Pro Val His Arg Gly Pro Ser Arg Gly Ser Glu Ile Gln Pro Pro Pro
            500                 505                 510

Val Asn Arg Asn Leu Lys Pro Asp Arg Lys Ala Lys Pro Thr Pro Leu
        515                 520                 525

Asp Leu Arg Asn Asn Thr Val Ile Asp Glu Leu Pro Phe Lys Ser Pro
530                 535                 540

Ile Thr Lys Ser Trp Ser Arg Ala Asn His Thr Phe Asn Ser Ser Ser
545                 550                 555                 560

Ser Gln Tyr Cys Arg Pro Ile Ser Thr Gln Ser Ile Thr Ser Thr Asp
                565                 570                 575

Ser Gly Asp Ser Glu Glu Asn Tyr Val Pro Met Gln Asn Pro Val Ser
            580                 585                 590

Ala Ser Pro Val Pro Ser Gly Thr Asn Ser Pro Ala Pro Lys Lys Ser
        595                 600                 605

Thr Gly Ser Val Asp Tyr Leu Ala Leu Asp Phe Gln Pro Ser Xaa Pro
610                 615                 620

Ser Pro His Arg Lys Pro Ser Thr Ser Ser Val Thr Ser Asp Glu Lys
625                 630                 635                 640

Val Asp Tyr Val Gln Val Asp Lys Glu Lys Thr Gln Ala Leu Gln Asn
                645                 650                 655

Thr Met Gln Glu Trp Thr Asp Val Arg Gln Ser Ser Glu Pro Ser Lys
            660                 665                 670

Gly Ala Lys Leu
        675

<210> SEQ ID NO 16
<211> LENGTH: 169
<212> TYPE: PRT
<213> ORGANISM: Homo sapiens
<220> FEATURE:
```

```
<221> NAME/KEY: misc_feature
<222> LOCATION: (18)..(18)
<223> OTHER INFORMATION: Xaa can be any naturally occurring amino acid

<400> SEQUENCE: 16
```

| Met | Cys | His | Ser | Arg | Ser | Cys | His | Pro | Thr | Met | Thr | Ile | Leu | Gln | Ala |
|---|---|---|---|---|---|---|---|---|---|---|---|---|---|---|---|
| 1 | | | | 5 | | | | | 10 | | | | | 15 | |

| Pro | Xaa | Pro | Ala | Pro | Ser | Thr | Ile | Pro | Gly | Pro | Arg | Arg | Gly | Ser | Gly |
|---|---|---|---|---|---|---|---|---|---|---|---|---|---|---|---|
| | | | 20 | | | | | 25 | | | | | 30 | | |

| Pro | Glu | Ile | Phe | Thr | Phe | Asp | Pro | Leu | Pro | Glu | Pro | Ala | Ala | Ala | Pro |
|---|---|---|---|---|---|---|---|---|---|---|---|---|---|---|---|
| | | 35 | | | | | 40 | | | | | 45 | | | |

| Ala | Gly | Arg | Pro | Ser | Ala | Ser | Arg | Gly | His | Arg | Lys | Arg | Ser | Arg | Arg |
|---|---|---|---|---|---|---|---|---|---|---|---|---|---|---|---|
| | 50 | | | | | 55 | | | | | 60 | | | | |

| Val | Leu | Tyr | Pro | Arg | Val | Val | Arg | Arg | Gln | Leu | Pro | Val | Glu | Glu | Pro |
|---|---|---|---|---|---|---|---|---|---|---|---|---|---|---|---|
| 65 | | | | | 70 | | | | | 75 | | | | | 80 |

| Asn | Pro | Ala | Lys | Arg | Leu | Leu | Phe | Leu | Leu | Leu | Thr | Ile | Val | Phe | Cys |
|---|---|---|---|---|---|---|---|---|---|---|---|---|---|---|---|
| | | | | 85 | | | | | 90 | | | | | 95 | |

| Gln | Ile | Leu | Met | Ala | Glu | Glu | Gly | Val | Pro | Ala | Pro | Leu | Pro | Pro | Glu |
|---|---|---|---|---|---|---|---|---|---|---|---|---|---|---|---|
| | | | 100 | | | | | 105 | | | | | 110 | | |

| Asp | Ala | Pro | Asn | Ala | Ala | Ser | Leu | Ala | Pro | Thr | Pro | Arg | Ile | Pro | Asn |
|---|---|---|---|---|---|---|---|---|---|---|---|---|---|---|---|
| | | 115 | | | | | 120 | | | | | 125 | | | |

| Trp | Asp | Phe | Arg | Gly | Asn | Leu | Asn | Ser | Glu | His | Tyr | Ser | Gly | Asp | Ala |
|---|---|---|---|---|---|---|---|---|---|---|---|---|---|---|---|
| | 130 | | | | | 135 | | | | | 140 | | | | |

| Thr | Arg | Cys | Leu | Arg | Arg | Asp | Arg | Gly | Ala | Gln | Arg | Pro | Arg | Arg | Ile |
|---|---|---|---|---|---|---|---|---|---|---|---|---|---|---|---|
| 145 | | | | | 150 | | | | | 155 | | | | | 160 |

| Glu | Thr | Glu | Ala | Gln | Pro | Ser | Trp | Gly |
|---|---|---|---|---|---|---|---|---|
| | | | | 165 | | | | |

```
<210> SEQ ID NO 17
<211> LENGTH: 630
<212> TYPE: PRT
<213> ORGANISM: Homo sapiens
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid
<220> FEATURE:
<221> NAME/KEY: misc_feature
<222> LOCATION: (607)..(607)
<223> OTHER INFORMATION: Xaa can be any naturally occurring amino acid
<220> FEATURE:
<221> NAME/KEY: misc_feature
<222> LOCATION: (616)..(616)
<223> OTHER INFORMATION: Xaa can be any naturally occurring amino acid

<400> SEQUENCE: 17
```

| Met | Ala | Ala | Gly | Val | Ala | Ala | Trp | Leu | Pro | Phe | Ala | Arg | Ala | Ala | Ala |
|---|---|---|---|---|---|---|---|---|---|---|---|---|---|---|---|
| 1 | | | | 5 | | | | | 10 | | | | | 15 | |

| Ile | Gly | Trp | Met | Pro | Val | Ala | Ser | Gly | Pro | Met | Pro | Ala | Pro | Pro | Arg |
|---|---|---|---|---|---|---|---|---|---|---|---|---|---|---|---|
| | | | 20 | | | | | 25 | | | | | 30 | | |

| Gln | Glu | Arg | Lys | Arg | Thr | Gln | Asp | Ala | Leu | Ile | Val | Leu | Asn | Val | Ser |
|---|---|---|---|---|---|---|---|---|---|---|---|---|---|---|---|
| | | 35 | | | | | 40 | | | | | 45 | | | |

| Gly | Thr | Arg | Phe | Gln | Thr | Trp | Gln | Asp | Thr | Leu | Glu | Arg | Tyr | Pro | Asp |
|---|---|---|---|---|---|---|---|---|---|---|---|---|---|---|---|
| | 50 | | | | | 55 | | | | | 60 | | | | |

| Thr | Leu | Leu | Gly | Ser | Ser | Glu | Arg | Asp | Phe | Phe | Tyr | His | Pro | Glu | Thr |
|---|---|---|---|---|---|---|---|---|---|---|---|---|---|---|---|

```
                65                   70                   75                  80
Gln Gln Tyr Phe Phe Asp Arg Asp Pro Asp Ile Phe Arg His Ile Leu
                        85                   90                   95
Asn Phe Tyr Arg Thr Gly Lys Leu His Tyr Pro Arg His Glu Cys Ile
                100                  105                  110
Ser Ala Tyr Asp Glu Glu Leu Ala Phe Phe Gly Leu Ile Pro Glu Ile
                115                  120                  125
Ile Gly Asp Cys Cys Tyr Glu Glu Tyr Lys Asp Arg Arg Glu Asn
                130                  135                  140
Ala Glu Arg Leu Gln Asp Asp Ala Asp Thr Asp Thr Ala Gly Glu Ser
145                  150                  155                  160
Ala Leu Pro Thr Met Thr Ala Arg Gln Arg Val Trp Arg Ala Phe Glu
                165                  170                  175
Asn Pro His Thr Ser Thr Met Ala Leu Val Phe Tyr Val Thr Gly
                180                  185                  190
Phe Phe Ile Ala Val Ser Val Ile Ala Asn Val Val Glu Thr Val Pro
                195                  200                  205
Cys Gly Ser Ser Pro Gly His Ile Lys Glu Leu Pro Cys Gly Xaa Arg
                210                  215                  220
Tyr Ala Val Ala Phe Phe Cys Leu Asp Thr Ala Cys Val Met Ile Phe
225                  230                  235                  240
Thr Val Glu Tyr Leu Leu Arg Leu Ala Ala Ala Pro Ser Arg Tyr Arg
                245                  250                  255
Phe Val Arg Ser Val Met Ser Ile Ile Asp Val Val Ala Ile Leu Pro
                260                  265                  270
Tyr Tyr Ile Gly Leu Val Met Thr Asp Asn Glu Asp Val Ser Gly Ala
                275                  280                  285
Phe Val Thr Leu Arg Val Phe Arg Val Phe Arg Ile Phe Lys Phe Ser
                290                  295                  300
Arg His Ser Gln Gly Leu Arg Ile Leu Gly Tyr Thr Leu Lys Ser Xaa
305                  310                  315                  320
Ala Ser Glu Leu Gly Phe Leu Leu Phe Ser Leu Thr Met Ala Ile Ile
                325                  330                  335
Ile Phe Ala Thr Val Met Phe Tyr Ala Glu Lys Gly Ser Ser Ala Ser
                340                  345                  350
Lys Phe Thr Ser Ile Pro Ala Ala Phe Trp Tyr Thr Ile Val Thr Met
                355                  360                  365
Thr Thr Leu Gly Tyr Gly Asp Met Val Pro Lys Thr Ile Ala Gly Lys
                370                  375                  380
Ile Phe Gly Ser Ile Cys Ser Leu Ser Gly Val Leu Val Ile Ala Leu
385                  390                  395                  400
Pro Val Pro Val Ile Val Ser Asn Phe Ser Arg Ile Tyr His Gln Asn
                405                  410                  415
Gln Arg Ala Asp Lys Arg Ala Gln Lys Lys Ala Arg Leu Ala Arg
                420                  425                  430
Ile Arg Ala Ala Lys Ser Gly Ser Ala Asn Ala Tyr Met Gln Ser Lys
                435                  440                  445
Arg Asn Gly Leu Leu Ser Asn Gln Leu Gln Ser Ser Glu Asp Glu Gln
                450                  455                  460
Ala Phe Val Ser Lys Ser Gly Ser Ser Phe Glu Thr Gln His His His
465                  470                  475                  480
Leu Leu His Cys Leu Glu Lys Thr Thr Asn His Glu Phe Val Asp Glu
                485                  490                  495
```

```
Gln Val Phe Glu Glu Ser Cys Met Glu Val Ala Thr Val Asn Arg Pro
                500                 505                 510

Ser Ser His Ser Pro Ser Leu Ser Gln Gln Gly Val Thr Ser Thr
        515                 520                 525

Cys Cys Ser Arg Arg His Lys Lys Thr Phe Arg Ile Pro Asn Ala Asn
530                 535                 540

Val Ser Gly Ser His Gln Gly Ser Ile Gln Glu Leu Ser Thr Ile Gln
545                 550                 555                 560

Ile Arg Cys Val Glu Arg Thr Pro Leu Ser Asn Ser Arg Ser Leu
                565                 570                 575

Asn Ala Lys Met Glu Glu Cys Val Lys Leu Asn Cys Glu Gln Pro Tyr
                580                 585                 590

Val Thr Thr Ala Ile Ile Ser Ile Pro Xaa Pro Pro Val Thr Xaa Pro
            595                 600                 605

Glu Gly Asp Asp Arg Pro Glu Xaa Pro Glu Tyr Ser Gly Gly Asn Ile
            610                 615                 620

Val Arg Val Ser Ala Leu
625                 630

<210> SEQ ID NO 18
<211> LENGTH: 744
<212> TYPE: PRT
<213> ORGANISM: Homo sapiens
<220> FEATURE:
<221> NAME/KEY: misc_feature
<222> LOCATION: (389)..(389)
<223> OTHER INFORMATION: Xaa can be any naturally occurring amino acid

<400> SEQUENCE: 18

Met Glu Gln Asp Pro Lys Pro Arg Leu Arg Leu Trp Ala Leu Ile
1               5                   10                  15

Pro Trp Leu Pro Arg Lys Gln Arg Pro Arg Ile Ser Gln Thr Ser Leu
                20                  25                  30

Pro Val Pro Gly Pro Gly Ser Gly Pro Gln Arg Asp Ser Asp Glu Gly
            35                  40                  45

Val Leu Lys Glu Ile Ser Ile Thr His His Val Lys Ala Gly Ser Glu
50                  55                  60

Lys Ala Asp Pro Ser His Phe Glu Leu Leu Lys Val Leu Gly Gln Gly
65                  70                  75                  80

Ser Phe Gly Lys Val Phe Leu Val Arg Lys Val Thr Arg Pro Asp Ser
                85                  90                  95

Gly His Leu Tyr Ala Met Lys Val Leu Lys Lys Ala Thr Leu Lys Val
            100                 105                 110

Arg Asp Arg Val Arg Thr Lys Met Glu Arg Asp Ile Leu Ala Asp Val
        115                 120                 125

Asn His Pro Phe Val Val Lys Leu His Tyr Ala Phe Gln Thr Glu Gly
    130                 135                 140

Lys Leu Tyr Leu Ile Leu Asp Phe Leu Arg Gly Gly Asp Leu Phe Thr
145                 150                 155                 160

Arg Leu Ser Lys Glu Val Met Phe Thr Glu Glu Asp Val Lys Phe Tyr
                165                 170                 175

Leu Ala Glu Leu Ala Leu Gly Leu Asp His Leu His Ser Leu Gly Ile
            180                 185                 190

Ile Tyr Arg Asp Leu Lys Pro Glu Asn Ile Leu Leu Asp Glu Glu Gly
        195                 200                 205

His Ile Lys Leu Thr Asp Phe Gly Leu Ser Lys Glu Ala Ile Asp His
    210                 215                 220
```

```
Glu Lys Lys Ala Tyr Ser Phe Cys Gly Thr Val Glu Tyr Met Ala Pro
225                 230                 235                 240

Glu Val Val Asn Arg Gln Gly His Ser His Ser Ala Asp Trp Trp Ser
                245                 250                 255

Tyr Gly Val Leu Met Phe Glu Met Leu Thr Gly Ser Leu Pro Phe Gln
            260                 265                 270

Gly Lys Asp Arg Lys Glu Thr Met Thr Leu Ile Leu Lys Ala Lys Leu
        275                 280                 285

Gly Met Pro Gln Phe Leu Ser Thr Glu Ala Gln Ser Leu Leu Arg Ala
    290                 295                 300

Leu Phe Lys Arg Asn Pro Ala Asn Arg Leu Gly Ser Gly Pro Asp Gly
305                 310                 315                 320

Ala Glu Glu Ile Lys Arg His Val Phe Tyr Ser Thr Ile Asp Trp Asn
                325                 330                 335

Lys Leu Tyr Arg Arg Glu Ile Lys Pro Pro Phe Lys Pro Ala Val Ala
            340                 345                 350

Gln Pro Asp Asp Thr Phe Tyr Phe Asp Thr Glu Phe Thr Ser Arg Thr
        355                 360                 365

Pro Lys Asp Ser Pro Gly Ile Pro Pro Ser Ala Gly Ala His Gln Leu
    370                 375                 380

Phe Arg Gly Phe Xaa Phe Val Ala Thr Gly Leu Met Glu Asp Asp Gly
385                 390                 395                 400

Lys Pro Arg Ala Pro Gln Ala Pro Leu His Ser Val Val Gln Gln Leu
                405                 410                 415

His Gly Lys Asn Leu Val Phe Ser Asp Gly Tyr Val Val Lys Glu Thr
            420                 425                 430

Ile Gly Val Gly Ser Tyr Ser Glu Cys Lys Arg Cys Val His Lys Ala
        435                 440                 445

Thr Asn Met Glu Tyr Ala Val Lys Val Ile Asp Lys Ser Lys Arg Asp
    450                 455                 460

Pro Ser Glu Glu Ile Glu Ile Leu Leu Arg Tyr Gly Gln His Pro Asn
465                 470                 475                 480

Ile Ile Thr Leu Lys Asp Val Tyr Asp Asp Gly Lys His Val Tyr Leu
                485                 490                 495

Val Thr Glu Leu Met Arg Gly Gly Glu Leu Leu Asp Lys Ile Leu Arg
            500                 505                 510

Gln Lys Phe Phe Ser Glu Arg Glu Ala Ser Phe Val Leu His Thr Ile
        515                 520                 525

Gly Lys Thr Val Glu Tyr Leu His Ser Gln Gly Val Val His Arg Asp
    530                 535                 540

Leu Lys Pro Ser Asn Ile Leu Tyr Val Asp Glu Ser Gly Asn Pro Glu
545                 550                 555                 560

Cys Leu Arg Ile Cys Asp Phe Gly Phe Ala Lys Gln Leu Arg Ala Glu
                565                 570                 575

Asn Gly Leu Leu Met Thr Pro Cys Tyr Thr Ala Asn Phe Val Ala Pro
            580                 585                 590

Glu Val Leu Lys Arg Gln Gly Tyr Asp Glu Gly Cys Asp Ile Trp Ser
        595                 600                 605

Leu Gly Ile Leu Leu Tyr Thr Met Leu Ala Gly Tyr Thr Pro Phe Ala
    610                 615                 620

Asn Gly Pro Ser Asp Thr Pro Glu Glu Ile Leu Thr Arg Ile Gly Ser
625                 630                 635                 640

Gly Lys Phe Thr Leu Ser Gly Gly Asn Trp Asn Thr Val Ser Glu Thr
```

```
                    645                 650                 655

Ala Lys Asp Leu Val Ser Lys Met Leu His Val Asp Pro His Gln Arg
                660                 665                 670

Leu Thr Ala Lys Gln Val Leu Gln His Pro Trp Val Thr Gln Lys Asp
            675                 680                 685

Lys Leu Pro Gln Ser Gln Leu Ser His Gln Asp Leu Gln Leu Val Lys
        690                 695                 700

Gly Ala Met Ala Ala Thr Tyr Ser Ala Leu Asn Ser Ser Lys Pro Thr
705                 710                 715                 720

Pro Gln Leu Lys Pro Ile Glu Ser Ser Ile Leu Ala Gln Arg Arg Val
                725                 730                 735

Arg Lys Leu Pro Ser Thr Thr Leu
                740

<210> SEQ ID NO 19
<211> LENGTH: 557
<212> TYPE: PRT
<213> ORGANISM: mouse
<220> FEATURE:
<221> NAME/KEY: misc_feature
<222> LOCATION: (83)..(83)
<223> OTHER INFORMATION: Xaa can be any naturally occurring amino acid

<400> SEQUENCE: 19

Met Asp Asp Leu Asp Ala Leu Leu Ala Asp Leu Glu Ser Thr Thr Ser
1               5                   10                  15

His Ile Ser Lys Arg Pro Val Phe Leu Ser Glu Glu Pro Pro Tyr Ser
                20                  25                  30

Tyr Pro Thr Gly Asn His Thr Tyr Gln Glu Ile Ala Val Pro Pro Pro
            35                  40                  45

Val Pro Pro Pro Ser Ser Glu Ala Leu Asn Gly Thr Val Leu Asp
    50                  55                  60

Pro Leu Asp Gln Trp Gln Pro Ser Gly Ser Arg Tyr Ala His Gln Gln
65                  70                  75                  80

Pro Pro Xaa Pro Leu Pro Val Tyr Ser Ser Ala Lys Asn Ser Ser
                85                  90                  95

Ala Ser Asn Thr Gln Asp Gly Val Gly Ser Leu Cys Ser Arg Ala Gly
                100                 105                 110

Glu Glu Glu His Val Tyr Ser Phe Pro Asn Lys Gln Lys Ser Ala Glu
            115                 120                 125

Pro Ser Pro Thr Val Met Ser Ser Ser Leu Gly Ser Asn Leu Ser Glu
        130                 135                 140

Leu Asp Arg Leu Leu Leu Glu Leu Asn Ala Val Gln His Ser Pro Pro
145                 150                 155                 160

Gly Phe Pro Ala Asp Glu Ala Glu Ser Ser Pro Pro Leu Pro Gly Ala
                165                 170                 175

Leu Ser Pro Leu Tyr Gly Ile Pro Glu Asn Asn Thr Pro Leu Gly Gly
            180                 185                 190

Lys Ala Gly Pro Leu Val Lys Glu Lys Pro Lys Arg Asn Gly Gly Arg
        195                 200                 205

Gly Leu Glu Asp Val Arg Pro Ser Val Glu Ser Leu Leu Asp Glu Leu
    210                 215                 220

Glu Ser Ser Val Pro Ser Pro Val Pro Ala Ile Thr Val Asn Gln Gly
225                 230                 235                 240

Glu Met Ser Ser Pro Gln Arg Val Thr Ser Ser Gln Gln Gln Thr Arg
                245                 250                 255
```

```
Ile Ser Ala Ser Ser Ala Thr Arg Glu Leu Asp Glu Leu Met Ala Ser
            260                 265                 270

Leu Ser Asp Phe Lys Phe Met Ala Gln Gly Lys Thr Gly Ser Ser Ser
        275                 280                 285

Pro Pro Gly Gly Leu Ser Lys Pro Gly Ser Gln Leu Asp Ser Met Leu
    290                 295                 300

Gly Ser Leu Gln Ser Asp Leu Asn Lys Leu Gly Val Ala Thr Val Ala
305                 310                 315                 320

Lys Gly Val Cys Gly Ala Cys Lys Lys Pro Ile Ala Gly Gln Val Val
                325                 330                 335

Thr Ala Met Gly Lys Thr Trp His Pro Glu His Phe Val Cys Thr His
            340                 345                 350

Cys Gln Glu Glu Ile Gly Ser Arg Asn Phe Phe Glu Arg Asp Gly Gln
        355                 360                 365

Pro Tyr Cys Glu Lys Asp Tyr His Ser Leu Phe Ser Pro Arg Cys Tyr
    370                 375                 380

Tyr Cys Asn Gly Pro Ile Leu Asp Lys Val Val Thr Ala Leu Asp Arg
385                 390                 395                 400

Thr Trp His Pro Glu His Phe Phe Cys Ala Gln Cys Gly Ala Phe Phe
                405                 410                 415

Gly Pro Glu Gly Phe His Glu Lys Asp Gly Lys Ala Tyr Cys Arg Lys
            420                 425                 430

Asp Tyr Phe Asp Met Phe Ala Pro Lys Cys Gly Gly Cys Ala Arg Ala
        435                 440                 445

Ile Leu Glu Asn Tyr Ile Ser Ala Leu Asn Thr Leu Trp His Pro Glu
    450                 455                 460

Cys Phe Val Cys Arg Glu Cys Phe Thr Pro Phe Val Asn Gly Ser Phe
465                 470                 475                 480

Phe Glu His Asp Gly Gln Pro Tyr Cys Glu Val His Tyr His Glu Arg
                485                 490                 495

Arg Gly Ser Leu Cys Ser Gly Cys Gln Lys Pro Ile Thr Gly Arg Cys
            500                 505                 510

Ile Thr Ala Met Ala Lys Lys Phe His Pro Glu His Phe Val Cys Ala
        515                 520                 525

Phe Cys Leu Lys Gln Leu Asn Lys Gly Thr Phe Lys Glu Gln Asn Asp
    530                 535                 540

Lys Pro Tyr Cys Gln Ser Cys Phe Val Lys Leu Phe Cys
545                 550                 555

<210> SEQ ID NO 20
<211> LENGTH: 1173
<212> TYPE: PRT
<213> ORGANISM: mouse
<220> FEATURE:
<221> NAME/KEY: misc_feature
<222> LOCATION: (982)..(982)
<223> OTHER INFORMATION: Xaa can be any naturally occurring amino acid

<400> SEQUENCE: 20

Met Ala Gly Ala Gln Pro Gly Val His Ala Leu Gln Leu Lys Pro Val
1               5                   10                  15

Cys Val Ser Asp Ser Leu Lys Lys Gly Thr Lys Leu Val Lys Trp Asp
            20                  25                  30

Asp Asp Ser Thr Ile Val Thr Pro Thr Ile Leu Arg Thr Asp Pro Gln
        35                  40                  45

Gly Phe Phe Phe Tyr Trp Thr Asp Gln Asn Lys Glu Thr Glu Leu Leu
    50                  55                  60
```

```
Asp Leu Ser Leu Val Lys Asp Ala Arg Cys Gly Lys His Ala Glu Ala
 65                  70                  75                  80

Pro Lys Asp Pro Lys Leu Arg Glu Leu Leu Asp Val Gly Asn Ile Gly
                 85                  90                  95

His Leu Glu Gln Arg Met Ile Thr Val Val Tyr Gly Pro Asp Leu Ala
            100                 105                 110

Asn Ile Ser His Leu Asn Leu Val Ala Phe Gln Glu Glu Val Ala Lys
            115                 120                 125

Glu Trp Thr Asn Glu Val Phe Ser Leu Ala Thr Asn Leu Leu Ala Gln
        130                 135                 140

Asn Met Ser Arg Asp Ala Phe Leu Glu Lys Ala Tyr Thr Lys Leu Lys
145                 150                 155                 160

Leu Gln Val Thr Pro Glu Gly Arg Ile Pro Leu Lys Asn Ile Tyr Arg
                165                 170                 175

Leu Phe Ser Ala Asp Arg Lys Arg Val Glu Thr Ala Leu Glu Ala Cys
            180                 185                 190

Ser Leu Pro Ser Ser Arg Asn Asp Ser Ile Pro Gln Glu Asp Phe Thr
            195                 200                 205

Pro Asp Val Tyr Arg Val Phe Leu Asn Asn Leu Cys Pro Arg Pro Glu
        210                 215                 220

Ile Asp Asn Ile Phe Ser Glu Phe Gly Ala Lys Ser Lys Pro Tyr Leu
225                 230                 235                 240

Thr Val Asp Gln Met Met Asp Phe Ile Asn Leu Lys Gln Arg Asp Pro
                245                 250                 255

Arg Leu Asn Glu Ile Leu Tyr Pro Pro Leu Lys Gln Glu Gln Val Gln
            260                 265                 270

Val Leu Ile Glu Lys Tyr Glu Pro Asn Ser Ser Leu Ala Lys Lys Gly
            275                 280                 285

Gln Met Ser Val Asp Gly Phe Met Arg Tyr Leu Ser Gly Glu Glu Asn
        290                 295                 300

Gly Val Val Ser Pro Glu Lys Leu Asp Leu Asn Glu Asp Met Ser Gln
305                 310                 315                 320

Pro Leu Ser His Tyr Phe Ile Asn Ser Ser His Asn Thr Tyr Leu Thr
                325                 330                 335

Ala Gly Gln Leu Ala Gly Asn Ser Ser Val Glu Met Tyr Arg Gln Val
            340                 345                 350

Leu Leu Ser Gly Cys Arg Cys Val Glu Leu Asp Cys Trp Lys Gly Arg
            355                 360                 365

Thr Ala Glu Glu Glu Pro Val Ile Thr His Gly Phe Thr Met Thr Thr
        370                 375                 380

Glu Ile Ser Phe Lys Glu Val Ile Glu Ala Ile Ala Glu Cys Ala Phe
385                 390                 395                 400

Lys Thr Ser Pro Phe Pro Ile Leu Leu Ser Phe Glu Asn His Val Asp
                405                 410                 415

Ser Pro Lys Gln Gln Ala Lys Met Ala Glu Tyr Cys Arg Leu Ile Phe
            420                 425                 430

Gly Asp Ala Leu Leu Met Glu Pro Leu Glu Lys Tyr Pro Leu Glu Ser
            435                 440                 445

Gly Val Pro Leu Pro Ser Pro Met Asp Leu Met Tyr Lys Ile Leu Val
        450                 455                 460

Lys Asn Lys Lys Lys Ser His Lys Ser Ser Glu Gly Ser Gly Lys Lys
465                 470                 475                 480

Lys Leu Ser Glu Gln Ala Ser Asn Thr Tyr Ser Asp Ser Ser Ser Val
```

-continued

```
                485                 490                 495
Phe Glu Pro Ser Ser Pro Gly Ala Gly Glu Ala Asp Thr Glu Ser Asp
                500                 505                 510
Asp Asp Asp Asp Asp Asp Cys Lys Lys Ser Ser Met Asp Glu Gly
            515                 520                 525
Thr Ala Gly Ser Glu Ala Met Ala Thr Glu Glu Met Ser Asn Leu Val
            530                 535                 540
Asn Tyr Ile Gln Pro Val Lys Phe Glu Ser Phe Glu Ile Ser Lys Lys
545                 550                 555                 560
Arg Asn Lys Ser Phe Glu Met Ser Ser Phe Val Glu Thr Lys Gly Leu
                565                 570                 575
Glu Gln Leu Thr Lys Ser Pro Val Glu Phe Val Glu Tyr Asn Lys Met
            580                 585                 590
Gln Leu Ser Arg Ile Tyr Pro Lys Gly Thr Arg Val Asp Ser Ser Asn
            595                 600                 605
Tyr Met Pro Gln Leu Phe Trp Asn Ala Gly Cys Gln Met Met Ala Leu
            610                 615                 620
Asn Phe Gln Thr Val Asp Leu Ala Met Gln Ile Asn Met Gly Met Tyr
625                 630                 635                 640
Glu Tyr Asn Gly Lys Ser Gly Tyr Arg Leu Lys Pro Glu Phe Met Arg
                645                 650                 655
Arg Pro Asp Lys His Phe Asp Pro Phe Thr Glu Gly Ile Val Asp Gly
                660                 665                 670
Ile Val Ala Asn Thr Leu Ser Val Lys Ile Ile Ser Gly Gln Phe Leu
                675                 680                 685
Ser Asp Lys Lys Val Gly Thr Tyr Val Glu Val Asp Met Phe Gly Leu
            690                 695                 700
Pro Val Asp Thr Arg Arg Lys Ala Phe Thr Thr Lys Thr Ser Gln Gly
705                 710                 715                 720
Asn Ala Val Asn Pro Val Trp Glu Glu Pro Ile Val Phe Lys Lys
                725                 730                 735
Val Val Leu Pro Ser Leu Ala Cys Leu Arg Ile Ala Ala Tyr Glu Glu
            740                 745                 750
Gly Gly Lys Phe Ile Gly His Arg Ile Leu Pro Val Gln Ala Ile Arg
            755                 760                 765
Pro Gly Tyr His Tyr Ile Cys Leu Arg Asn Glu Arg Asn Gln Pro Leu
            770                 775                 780
Thr Leu Pro Ala Val Phe Val Tyr Ile Glu Asp Lys Asp Tyr Val Pro
785                 790                 795                 800
Asp Thr Tyr Ala Asp Val Ile Glu Ala Leu Ser Asn Pro Ile Arg Tyr
                805                 810                 815
Val Asn Leu Met Glu Gln Arg Ala Lys Gln Leu Ala Ala Leu Thr Leu
                820                 825                 830
Glu Asp Glu Glu Glu Val Lys Lys Glu Ala Asp Pro Gly Glu Thr Ser
            835                 840                 845
Ser Glu Ala Pro Ser Glu Thr Arg Thr Thr Pro Ala Glu Asn Gly Val
            850                 855                 860
Asn His Thr Ala Ser Leu Ala Pro Lys Pro Pro Ser Gln Ala Pro His
865                 870                 875                 880
Ser Gln Pro Ala Pro Gly Ser Val Lys Ala Pro Ala Lys Thr Glu Asp
                885                 890                 895
Leu Ile Gln Ser Val Leu Thr Glu Val Glu Ala Gln Thr Ile Glu Glu
            900                 905                 910
```

Leu Lys Gln Gln Lys Ser Phe Val Lys Leu His Lys Lys His Tyr Lys
    915                 920                 925

Glu Met Lys Asp Leu Val Lys Arg His His Lys Lys Thr Thr Glu Leu
    930                 935                 940

Ile Lys Glu His Thr Thr Lys Tyr Asn Glu Ile Gln Ile Asp Tyr Leu
945                 950                 955                 960

Arg Arg Arg Ala Ala Leu Glu Lys Ser Ala Lys Lys Asp Ser Lys Lys
                965                 970                 975

Lys Ser Glu Pro Ser Xaa Pro Asp His Gly Ser Ser Ala Ile Glu Gln
            980                 985                 990

Asp Leu Ala Ala Leu Asp Ala Glu Met Thr Gln Lys Leu Ile Asp Leu
        995                 1000                1005

Lys Asp Lys Gln Gln Gln Gln Leu Leu Asn Leu Arg Gln Glu Gln
    1010                1015                1020

Tyr Tyr Ser Glu Lys Tyr Gln Lys Arg Glu His Ile Lys Leu Leu
    1025                1030                1035

Ile Gln Lys Leu Thr Asp Val Ala Glu Glu Cys Gln Asn Asn Gln
    1040                1045                1050

Leu Lys Lys Leu Lys Glu Ile Cys Glu Lys Glu Lys Lys Glu Leu
    1055                1060                1065

Lys Lys Lys Met Asp Lys Lys Arg Gln Glu Lys Ile Thr Glu Ala
    1070                1075                1080

Thr Ser Lys Asp Lys Ser Gln Met Glu Glu Glu Lys Thr Glu Met
    1085                1090                1095

Ile Arg Ser Tyr Ile Gln Glu Val Val Gln Tyr Ile Lys Arg Leu
    1100                1105                1110

Glu Glu Ala Gln Ser Lys Arg Gln Glu Lys Leu Val Glu Lys His
    1115                1120                1125

Asn Glu Ile Arg Gln Gln Ile Leu Asp Glu Lys Pro Lys Gly Glu
    1130                1135                1140

Gly Pro Ser Ser Val Leu Ser Glu Gly Cys His Glu Asp Pro Ser
    1145                1150                1155

Val Pro Pro Asn Phe Thr Pro Pro Asn Pro Gln Ala Leu Lys Trp
    1160                1165                1170

<210> SEQ ID NO 21
<211> LENGTH: 443
<212> TYPE: PRT
<213> ORGANISM: Homo sapiens
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid

<400> SEQUENCE: 21

Met Gln Arg Arg Asp Asp Pro Ala Ala Arg Met Ser Arg Ser Ser Gly
1               5                   10                  15

Arg Ser Gly Ser Met Asp Pro Ser Gly Ala His Pro Ser Val Arg Gln
            20                  25                  30

Thr Pro Ser Arg Gln Pro Pro Leu Pro His Arg Ser Arg Gly Gly Gly
        35                  40                  45

```
Gly Gly Ser Arg Gly Gly Ala Arg Ala Xaa Pro Ala Thr Gln Pro Pro
         50                  55                  60

Pro Leu Leu Pro Pro Ser Ala Xaa Gly Pro Asp Ala Thr Val Gly Gly
 65                  70                  75                  80

Pro Ala Pro Xaa Pro Leu Leu Pro Pro Ser Ala Thr Ala Ser Val Lys
             85                  90                  95

Met Glu Pro Glu Asn Lys Tyr Leu Pro Glu Leu Met Ala Glu Lys Asp
             100                 105                 110

Ser Leu Asp Pro Ser Phe Thr His Ala Met Gln Leu Leu Thr Ala Glu
             115                 120                 125

Ile Glu Lys Ile Gln Lys Gly Asp Ser Lys Asp Asp Glu Glu Asn
130                 135                 140

Tyr Leu Asp Leu Phe Ser His Lys Asn Met Lys Leu Lys Glu Arg Val
145                 150                 155                 160

Leu Ile Pro Val Lys Gln Tyr Pro Lys Phe Asn Phe Val Gly Lys Ile
                 165                 170                 175

Leu Gly Pro Gln Gly Asn Thr Ile Lys Arg Leu Gln Glu Glu Thr Gly
             180                 185                 190

Ala Lys Ile Ser Val Leu Gly Lys Gly Ser Met Arg Asp Lys Ala Lys
             195                 200                 205

Glu Glu Glu Leu Arg Lys Gly Gly Asp Pro Lys Tyr Ala His Leu Asn
             210                 215                 220

Met Asp Leu His Val Phe Ile Glu Val Phe Gly Pro Pro Cys Glu Ala
225                 230                 235                 240

Tyr Ala Leu Met Ala His Ala Met Glu Glu Val Lys Lys Phe Leu Val
                 245                 250                 255

Pro Asp Met Met Asp Asp Ile Cys Gln Glu Gln Phe Leu Glu Leu Ser
             260                 265                 270

Tyr Leu Asn Gly Val Pro Glu Pro Ser Arg Gly Arg Gly Val Pro Val
             275                 280                 285

Arg Gly Arg Gly Ala Ala Pro Pro Pro Pro Val Pro Arg Gly Arg
         290                 295                 300

Gly Val Gly Pro Pro Arg Gly Ala Leu Val Arg Gly Thr Pro Val Arg
305                 310                 315                 320

Gly Ala Ile Thr Arg Gly Ala Thr Val Thr Arg Gly Val Pro Pro Pro
                 325                 330                 335

Pro Thr Val Arg Gly Ala Pro Ala Pro Arg Ala Arg Thr Ala Gly Ile
             340                 345                 350

Gln Arg Ile Pro Leu Pro Pro Pro Ala Pro Glu Thr Tyr Glu Glu
             355                 360                 365

Tyr Gly Tyr Asp Asp Thr Tyr Ala Glu Gln Ser Tyr Glu Gly Tyr Glu
             370                 375                 380

Gly Tyr Tyr Ser Gln Ser Gln Gly Asp Ser Glu Tyr Tyr Asp Tyr Gly
385                 390                 395                 400

His Gly Glu Val Gln Asp Ser Tyr Glu Ala Tyr Gly Gln Asp Asp Trp
                 405                 410                 415

Asn Gly Thr Arg Pro Ser Leu Lys Ala Pro Ala Arg Pro Val Lys
             420                 425                 430

Gly Ala Tyr Arg Glu His Pro Tyr Gly Arg Tyr
             435                 440

<210> SEQ ID NO 22
<211> LENGTH: 425
<212> TYPE: PRT
<213> ORGANISM: Homo sapiens
```

```
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid

<400> SEQUENCE: 22

Met Ser Ser Ile Leu Pro Phe Thr Pro Pro Ile Val Lys Arg Leu Leu
1               5                   10                  15

Gly Trp Lys Lys Gly Glu Gln Asn Gly Gln Glu Glu Lys Trp Cys Glu
            20                  25                  30

Lys Ala Val Lys Ser Leu Val Lys Lys Leu Lys Lys Thr Gly Gln Leu
        35                  40                  45

Asp Glu Leu Glu Lys Ala Ile Thr Thr Gln Asn Val Asn Thr Lys Cys
    50                  55                  60

Ile Thr Ile Pro Arg Ser Leu Asp Gly Arg Leu Gln Val Ser His Arg
65                  70                  75                  80

Lys Gly Leu Pro His Val Ile Tyr Cys Arg Leu Trp Arg Trp Pro Asp
                85                  90                  95

Leu His Ser His His Glu Leu Arg Ala Met Glu Leu Cys Glu Phe Ala
            100                 105                 110

Phe Asn Met Lys Lys Asp Glu Val Cys Val Asn Pro Tyr His Tyr Gln
        115                 120                 125

Arg Val Glu Thr Pro Val Leu Pro Pro Val Leu Val Pro Arg His Thr
    130                 135                 140

Glu Ile Pro Ala Glu Phe Pro Pro Leu Asp Asp Tyr Ser His Ser Ile
145                 150                 155                 160

Pro Glu Asn Thr Asn Phe Pro Ala Gly Ile Glu Pro Gln Ser Asn Ile
                165                 170                 175

Pro Glu Xaa Pro Pro Pro Gly Tyr Leu Ser Glu Asp Gly Glu Thr Ser
            180                 185                 190

Asp His Gln Met Asn His Ser Met Asp Ala Gly Xaa Pro Asn Leu Xaa
        195                 200                 205

Pro Asn Pro Met Ser Pro Ala His Asn Asn Leu Asp Leu Gln Pro Val
    210                 215                 220

Thr Tyr Cys Glu Pro Ala Phe Trp Cys Ser Ile Ser Tyr Tyr Glu Leu
225                 230                 235                 240

Asn Gln Arg Val Gly Glu Thr Phe His Ala Ser Gln Pro Ser Met Thr
                245                 250                 255

Val Asp Gly Phe Thr Asp Pro Ser Asn Ser Glu Arg Phe Cys Leu Gly
            260                 265                 270

Leu Leu Ser Asn Val Asn Arg Asn Ala Ala Val Glu Leu Thr Arg Arg
        275                 280                 285

His Ile Gly Arg Gly Val Arg Leu Tyr Tyr Ile Gly Gly Glu Val Phe
    290                 295                 300

Ala Glu Cys Leu Ser Asp Ser Ala Ile Phe Val Gln Ser Pro Asn Cys
305                 310                 315                 320

Asn Gln Arg Tyr Gly Trp His Pro Ala Thr Val Cys Lys Ile Pro Pro
                325                 330                 335

Gly Cys Asn Leu Lys Ile Phe Asn Asn Gln Glu Phe Ala Ala Leu Leu
            340                 345                 350
```

Ala Gln Ser Val Asn Gln Gly Phe Glu Ala Val Tyr Gln Leu Thr Arg
        355                 360                 365

Met Cys Thr Ile Arg Met Ser Phe Val Lys Gly Trp Gly Ala Glu Tyr
    370                 375                 380

Arg Arg Gln Thr Val Thr Ser Thr Pro Cys Trp Ile Glu Leu His Leu
385                 390                 395                 400

Asn Gly Pro Leu Gln Trp Leu Asp Lys Val Leu Thr Gln Met Gly Ser
                405                 410                 415

Pro Ser Ile Arg Cys Ser Ser Val Ser
            420                 425

<210> SEQ ID NO 23
<211> LENGTH: 770
<212> TYPE: PRT
<213> ORGANISM: Homo sapiens
<220> FEATURE:
<221> NAME/KEY: misc_feature
<222> LOCATION: (727)..(727)
<223> OTHER INFORMATION: Xaa can be any naturally occurring amino acid

<400> SEQUENCE: 23

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln

```
                    275                 280                 285
Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700
```

```
Tyr Leu Lys Thr Lys Phe Ile Cys Val Thr Pro Thr Thr Cys Ser Asn
705                 710                 715                 720

Thr Ile Asp Leu Pro Met Xaa Pro Arg Thr Leu Asp Ser Leu Met Gln
            725                 730                 735

Phe Gly Asn Asn Gly Glu Gly Ala Glu Pro Ser Ala Gly Gly Gln Phe
        740                 745                 750

Glu Ser Leu Thr Phe Asp Met Glu Leu Thr Ser Glu Cys Ala Thr Ser
    755                 760                 765

Pro Met
    770

<210> SEQ ID NO 24
<211> LENGTH: 824
<212> TYPE: PRT
<213> ORGANISM: Homo sapiens
<220> FEATURE:
<221> NAME/KEY: misc_feature
<222> LOCATION: (735)..(735)
<223> OTHER INFORMATION: Xaa can be any naturally occurring amino acid

<400> SEQUENCE: 24

Met Arg Gln Ser Leu Leu Phe Leu Thr Ser Val Val Pro Phe Val Leu
1               5                   10                  15

Ala Pro Arg Pro Pro Asp Asp Pro Gly Phe Gly Pro His Gln Arg Leu
            20                  25                  30

Glu Lys Leu Asp Ser Leu Leu Ser Asp Tyr Asp Ile Leu Ser Leu Ser
        35                  40                  45

Asn Ile Gln Gln His Ser Val Arg Lys Arg Asp Leu Gln Thr Ser Thr
50                  55                  60

His Val Glu Thr Leu Leu Thr Phe Ser Ala Leu Lys Arg His Phe Lys
65                  70                  75                  80

Leu Tyr Leu Thr Ser Ser Thr Glu Arg Phe Ser Gln Asn Phe Lys Val
                85                  90                  95

Val Val Val Asp Gly Lys Asn Glu Ser Glu Tyr Thr Val Lys Trp Gln
            100                 105                 110

Asp Phe Phe Thr Gly His Val Val Gly Glu Pro Asp Ser Arg Val Leu
        115                 120                 125

Ala His Ile Arg Asp Asp Asp Val Ile Ile Arg Ile Asn Thr Asp Gly
130                 135                 140

Ala Glu Tyr Asn Ile Glu Pro Leu Trp Arg Phe Val Asn Asp Thr Lys
145                 150                 155                 160

Asp Lys Arg Met Leu Val Tyr Lys Ser Glu Asp Ile Lys Asn Val Ser
                165                 170                 175

Arg Leu Gln Ser Pro Lys Val Cys Gly Tyr Leu Lys Val Asp Asn Glu
            180                 185                 190

Glu Leu Leu Pro Lys Gly Leu Val Asp Arg Glu Pro Glu Glu Leu
        195                 200                 205

Val His Arg Val Lys Arg Arg Ala Asp Pro Asp Pro Met Lys Asn Thr
210                 215                 220

Cys Lys Leu Leu Val Val Ala Asp His Arg Phe Tyr Arg Tyr Met Gly
225                 230                 235                 240

Arg Gly Glu Glu Ser Thr Thr Thr Asn Tyr Leu Ile Glu Leu Ile Asp
                245                 250                 255

Arg Val Asp Asp Ile Tyr Arg Asn Thr Ser Trp Asp Asn Ala Gly Phe
            260                 265                 270

Lys Gly Tyr Gly Ile Gln Ile Glu Gln Ile Arg Ile Leu Lys Ser Pro
        275                 280                 285
```

```
Gln Glu Val Lys Pro Gly Glu Lys His Tyr Asn Met Ala Lys Ser Tyr
    290                 295                 300
Pro Asn Glu Glu Lys Asp Ala Trp Asp Val Lys Met Leu Leu Glu Gln
305                 310                 315                 320
Phe Ser Phe Asp Ile Ala Glu Glu Ala Ser Lys Val Cys Leu Ala His
                325                 330                 335
Leu Phe Thr Tyr Gln Asp Phe Asp Met Gly Thr Leu Gly Leu Ala Tyr
                340                 345                 350
Val Gly Ser Pro Arg Ala Asn Ser His Gly Val Cys Pro Lys Ala
            355                 360                 365
Tyr Tyr Ser Pro Val Gly Lys Lys Asn Ile Tyr Leu Asn Ser Gly Leu
370                 375                 380
Thr Ser Thr Lys Asn Tyr Gly Lys Thr Ile Leu Thr Lys Glu Ala Asp
385                 390                 395                 400
Leu Val Thr Thr His Glu Leu Gly His Asn Phe Gly Ala Glu His Asp
                    405                 410                 415
Pro Asp Gly Leu Ala Glu Cys Ala Pro Asn Glu Asp Gln Gly Gly Lys
                420                 425                 430
Tyr Val Met Tyr Pro Ile Ala Val Ser Gly Asp His Glu Asn Asn Lys
            435                 440                 445
Met Phe Ser Asn Cys Ser Lys Gln Ser Ile Tyr Lys Thr Ile Glu Ser
450                 455                 460
Lys Ala Gln Glu Cys Phe Gln Glu Arg Ser Asn Lys Val Cys Gly Asn
465                 470                 475                 480
Ser Arg Val Asp Glu Gly Glu Cys Asp Pro Gly Ile Met Tyr Leu
                485                 490                 495
Asn Asn Asp Thr Cys Cys Asn Ser Asp Cys Thr Leu Lys Glu Gly Val
                500                 505                 510
Gln Cys Ser Asp Arg Asn Ser Pro Cys Cys Lys Asn Cys Gln Phe Glu
            515                 520                 525
Thr Ala Gln Lys Lys Cys Gln Glu Ala Ile Asn Ala Thr Cys Lys Gly
                530                 535                 540
Val Ser Tyr Cys Thr Gly Asn Ser Ser Glu Cys Pro Pro Gly Asn
545                 550                 555                 560
Ala Glu Asp Asp Thr Val Cys Leu Asp Leu Gly Lys Cys Lys Asp Gly
                565                 570                 575
Lys Cys Ile Pro Phe Cys Glu Arg Glu Gln Gln Leu Glu Ser Cys Ala
                580                 585                 590
Cys Asn Glu Thr Asp Asn Ser Cys Lys Val Cys Cys Arg Asp Leu Ser
        595                 600                 605
Gly Arg Cys Val Pro Tyr Val Asp Ala Glu Gln Lys Asn Leu Phe Leu
        610                 615                 620
Arg Lys Gly Lys Pro Cys Thr Val Gly Phe Cys Asp Met Asn Gly Lys
625                 630                 635                 640
Cys Glu Lys Arg Val Gln Asp Val Ile Glu Arg Phe Trp Asp Phe Ile
                645                 650                 655
Asp Gln Leu Ser Ile Asn Thr Phe Gly Lys Phe Leu Ala Asp Asn Ile
                660                 665                 670
Val Gly Ser Val Leu Val Phe Ser Leu Ile Phe Trp Ile Pro Phe Ser
            675                 680                 685
Ile Leu Val His Cys Val Asp Lys Lys Leu Asp Lys Gln Tyr Glu Ser
            690                 695                 700
Leu Ser Leu Phe His Pro Ser Asn Val Glu Met Leu Ser Ser Met Asp
```

```
                705                 710                 715                 720
Ser Ala Ser Val Arg Ile Ile Lys Pro Phe Pro Ala Pro Gln Xaa Pro
                    725                 730                 735

Gly Arg Leu Gln Pro Ala Pro Val Ile Pro Ser Ala Pro Ala Ala Pro
                    740                 745                 750

Lys Leu Asp His Gln Arg Met Asp Thr Ile Gln Glu Asp Pro Ser Thr
                    755                 760                 765

Asp Ser His Met Asp Glu Asp Gly Phe Glu Lys Asp Pro Phe Pro Asn
                    770                 775                 780

Ser Ser Thr Ala Ala Lys Ser Phe Glu Asp Leu Thr Asp His Pro Val
785                 790                 795                 800

Thr Arg Ser Glu Lys Ala Ala Ser Phe Lys Leu Gln Arg Gln Asn Arg
                    805                 810                 815

Val Asp Ser Lys Glu Thr Glu Cys
                    820

<210> SEQ ID NO 25
<211> LENGTH: 1581
<212> TYPE: PRT
<213> ORGANISM: Homo sapiens
<220> FEATURE:
<221> NAME/KEY: misc_feature
<222> LOCATION: (1032)..(1032)
<223> OTHER INFORMATION: Xaa can be any naturally occurring amino acid
<220> FEATURE:
<221> NAME/KEY: misc_feature
<222> LOCATION: (1457)..(1457)
<223> OTHER INFORMATION: Xaa can be any naturally occurring amino acid

<400> SEQUENCE: 25

Met Lys Ala Gln Gly Glu Thr Glu Glu Ser Glu Lys Leu Ser Lys Met
1               5                   10                  15

Ser Ser Leu Leu Glu Arg Leu His Ala Lys Phe Asn Gln Asn Arg Pro
                20                  25                  30

Trp Ser Glu Thr Ile Lys Leu Val Arg Gln Val Met Glu Lys Arg Val
            35                  40                  45

Val Met Ser Ser Gly Gly His Gln His Leu Val Ser Cys Leu Glu Thr
    50                  55                  60

Leu Gln Lys Ala Leu Lys Val Thr Ser Leu Pro Ala Met Thr Asp Arg
65                  70                  75                  80

Leu Glu Ser Ile Ala Arg Gln Asn Gly Leu Gly Ser His Leu Ser Ala
                85                  90                  95

Ser Gly Thr Glu Cys Tyr Ile Thr Ser Asp Met Phe Tyr Val Glu Val
            100                 105                 110

Gln Leu Asp Pro Ala Gly Gln Leu Cys Asp Val Lys Val Ala His His
        115                 120                 125

Gly Glu Asn Pro Val Ser Cys Pro Glu Leu Val Gln Gln Leu Arg Glu
    130                 135                 140

Lys Asn Phe Asp Glu Phe Ser Lys His Leu Lys Gly Leu Val Asn Leu
145                 150                 155                 160

Tyr Asn Leu Pro Gly Asp Asn Lys Leu Lys Thr Lys Met Tyr Leu Ala
                165                 170                 175

Leu Gln Ser Leu Glu Gln Asp Leu Ser Lys Met Ala Ile Met Tyr Trp
            180                 185                 190

Lys Ala Thr Asn Ala Gly Pro Leu Asp Lys Ile Leu His Gly Ser Val
        195                 200                 205

Gly Tyr Leu Thr Pro Arg Ser Gly Gly His Leu Met Asn Leu Lys Tyr
    210                 215                 220
```

```
Tyr Val Ser Pro Ser Asp Leu Leu Asp Asp Lys Thr Ala Ser Pro Ile
225                 230                 235                 240

Ile Leu His Glu Asn Asn Val Ser Arg Ser Leu Gly Met Asn Ala Ser
            245                 250                 255

Val Thr Ile Glu Gly Thr Ser Ala Val Tyr Lys Leu Pro Ile Ala Pro
        260                 265                 270

Leu Ile Met Gly Ser His Pro Val Asp Asn Lys Trp Thr Pro Ser Phe
    275                 280                 285

Ser Ser Ile Thr Ser Ala Asn Ser Val Asp Leu Pro Ala Cys Phe Phe
290                 295                 300

Leu Lys Phe Pro Gln Pro Ile Pro Val Ser Arg Ala Phe Val Gln Lys
305                 310                 315                 320

Leu Gln Asn Cys Thr Gly Ile Pro Leu Phe Glu Thr Gln Pro Thr Tyr
            325                 330                 335

Ala Pro Leu Tyr Glu Leu Ile Thr Gln Phe Glu Leu Ser Lys Asp Pro
        340                 345                 350

Asp Pro Ile Pro Leu Asn His Asn Met Arg Phe Tyr Ala Ala Leu Pro
    355                 360                 365

Gly Gln Gln His Cys Tyr Phe Leu Asn Lys Asp Ala Pro Leu Pro Asp
370                 375                 380

Gly Arg Ser Leu Gln Gly Thr Leu Val Ser Lys Ile Thr Phe Gln His
385                 390                 395                 400

Pro Gly Arg Val Pro Leu Ile Leu Asn Leu Ile Arg His Gln Val Ala
            405                 410                 415

Tyr Asn Thr Leu Ile Gly Ser Cys Val Lys Arg Thr Ile Leu Lys Glu
        420                 425                 430

Asp Ser Pro Gly Leu Leu Gln Phe Glu Val Cys Pro Leu Ser Glu Ser
    435                 440                 445

Arg Phe Ser Val Ser Phe Gln His Pro Val Asn Asp Ser Leu Val Cys
450                 455                 460

Val Val Met Asp Val Gln Asp Ser Thr His Val Ser Cys Lys Leu Tyr
465                 470                 475                 480

Lys Gly Leu Ser Asp Ala Leu Ile Cys Thr Asp Asp Phe Ile Ala Lys
            485                 490                 495

Val Val Gln Arg Cys Met Ser Ile Pro Val Thr Met Arg Ala Ile Arg
        500                 505                 510

Arg Lys Ala Glu Thr Ile Gln Ala Asp Thr Pro Ala Leu Ser Leu Ile
    515                 520                 525

Ala Glu Thr Val Glu Asp Met Val Lys Lys Asn Leu Pro Pro Ala Ser
530                 535                 540

Ser Pro Gly Tyr Gly Met Thr Thr Gly Asn Asn Pro Met Ser Gly Thr
545                 550                 555                 560

Thr Thr Ser Thr Asn Thr Phe Pro Gly Gly Pro Ile Ala Thr Leu Phe
            565                 570                 575

Asn Met Ser Met Ser Ile Lys Asp Arg His Glu Ser Val Gly His Gly
        580                 585                 590

Glu Asp Phe Ser Lys Val Ser Gln Asn Pro Ile Leu Thr Ser Leu Leu
    595                 600                 605

Gln Ile Thr Gly Asn Gly Gly Ser Thr Ile Gly Ser Ser Pro Thr Pro
610                 615                 620

Pro His His Thr Pro Pro Val Ser Ser Met Ala Gly Asn Thr Lys
625                 630                 635                 640

Asn His Pro Met Leu Met Asn Leu Leu Lys Asp Asn Pro Ala Gln Asp
```

-continued

```
                645                 650                 655
Phe Ser Thr Leu Tyr Gly Ser Ser Pro Leu Glu Arg Gln Asn Ser Ser
                660                 665                 670

Ser Gly Ser Pro Arg Met Glu Ile Cys Ser Gly Ser Asn Lys Thr Lys
                675                 680                 685

Lys Lys Lys Ser Ser Arg Leu Pro Pro Glu Lys Pro Lys His Gln Thr
                690                 695                 700

Glu Asp Asp Phe Gln Arg Glu Leu Phe Ser Met Asp Val Asp Ser Gln
705                 710                 715                 720

Asn Pro Ile Phe Asp Val Asn Met Thr Ala Asp Thr Leu Asp Thr Pro
                725                 730                 735

His Ile Thr Pro Ala Pro Ser Gln Cys Ser Thr Pro Pro Thr Thr Tyr
                740                 745                 750

Pro Gln Pro Val Pro His Pro Gln Pro Ser Ile Gln Arg Met Val Arg
                755                 760                 765

Leu Ser Ser Ser Asp Ser Ile Gly Pro Asp Val Thr Asp Ile Leu Ser
                770                 775                 780

Asp Ile Ala Glu Glu Ala Ser Lys Leu Pro Ser Thr Ser Asp Asp Cys
785                 790                 795                 800

Pro Ala Ile Gly Thr Pro Leu Arg Asp Ser Ser Ser Gly His Ser
                805                 810                 815

Gln Ser Thr Leu Phe Asp Ser Asp Val Phe Gln Thr Asn Asn Asn Glu
                820                 825                 830

Asn Pro Tyr Thr Asp Pro Ala Asp Leu Ile Ala Asp Ala Ala Gly Ser
                835                 840                 845

Pro Ser Ser Asp Ser Pro Thr Asn His Phe Phe His Asp Gly Val Asp
850                 855                 860

Phe Asn Pro Asp Leu Leu Asn Ser Gln Ser Gln Ser Gly Phe Gly Glu
865                 870                 875                 880

Glu Tyr Phe Asp Glu Ser Ser Gln Ser Gly Asp Asn Asp Phe Lys
                885                 890                 895

Gly Phe Ala Ser Gln Ala Leu Asn Thr Leu Gly Val Pro Met Leu Gly
                900                 905                 910

Gly Asp Asn Gly Glu Thr Lys Phe Lys Gly Asn Asn Gln Ala Asp Thr
                915                 920                 925

Val Asp Phe Ser Ile Ile Ser Val Ala Gly Lys Ala Leu Ala Pro Ala
                930                 935                 940

Asp Leu Met Glu His His Ser Gly Ser Gln Gly Pro Leu Leu Thr Thr
945                 950                 955                 960

Gly Asp Leu Gly Lys Glu Lys Thr Gln Lys Arg Val Lys Glu Gly Asn
                965                 970                 975

Gly Thr Ser Asn Ser Thr Leu Ser Gly Pro Gly Leu Asp Ser Lys Pro
                980                 985                 990

Gly Lys Arg Ser Arg Thr Pro Ser  Asn Asp Gly Lys Ser  Lys Asp Lys
                995                 1000                1005

Pro Pro Lys Arg Lys Lys Ala  Asp Thr Glu Gly Lys  Ser Pro Ser
      1010                1015                1020

His Ser  Ser Ser Asn Arg Pro  Phe Xaa Pro Pro Thr  Ser Thr Gly
      1025                1030                1035

Gly Ser  Lys Ser Pro Gly Ser  Ala Gly Arg Ser Gln  Thr Pro Pro
      1040                1045                1050

Gly Val  Ala Thr Pro Pro Ile  Pro Lys Ile Thr Ile  Gln Ile Pro
      1055                1060                1065
```

-continued

```
Lys Gly Thr Val Met Val Gly Lys Pro Ser Ser His Ser Gln Tyr
    1070            1075            1080

Thr Ser Ser Gly Ser Val Ser Ser Ser Gly Ser Lys Ser His His
    1085            1090            1095

Ser His Ser Ser Ser Ser Ser Ser Ala Ser Thr Ser Gly Lys
    1100            1105            1110

Met Lys Ser Ser Lys Ser Glu Gly Ser Ser Ser Lys Leu Ser
    1115            1120            1125

Ser Ser Met Tyr Ser Ser Gln Gly Ser Ser Gly Ser Ser Gln Ser
    1130            1135            1140

Lys Asn Ser Ser Gln Ser Gly Gly Lys Pro Gly Ser Ser Pro Ile
    1145            1150            1155

Thr Lys His Gly Leu Ser Ser Gly Ser Ser Thr Lys Met Lys
    1160            1165            1170

Pro Gln Gly Lys Pro Ser Ser Leu Met Asn Pro Ser Leu Ser Lys
    1175            1180            1185

Pro Asn Ile Ser Pro Ser His Ser Arg Pro Pro Gly Gly Ser Asp
    1190            1195            1200

Lys Leu Ala Ser Pro Met Lys Pro Val Pro Gly Thr Pro Pro Ser
    1205            1210            1215

Ser Lys Ala Lys Ser Pro Ile Ser Ser Gly Ser Gly Gly Ser His
    1220            1225            1230

Met Ser Gly Thr Ser Ser Ser Gly Met Lys Ser Ser Ser Gly
    1235            1240            1245

Leu Gly Ser Ser Gly Ser Leu Ser Gln Lys Thr Pro Pro Ser Ser
    1250            1255            1260

Asn Ser Cys Thr Ala Ser Ser Ser Ser Phe Ser Ser Gly Ser
    1265            1270            1275

Ser Met Ser Ser Ser Gln Asn Gln His Gly Ser Ser Lys Gly Lys
    1280            1285            1290

Ser Pro Ser Arg Asn Lys Lys Pro Ser Leu Thr Ala Val Ile Asp
    1295            1300            1305

Lys Leu Lys His Gly Val Val Thr Ser Gly Pro Gly Gly Glu Asp
    1310            1315            1320

Pro Leu Asp Gly Gln Met Gly Val Ser Thr Asn Ser Ser Ser His
    1325            1330            1335

Pro Met Ser Ser Lys His Asn Met Ser Gly Gly Glu Phe Gln Gly
    1340            1345            1350

Lys Arg Glu Lys Ser Asp Lys Asp Lys Ser Lys Val Ser Thr Ser
    1355            1360            1365

Gly Ser Ser Val Asp Ser Ser Lys Lys Thr Ser Glu Ser Lys Asn
    1370            1375            1380

Val Gly Ser Thr Gly Val Ala Lys Ile Ile Ile Ser Lys His Asp
    1385            1390            1395

Gly Gly Ser Pro Ser Ile Lys Ala Lys Val Thr Leu Gln Lys Pro
    1400            1405            1410

Gly Glu Ser Ser Gly Glu Gly Leu Arg Pro Gln Met Ala Ser Ser
    1415            1420            1425

Lys Asn Tyr Gly Ser Pro Leu Ile Ser Gly Ser Thr Pro Lys His
    1430            1435            1440

Glu Arg Gly Ser Pro Ser His Ser Lys Ser Pro Ala Tyr Xaa Pro
    1445            1450            1455

Gln Asn Leu Asp Ser Glu Ser Glu Ser Gly Ser Ser Ile Ala Glu
    1460            1465            1470
```

```
Lys Ser Tyr Gln Asn Ser Pro Ser Ser Asp Asp Gly Ile Arg Pro
    1475                1480                1485

Leu Pro Glu Tyr Ser Thr Glu Lys His Lys Lys His Lys Lys Glu
    1490                1495                1500

Lys Lys Lys Val Lys Asp Lys Asp Arg Asp Arg Asp Arg Asp Lys
    1505                1510                1515

Asp Arg Asp Lys Lys Ser His Ser Ile Lys Pro Glu Ser Trp
    1520                1525                1530

Ser Lys Ser Pro Ile Ser Ser Asp Gln Ser Leu Ser Met Thr Ser
1535                1540                1545

Asn Thr Ile Leu Ser Ala Asp Arg Pro Ser Arg Leu Ser Pro Asp
    1550                1555                1560

Phe Met Ile Gly Glu Glu Asp Asp Asp Leu Met Asp Val Ala Leu
    1565                1570                1575

Ile Gly Asn
    1580

<210> SEQ ID NO 26
<211> LENGTH: 372
<212> TYPE: PRT
<213> ORGANISM: mouse
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid

<400> SEQUENCE: 26

Met Ser Met Ser Pro Lys His Thr Thr Pro Phe Ser Val Ser Asp Ile
1               5                   10                  15

Leu Xaa Pro Leu Glu Glu Ser Tyr Lys Lys Val Gly Met Glu Gly Gly
            20                  25                  30

Gly Leu Gly Ala Pro Leu Ala Ala Tyr Arg Gln Gly Gln Ala Ala Pro
        35                  40                  45

Pro Ala Ala Ala Met Gln Gln His Ala Val Gly His His Gly Ala Val
    50                  55                  60

Thr Ala Ala Tyr His Met Thr Ala Ala Gly Val Pro Gln Leu Ser His
65                  70                  75                  80

Ser Ala Val Gly Gly Tyr Cys Asn Gly Asn Leu Gly Asn Met Ser Glu
                85                  90                  95

Leu Pro Pro Tyr Gln Asp Thr Met Arg Asn Ser Ala Ser Gly Pro Gly
            100                 105                 110

Trp Tyr Gly Ala Asn Pro Asp Pro Arg Phe Pro Ala Ile Ser Arg Phe
        115                 120                 125

Met Gly Pro Ala Ser Gly Met Asn Met Ser Gly Met Gly Gly Leu Gly
    130                 135                 140

Ser Leu Gly Asp Val Ser Lys Asn Met Ala Pro Leu Pro Ser Ala Pro
145                 150                 155                 160

Arg Arg Lys Arg Arg Val Leu Phe Ser Gln Ala Gln Val Tyr Glu Leu
                165                 170                 175

Glu Arg Arg Phe Lys Gln Gln Lys Tyr Leu Ser Ala Pro Glu Arg Glu
            180                 185                 190
```

```
His Leu Ala Ser Met Ile His Leu Thr Pro Thr Gln Val Lys Ile Trp
            195                 200                 205

Phe Gln Asn His Arg Tyr Lys Met Lys Arg Gln Ala Lys Asp Lys Ala
        210                 215                 220

Ala Gln Gln Gln Leu Gln Gln Asp Ser Gly Gly Gly Gly Gly Gly Gly
225                 230                 235                 240

Gly Gly Ala Gly Cys Pro Gln Gln Gln Ala Gln Gln Ser Pro
                245                 250                 255

Arg Arg Val Ala Val Pro Val Leu Val Lys Asp Gly Lys Pro Cys Gln
            260                 265                 270

Ala Gly Ala Pro Ala Pro Gly Ala Ala Ser Leu Gln Ser His Ala Gln
        275                 280                 285

Gln Gln Ala Gln Gln Ala Gln Ala Ala Gln Ala Ala Ala Ala
                290                 295                 300

Ile Ser Val Gly Ser Gly Gly Ala Val Leu Gly Ala His Pro Gly His
305                 310                 315                 320

Gln Pro Gly Ser Ala Gly Gln Xaa Pro Asp Leu Ala His His Ala Ala
            325                 330                 335

Xaa Pro Ala Gly Leu Gln Gly Gln Val Ser Ser Leu Ser His Leu Asn
        340                 345                 350

Ser Ser Gly Ser Asp Tyr Gly Ala Met Ser Cys Ser Thr Leu Leu Tyr
            355                 360                 365

Gly Arg Thr Trp
    370

<210> SEQ ID NO 27
<211> LENGTH: 498
<212> TYPE: PRT
<213> ORGANISM: rat
<220> FEATURE:
<221> NAME/KEY: misc_feature
<222> LOCATION: (31)..(31)
<223> OTHER INFORMATION: Xaa can be any naturally occurring amino acid

<400> SEQUENCE: 27

Met Pro Thr Pro Ser Ala Pro Ser Pro Gln Pro Lys Gly Phe Arg Arg
1               5                   10                  15

Ala Val Ser Glu Gln Asp Ala Lys Gln Ala Glu Ala Val Thr Xaa Pro
            20                  25                  30

Arg Phe Ile Gly Arg Arg Gln Ser Leu Ile Glu Asp Ala Arg Lys Glu
        35                  40                  45

Arg Glu Ala Ala Ala Ala Ala Ala Ala Val Ala Ser Ser Glu
    50                  55                  60

Pro Gly Asn Pro Leu Glu Ala Val Val Phe Glu Arg Asp Gly Asn
65                  70                  75                  80

Ala Val Leu Asn Leu Leu Phe Ser Leu Arg Gly Thr Lys Pro Ser Ser
            85                  90                  95

Leu Ser Arg Ala Val Lys Val Phe Glu Thr Phe Glu Ala Lys Ile His
        100                 105                 110

His Leu Glu Thr Arg Pro Ala Gln Arg Pro Leu Ala Gly Ser Pro His
    115                 120                 125

Leu Glu Tyr Phe Val Arg Phe Glu Val Pro Ser Gly Asp Leu Ala Ala
            130                 135                 140

Leu Leu Ser Ser Val Arg Arg Val Ser Asp Asp Val Arg Ser Ala Arg
145                 150                 155                 160

Glu Asp Lys Val Pro Trp Phe Pro Arg Lys Val Ser Glu Leu Asp Lys
```

```
            165                 170                 175
Cys His His Leu Val Thr Lys Phe Asp Pro Asp Leu Asp Leu Asp His
        180                 185                 190

Pro Gly Phe Ser Asp Gln Val Tyr Arg Gln Arg Arg Lys Leu Ile Ala
        195                 200                 205

Glu Ile Ala Phe Gln Tyr Lys His Gly Glu Pro Ile Pro His Val Glu
    210                 215                 220

Tyr Thr Ala Glu Glu Ile Ala Thr Trp Lys Val Tyr Val Thr Leu
225                 230                 235                 240

Lys Gly Leu Tyr Ala Thr His Ala Cys Arg Glu His Leu Glu Gly Phe
                245                 250                 255

Gln Leu Leu Glu Arg Tyr Cys Gly Tyr Arg Glu Asp Ser Ile Pro Gln
            260                 265                 270

Leu Glu Asp Val Ser Arg Phe Leu Lys Glu Arg Thr Gly Phe Gln Leu
        275                 280                 285

Arg Pro Val Ala Gly Leu Leu Ser Ala Arg Asp Phe Leu Ala Ser Leu
        290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
            340                 345                 350

Gly Leu Ala Ser Leu Gly Ala Ser Asp Glu Glu Ile Glu Lys Leu Ser
        355                 360                 365

Thr Val Tyr Trp Phe Thr Val Glu Phe Gly Leu Cys Lys Gln Asn Gly
        370                 375                 380

Glu Leu Lys Ala Tyr Gly Ala Gly Leu Leu Ser Ser Tyr Gly Glu Leu
385                 390                 395                 400

Leu His Ser Leu Ser Glu Pro Glu Val Arg Ala Phe Asp Pro Asp
                405                 410                 415

Thr Ala Ala Val Gln Pro Tyr Gln Asp Gln Thr Tyr Gln Pro Val Tyr
                420                 425                 430

Phe Val Ser Glu Ser Phe Asn Asp Ala Lys Asp Lys Leu Arg Asn Tyr
            435                 440                 445

Ala Ser Arg Ile Gln Arg Pro Phe Ser Val Lys Phe Asp Pro Tyr Thr
        450                 455                 460

Leu Ala Ile Asp Val Leu Asp Ser Pro His Thr Ile Gln Arg Ser Leu
465                 470                 475                 480

Glu Gly Val Gln Asp Glu Leu His Thr Leu Ala His Ala Leu Ser Ala
                485                 490                 495

Ile Ser

<210> SEQ ID NO 28
<211> LENGTH: 9
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 28

Thr Gly Pro Leu Xaa Pro Gly Pro Phe
1               5
```

```
<210> SEQ ID NO 29
<211> LENGTH: 16
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 29

Tyr Ser Pro Thr Xaa Pro Thr Tyr Ser Pro Thr Xaa Pro Lys Lys Lys
1               5                   10                  15

<210> SEQ ID NO 30
<211> LENGTH: 9
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 30

Ala Pro Arg Xaa Pro Gly Gly Arg Arg
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 31

Arg Arg Pro Arg Xaa Pro Ala Lys Leu Ser Phe Phe Phe Pro Ser
1               5                   10                  15

<210> SEQ ID NO 32
<211> LENGTH: 9
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 32

Pro Pro Leu Met Xaa Pro Pro Phe Tyr
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic kinase active site blocker peptide
```

```
<220> FEATURE:
<221> NAME/KEY: misc_feature
<222> LOCATION: (8)..(8)
<223> OTHER INFORMATION: Xaa can be any naturally occurring amino acid

<400> SEQUENCE: 33

Lys Gln Ala Glu Ala Val Thr Xaa Pro Arg
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 34

Lys Asn Ile Val Thr Pro Arg Xaa Pro Pro Pro Ser Gln Gly Lys
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 35

Thr Leu Ser Pro Ile Ala Pro Arg Xaa Pro Ala Lys Leu Ser Phe Gln
1               5                   10                  15

Phe Pro Ser Ser
            20

<210> SEQ ID NO 36
<211> LENGTH: 21
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 36

Lys Arg Glu Leu Val Glu Pro Leu Xaa Pro Ser Gly Glu Ala Pro Asn
1               5                   10                  15

Gln Ala Leu Leu Arg
            20

<210> SEQ ID NO 37
<211> LENGTH: 16
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
```

```
<222> LOCATION: (12)..(12)
<223> OTHER INFORMATION: Xaa can be any naturally occurring amino acid

<400> SEQUENCE: 37

Tyr Ser Pro Thr Xaa Pro Thr Tyr Ser Pro Thr Xaa Pro Lys Lys Lys
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 38

Glu Glu Glu Asp Gly Thr Gly Xaa Pro Gln Leu Asn Asn Arg
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (14)..(14)
<223> OTHER INFORMATION: Xaa can be any naturally occurring amino acid

<400> SEQUENCE: 39

Met Lys Asp Asp Lys Glu Glu Glu Asp Gly Thr Gly Xaa Pro Gln
1               5                   10                  15

Leu Asn Asn Arg
            20

<210> SEQ ID NO 40
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 40

Phe Asn Glu Leu Ala Xaa Pro Phe Glu Asn Glu
1               5                   10

<210> SEQ ID NO 41
<211> LENGTH: 19
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (10)..(10)
<223> OTHER INFORMATION: Xaa can be any naturally occurring amino acid

<400> SEQUENCE: 41

Glu Val Gly Leu Phe Asn Glu Leu Ala Xaa Pro Phe Glu Asn Glu Phe
1               5                   10                  15

Lys Lys Ala
```

```
<210> SEQ ID NO 42
<211> LENGTH: 10
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 42

Val Asp Lys Val Thr Xaa Pro Thr Lys Val
1               5                   10

<210> SEQ ID NO 43
<211> LENGTH: 16
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (12)..(12)
<223> OTHER INFORMATION: Xaa can be any naturally occurring amino acid

<400> SEQUENCE: 43

Leu Trp Glu Lys Gln Ser Val Asp Lys Val Thr Xaa Pro Thr Lys Val
1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 44

Leu Tyr Arg Ser Pro Xaa Met Pro Glu Asn Leu
1               5                   10

<210> SEQ ID NO 45
<211> LENGTH: 19
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 45

Arg Ser Gly Leu Tyr Arg Ser Pro Xaa Met Pro Glu Asn Leu Asn Arg
1               5                   10                  15

Pro Arg Leu

<210> SEQ ID NO 46
<211> LENGTH: 10
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
```

```
<222> LOCATION: (5)..(5)
<223> OTHER INFORMATION: Xaa can be any naturally occurring amino acid

<400> SEQUENCE: 46

Pro Gly Pro Gly Xaa Pro Val Pro Thr Gly
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 47

Ser Thr Pro Gly Pro Gly Xaa Pro Val Pro Thr Gly Ser Val
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 48

Asp Leu Glu Leu Pro Leu Xaa Pro Ser Leu Leu Gly
1               5                   10

<210> SEQ ID NO 49
<211> LENGTH: 18
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 49

Arg Asp Leu Glu Leu Pro Leu Xaa Pro Ser Leu Leu Gly Gly Pro Gly
1               5                   10                  15

Pro Glu

<210> SEQ ID NO 50
<211> LENGTH: 13
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 50

Gly Pro Gly Pro Glu Arg Xaa Pro Gly Ser Gly Ser Gly
1               5                   10

<210> SEQ ID NO 51
```

<211> LENGTH: 20
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 51

Leu Gly Gly Pro Gly Pro Glu Arg Xaa Pro Gly Ser Gly Ser Gly Ser
1               5                   10                  15

Gly Leu Gln Ala
            20

<210> SEQ ID NO 52
<211> LENGTH: 13
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 52

Ser Thr Leu Xaa Pro Ile Ala Pro Arg Xaa Pro Ala Lys
1               5                   10

<210> SEQ ID NO 53
<211> LENGTH: 19
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 53

His Phe Trp Ser Thr Leu Xaa Pro Ile Ala Pro Arg Xaa Pro Ala Lys
1               5                   10                  15

Leu Ser Phe

<210> SEQ ID NO 54
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 54

Pro Val Val Leu Xaa Pro Gly Pro Gln Lys Pro
1               5                   10

```
<210> SEQ ID NO 55
<211> LENGTH: 14
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 55

Gly Leu Ser Thr Pro Val Val Leu Xaa Pro Gly Pro Gln Lys
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (10)..(10)
<223> OTHER INFORMATION: Xaa can be any naturally occurring amino acid

<400> SEQUENCE: 56

Tyr Leu Ala Leu Asp Phe Gln Pro Ser Xaa Pro Ser Pro His Arg Lys
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (12)..(12)
<223> OTHER INFORMATION: Xaa can be any naturally occurring amino acid

<400> SEQUENCE: 57

Val Asp Tyr Leu Ala Leu Asp Phe Gln Pro Ser Xaa Pro Ser Pro His
1               5                   10                  15

Arg Lys Pro

<210> SEQ ID NO 58
<211> LENGTH: 14
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 58

Met Thr Ile Leu Gln Ala Pro Xaa Pro Ala Pro Ser Thr Ile
1               5                   10

<210> SEQ ID NO 59
<211> LENGTH: 15
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid
```

<400> SEQUENCE: 59

Thr Ile Leu Gln Ala Pro Xaa Pro Ala Pro Ser Thr Ile Pro Gly
1               5                   10                  15

<210> SEQ ID NO 60
<211> LENGTH: 24
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 60

Ile Ser Ile Pro Xaa Pro Pro Val Thr Xaa Pro Glu Gly Asp Asp Arg
1               5                   10                  15

Pro Glu Xaa Pro Glu Tyr Ser Gly
            20

<210> SEQ ID NO 61
<211> LENGTH: 16
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 61

Glu Gly Asp Asp Arg Pro Glu Xaa Pro Glu Tyr Ser Gly Gly Asn Ile
1               5                   10                  15

<210> SEQ ID NO 62
<211> LENGTH: 13
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 62

Pro Pro Val Thr Xaa Pro Glu Gly Asp Asp Arg Pro Glu
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

```
<400> SEQUENCE: 63

Ala Ile Ile Ser Ile Pro Xaa Pro Pro Val Thr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 64

Phe Arg Gly Phe Xaa Phe Val Ala Thr Gly
1               5                   10

<210> SEQ ID NO 65
<211> LENGTH: 18
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 65

Ala His Gln Leu Phe Arg Gly Phe Xaa Phe Val Ala Thr Gly Leu Met
1               5                   10                  15

Glu Asp

<210> SEQ ID NO 66
<211> LENGTH: 18
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 66

Tyr Ala His Gln Gln Pro Pro Xaa Pro Leu Pro Val Tyr Ser Ser Ser
1               5                   10                  15

Ala Lys

<210> SEQ ID NO 67
<211> LENGTH: 13
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 67

Ala His Gln Gln Pro Pro Xaa Pro Leu Pro Val Tyr Ser
1               5                   10

<210> SEQ ID NO 68
<211> LENGTH: 14
```

```
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 68

Lys Ser Glu Pro Ser Xaa Pro Asp His Gly Ser Ser Ala Ile
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 69

Ser Glu Pro Ser Xaa Pro Asp His Gly Ser Ser Ala
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 70

Arg Gly Gly Ala Arg Ala Xaa Pro Ala Thr Gln Pro
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 71

Leu Pro Pro Ser Ala Xaa Gly Pro Asp Ala Thr Val Gly
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 72

Val Gly Gly Pro Ala Pro Xaa Pro Leu Leu Pro Pro Ser Ala
```

```
1               5                   10
```

<210> SEQ ID NO 73
<211> LENGTH: 40
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 73

```
Arg Gly Gly Ala Arg Ala Xaa Pro Ala Thr Gln Pro Pro Pro Leu Leu
1               5                   10                  15

Pro Pro Ser Ala Xaa Gly Pro Asp Ala Thr Val Gly Gly Pro Ala Pro
            20                  25                  30

Xaa Pro Leu Leu Pro Pro Ser Ala
        35                  40
```

<210> SEQ ID NO 74
<211> LENGTH: 14
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 74

```
Asn Thr Ile Asp Leu Pro Met Xaa Pro Arg Thr Leu Asp Ser
1               5                   10
```

<210> SEQ ID NO 75
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 75

```
Ile Asp Leu Pro Met Xaa Pro Arg Thr Leu Asp
1               5                   10
```

<210> SEQ ID NO 76
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 76

```
Phe Pro Ala Pro Gln Xaa Pro Gly Arg Leu Gln
1               5                   10
```

<210> SEQ ID NO 77
<211> LENGTH: 16
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 77

```
Lys Pro Phe Pro Ala Pro Gln Xaa Pro Gly Arg Leu Gln Pro Ala Pro
1               5                   10                  15
```

<210> SEQ ID NO 78
<211> LENGTH: 12
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 78

```
Ser Asn Arg Pro Phe Xaa Pro Pro Thr Ser Thr Gly
1               5                   10
```

<210> SEQ ID NO 79
<211> LENGTH: 18
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 79

```
His Ser Ser Ser Asn Arg Pro Phe Xaa Pro Pro Thr Ser Thr Gly Gly
1               5                   10                  15

Ser Lys
```

<210> SEQ ID NO 80
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 80

```
Lys Ser Pro Ala Tyr Xaa Pro Gln Asn Leu Asp
1               5                   10
```

<210> SEQ ID NO 81
<211> LENGTH: 15
<212> TYPE: PRT
<213> ORGANISM: Artificial Sequence
<220> FEATURE:

```
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 81

His Ser Lys Ser Pro Ala Tyr Xaa Pro Gln Asn Leu Asp Ser Glu
1               5                   10                  15

<210> SEQ ID NO 82
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 82

Val Ser Asp Ile Leu Xaa Pro Leu Glu Glu Ser
1               5                   10

<210> SEQ ID NO 83
<211> LENGTH: 15
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 83

Phe Ser Val Ser Asp Ile Leu Xaa Pro Leu Glu Glu Ser Tyr Lys
1               5                   10                  15

<210> SEQ ID NO 84
<211> LENGTH: 11
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 84

Gly Ser Ala Gly Gln Xaa Pro Asp Leu Ala His
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 85

Ala His His Ala Ala Xaa Pro Ala Gly Leu Gln Gly
1               5                   10
```

```
<210> SEQ ID NO 86
<211> LENGTH: 20
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 86

Gly Ser Ala Gly Gln Xaa Pro Asp Leu Ala His His Ala Ala Xaa Pro
1               5                   10                  15

Ala Gly Leu Gln
            20

<210> SEQ ID NO 87
<211> LENGTH: 10
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 87

Lys Gln Ala Glu Ala Val Thr Xaa Pro Arg
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 88

Lys Gln Ala Glu Ala Val Thr Xaa Pro Arg Phe Ile Gly Arg
1               5                   10

<210> SEQ ID NO 89
<211> LENGTH: 24
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 89

Ile Ser Ile Pro Xaa Pro Pro Val Thr Xaa Pro Glu Gly Asp Asp Arg
```

```
                    1               5                  10                  15
Pro Glu Xaa Pro Glu Tyr Ser Cys
                    20
```

<210> SEQ ID NO 90
<211> LENGTH: 34
<212> TYPE: PRT
<213> ORGANISM: Artificial Sequence
<220> FEATURE:
<223> OTHER INFORMATION: Synthetic kinase active site blocker peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 90

```
Thr Ile Leu Gln Ala Pro Xaa Pro Ala Pro Ser Thr Asn Pro Ala Cys
1               5                   10                  15

Thr Ile Val Ala Thr Ile Asn Ser Ile Thr Glu Asx Leu Cys Lys Glu
                20                  25                  30

Arg Ser
```

<210> SEQ ID NO 91
<211> LENGTH: 13
<212> TYPE: PRT
<213> ORGANISM: Artificial Sequence
<220> FEATURE:
<223> OTHER INFORMATION: Synthetic polypeptide inhibitors

<400> SEQUENCE: 91

```
Met Pro Lys Lys Lys Pro Thr Pro Ile Gln Leu Asn Pro
1               5                   10
```

<210> SEQ ID NO 92
<211> LENGTH: 21
<212> TYPE: PRT
<213> ORGANISM: Artificial Sequence
<220> FEATURE:
<223> OTHER INFORMATION: Synthetic polypeptide inhibitors

<400> SEQUENCE: 92

```
Phe Gln Arg Lys Thr Leu Gln Arg Arg Asn Leu Lys Gly Leu Asn Leu
1               5                   10                  15

Asn Leu His Pro Asp
                20
```

<210> SEQ ID NO 93
<211> LENGTH: 17
<212> TYPE: PRT
<213> ORGANISM: Artificial Sequence
<220> FEATURE:
<223> OTHER INFORMATION: Synthetic polypeptide inhibitors

<400> SEQUENCE: 93

```
Met Pro Lys Lys Lys Pro Thr Pro Ile Gln Leu Asn Pro Ala Pro Asp
1               5                   10                  15

Gly
```

<210> SEQ ID NO 94
<211> LENGTH: 20
<212> TYPE: PRT
<213> ORGANISM: Artificial Sequence
<220> FEATURE:
<223> OTHER INFORMATION: Synthetic polypeptide inhibitors

<400> SEQUENCE: 94

```
Met Leu Ala Arg Arg Lys Pro Val Leu Pro Ala Leu Thr Ile Asn Pro
1               5                   10                  15

Thr Ile Ala Glu
            20

<210> SEQ ID NO 95
<211> LENGTH: 30
<212> TYPE: PRT
<213> ORGANISM: Artificial Sequence
<220> FEATURE:
<223> OTHER INFORMATION: Synthetic polypeptide inhibitors

<400> SEQUENCE: 95

Arg Gln Ile Lys Ile Trp Phe Gln Asn Arg Arg Met Lys Trp Lys Lys
1               5                   10                  15

Gly Met Pro Lys Lys Pro Thr Pro Ile Gln Leu Asn Pro
            20                  25                  30

<210> SEQ ID NO 96
<211> LENGTH: 43
<212> TYPE: PRT
<213> ORGANISM: Artificial Sequence
<220> FEATURE:
<223> OTHER INFORMATION: Synthetic polypeptide inhibitors

<400> SEQUENCE: 96

Gly Tyr Gly Arg Lys Lys Arg Arg Gln Arg Arg Gly Met Pro Lys
1               5                   10                  15

Lys Lys Pro Thr Pro Ile Gln Leu Asn Pro Asp Cys Lys Ile Asn Gly
            20                  25                  30

Ser Ile Thr Glu Asx Leu Cys Lys Glu Arg Ser
            35                  40

<210> SEQ ID NO 97
<211> LENGTH: 11
<212> TYPE: PRT
<213> ORGANISM: Artificial Sequence
<220> FEATURE:
<223> OTHER INFORMATION: Synthetic polypeptide inhibitors

<400> SEQUENCE: 97

Lys Gly Arg Lys Pro Arg Asp Leu Glu Leu Pro
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Synthetic polypeptide inhibitors

<400> SEQUENCE: 98

Pro Gln Lys Gly Arg Lys Pro Arg Asp Leu Glu Leu Pro Leu
1               5                   10

<210> SEQ ID NO 99
<211> LENGTH: 21
<212> TYPE: PRT
<213> ORGANISM: Artificial Sequence
<220> FEATURE:
<223> OTHER INFORMATION: Synthetic polypeptide inhibitors

<400> SEQUENCE: 99

Ile Asn Val Ala Ile Pro Gly Ile Met Leu Arg Arg Leu Gln Lys Gly
1               5                   10                  15
```

Asn Leu Pro Val Arg
        20

<210> SEQ ID NO 100
<211> LENGTH: 20
<212> TYPE: PRT
<213> ORGANISM: Artificial Sequence
<220> FEATURE:
<223> OTHER INFORMATION: Synthetic polypeptide inhibitors

<400> SEQUENCE: 100

Leu Lys Pro Ile Glu Ser Ser Ile Leu Ala Gln Arg Arg Val Arg Lys
1               5                   10                  15

Leu Pro Ser Thr
        20

<210> SEQ ID NO 101
<211> LENGTH: 21
<212> TYPE: PRT
<213> ORGANISM: Artificial Sequence
<220> FEATURE:
<223> OTHER INFORMATION: Synthetic polypeptide inhibitors

<400> SEQUENCE: 101

Leu Ser Pro Pro Ser Gln Ser Lys Leu Ala Gln Arg Arg Gln Arg Ala
1               5                   10                  15

Ser Leu Ser Ala Thr
        20

<210> SEQ ID NO 102
<211> LENGTH: 15
<212> TYPE: PRT
<213> ORGANISM: Artificial Sequence
<220> FEATURE:
<223> OTHER INFORMATION: Synthetic polypeptide inhibitors

<400> SEQUENCE: 102

Arg Arg Pro Arg Ser Pro Ala Lys Leu Ser Phe Gln Phe Ala Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic polypeptide inhibitors

<400> SEQUENCE: 103

Arg Arg Pro Arg Ser Pro Ala Lys Leu Ser Phe Phe Phe Pro Ser
1               5                   10                  15

<210> SEQ ID NO 104
<211> LENGTH: 20
<212> TYPE: PRT
<213> ORGANISM: Artificial Sequence
<220> FEATURE:
<223> OTHER INFORMATION: Synthetic polypeptide inhibitors

<400> SEQUENCE: 104

Thr Leu Ser Pro Ile Ala Pro Arg Ser Pro Ala Lys Leu Ser Phe Gln
1               5                   10                  15

Phe Pro Ser Ser
        20

<210> SEQ ID NO 105

```
<211> LENGTH: 14
<212> TYPE: PRT
<213> ORGANISM: Artificial Sequence
<220> FEATURE:
<223> OTHER INFORMATION: Synthetic polypeptide inhibitors

<400> SEQUENCE: 105

Thr Pro Ala Thr Pro Thr Ser Gln Phe Val Phe Ser Phe Pro
1               5                   10

<210> SEQ ID NO 106
<211> LENGTH: 15
<212> TYPE: PRT
<213> ORGANISM: Artificial Sequence
<220> FEATURE:
<223> OTHER INFORMATION: Synthetic polypeptide inhibitors

<400> SEQUENCE: 106

Ser Pro Ala Arg Leu Gln Gly Ala Asn Thr Leu Phe Gln Phe Pro
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic polypeptide inhibitors

<400> SEQUENCE: 107

Thr Pro Thr Ala Ala His Ser Gly Ser His Leu Phe Gly Phe Pro
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic polypeptide inhibitors

<400> SEQUENCE: 108

Arg Arg Pro Arg Ser Pro Ala Lys Leu Ser Phe Ala Phe Pro Ser
1               5                   10                  15

<210> SEQ ID NO 109
<211> LENGTH: 4
<212> TYPE: PRT
<213> ORGANISM: Artificial
<220> FEATURE:
<223> OTHER INFORMATION: Synthetic peptide

<400> SEQUENCE: 109

Ala Ala Ala Ala
1

<210> SEQ ID NO 110
<211> LENGTH: 4
<212> TYPE: PRT
<213> ORGANISM: Artificial
<220> FEATURE:
<223> OTHER INFORMATION: Synthetic peptide

<400> SEQUENCE: 110

Gly Ala Gly Ala
1

<210> SEQ ID NO 111
<211> LENGTH: 4
<212> TYPE: PRT
```

```
<213> ORGANISM: Artificial
<220> FEATURE:
<223> OTHER INFORMATION: Synthetic peptide

<400> SEQUENCE: 111

Gly Gly Gly Gly
1

<210> SEQ ID NO 112
<211> LENGTH: 4
<212> TYPE: PRT
<213> ORGANISM: Artificial
<220> FEATURE:
<223> OTHER INFORMATION: Synthetic peptide

<400> SEQUENCE: 112

Ala Gly Ala Gly
1

<210> SEQ ID NO 113
<211> LENGTH: 7
<212> TYPE: PRT
<213> ORGANISM: Artificial
<220> FEATURE:
<223> OTHER INFORMATION: Synthetic peptide

<400> SEQUENCE: 113

Ala Gly Pro Gly Ala Glu Phe
1               5

<210> SEQ ID NO 114
<211> LENGTH: 4
<212> TYPE: PRT
<213> ORGANISM: Artificial
<220> FEATURE:
<223> OTHER INFORMATION: Synthetic peptide

<400> SEQUENCE: 114

Ala Ala Gly Gly
1

<210> SEQ ID NO 115
<211> LENGTH: 4
<212> TYPE: PRT
<213> ORGANISM: Artificial
<220> FEATURE:
<223> OTHER INFORMATION: Synthetic peptide

<400> SEQUENCE: 115

Gly Gly Ala Ala
1
```

EXTRACELLULAR-SIGNAL-REGULATED-KINASE (ERK) HETEROPOLYLIGAND POLYPEPTIDE

This application claims benefit of priority to provisional application 60/865,589 filed 13 Nov. 2006.

REFERENCE TO SEQUENCE LISTING SUBMITTED ELECTRONICALLY VIA EFS-WEB

This application includes a "sequencelisting ascii.txt", 142 KB, created on Aug. 17, 2011, and submitted electronically via EFS-Web, which is hereby incorporated by reference in its entirety.

FIELD OF INVENTION

The invention relates to mammalian kinase ligands, substrates and modulators. In particular, the invention relates to polypeptides, polypeptide compositions and polynucleotides that encode polypeptides that are ligands, substrates, and/or modulators of ERK. The invention also relates to polyligands that are homopolyligands or heteropolyligands that modulate ERK activity. The invention also relates to ligands and polyligands tethered to a subcellular location.

This application has subject matter related to application Ser. Nos. 10/724,532 (now U.S. Pat. No. 7,071,295), 10/682,764 (US2004/0185556, PCT/US2004/013517, WO2005/040336), 11/233,246, and US20040572011P (WO2005116231). Each of these patents and applications is hereby incorporated by reference.

BACKGROUND OF THE INVENTION

The ability to modulate protein activities has long been the hallmark of small molecule drug discovery and development, and the success of this traditional therapeutic approach is unquestioned. However, the number and nature of small molecule drug targets are more limiting than would be ideal and have less target specificity and more off-target side effects that will likely make for significant commercial and regulatory challenges in the years ahead. A newer technology for inhibiting protein activity that has received acceptance is siRNA-mediated gene silencing. The mechanism for siRNA inhibition is post-transcriptional and pre-translational. It has the advantage of being relatively selective for target RNA sequences but, like small molecules, suffers from off-target side effects.

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

Mammalian mitogen-activated protein kinase (MAPK) and extracellular-signal-regulated kinase (ERK) are the same enzyme, herein referred to as ERK. ERK has two isoforms, both of which can phosphorylate serine and threonine residues in protein or peptide substrates. Use of the term ERK herein encompasses both ERK isoforms. Many cellular substrates of ERK have been identified. Furthermore, polypeptides have been used to examine ERK substrate specificity. While polypeptides and variants thereof have been studied as individual substrates or ligands, mixed ligands linked together as polyligands that modulate ERK activity have not been demonstrated before this invention. An aspect of the invention is to provide novel, modular, inhibitors of ERK activity by modifying one or more natural substrates by truncation and/or by amino acid substitution. A further aspect of the invention is the subcellular localization of an ERK inhibitor, ligand, or polyligand by linking to a subcellular localization signal. Examples of ERK substrates and/or regulators include those described in the following references: Adams, et al. 2000 J Neurochem 75:2277-87, Arnaud, et al. 2004 J Immunol 173:3962-71, Chung, et al. 1997 Mol Cell Biol 17:6508-16, Clark-Lewis, et al. 1991 J Biol Chem 266:15180-4, Eymin, et al. 2006 Cell Cycle 5:759-65, Fantz, et al. 2001 J Biol Chem 276:27256-65, Garcia, et al. 2002 Embo J 21:5151-63, Gille, et al. 1995 Embo J 14:951-62, Haycock, et al. 1992 Proc Natl Acad Sci USA 89:2365-9, Hedges, et al. 2000 Am J Physiol Cell Physiol 278:C718-26, Hindley, et al. 2002 J Cell Sci 115:1575-81, Howell, et al. 1991 Mol Cell Biol 11:568-72, Ishibe, et al. 2004 Mol Cell 16:257-67, Jacobs, et al. 1999 Genes Dev 13:163-75, Jacque, et al. 1998 Embo J 17:2607-18, Kelemen, et al. 2002 J Biol Chem 277:8741-8, Kolch 2000 Biochem J 351 Pt 2:289-305, Lefebvre, et al. 2002 J Cell Biol 157:603-13, Lin, et al. 1999 J Biol Chem 274:15971-4, Matallanas, et al. 2006 Mol Cell Biol 26:100-16, Matsuura, et al. 2005 Biochemistry 44:12546-53, Matter, et al. 2002 Nature 420:691-5, Missero, et al. 2000 Mol Cell Biol 20:2783-93, Morton, et al. 2004 FEBS Lett 572:177-83, Pandey, et al. 2005 Mol Cell Biol 25:10695-710, Sanghera, et al. 1990 FEBS Lett 273:223-6, Schaeffer, et al. 1999 Mol Cell Biol 19:2435-44, Songyang, et al. 1996 Mol Cell Biol 16:6486-93, Soond, et al. 2005 J Cell Sci 118:2371-80, Terret, et al. 2003 Development 130:5169-77, Veeranna, et al. 1998 J Neurosci 18:4008-21, Xu, et al. 2001 Mol Cell Biol 21:2981-90, Zhang, et al. 2001 J Biol Chem 276:14572-80, and MAP Kinase Substrate Peptide Catalog #2-125 Lot #23369 (Upstate, Lake Placid, N.Y.).

Design and synthesis of polypeptide ligands that modulate calcium/calmodulin-dependent protein kinase and that localize to the cardiac sarco(endo)plasmic reticulum was performed by Ji et al. (J Biol Chem (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also U.S. Pat. No. 7,071,295.

DETAILED DESCRIPTION OF POLYPEPTIDE AND POLYNUCLEOTIDE SEQUENCES

Specifically, the ERK polyligand of SEQ ID NO: 1 is encoded by SEQ ID NO:2, SEQ ID NO:3, and by SEQ ID NO:4, wherein the codons have been optimized for mammalian expression. SEQ ID NO:3 and SEQ ID NO:4 include different alternatives of predetermined flanking restriction sites. Furthermore, SEQ ID NO:4 utilizes alternative codons for mammalian expression. A vector map of a vector containing SEQ ID NO:4 is shown in FIG. 12 (labeled ERK decoy). SEQ ID NO:1 is an embodiment of a polyligand of the structure A-S1-B-S2-C-S3-D-S4-E-S5-F, wherein A is SEQ ID NO:91, B is SEQ ID NO:97, C is SEQ ID NO:28, D is SEQ ID NO:29, E is SEQ ID NO:30, and F is SEQ ID NO:31, wherein Xaa is alanine, and wherein S1 is a spacer of the amino acid sequence AA, and S2 is a spacer of amino acid sequence AAAA (SEQ ID NO: 109), S3 is a spacer of the amino acid sequence GAGA (SEQ ID NO: 110), S4 is a spacer of the amino acid sequence GGGG (SEQ ID NO: 111), and S5 is a spacer of the amino acid sequence AGAG (SEQ ID NO: 112). A polyligand of structure A-S1-B-S2-C-S3-D-S4-E-S5-F is also called herein a heteropolyligand, shown generically in FIG. 4D.

SEQ ID NO:5 is an embodiment of a polyligand of the structure X-Y-S2-Z-S3-A -S4-B-S6-C-S5-D-S7-E-S8-F, wherein X is SEQ ID NO:32, Y is SEQ ID NO:98, Z is SEQ ID NO:33, A is SEQ ID NO:34, B is SEQ ID NO:35, C is SEQ ID NO:100, D is SEQ ID NO:36, E is SEQ ID NO:37, and F is SEQ ID NO:107, wherein Xaa is alanine, and wherein S2 is a spacer of amino acid sequence AAAA (SEQ ID NO: 1091, S3 is a spacer of the amino acid sequence GAGA (SEQ ID NO: 110), S4 is a spacer of the amino acid sequence GGGG (SEQ ID NO: 111), S6 is a spacer of the amino acid sequence AGPGAEF (SEQ ID NO: 113), S5 is a spacer of the amino acid sequence AGAG (SEQ ID NO: 112), S7 is a spacer of the amino acid sequence AAGG (SEQ ID NO: 114), and S8 is a spacer of the amino acid sequence GGAA (SEQ ID NO: 115). The ERK polyligand of SEQ ID NO:5 is encoded by SEQ ID NO:6, SEQ ID NO:7 and by SEQ ID NO:8, wherein the codons have been optimized for mammalian expression. SEQ ID NO:7 and SEQ ID NO:8 include different alternatives of predetermined flanking restriction sites. Furthermore, SEQ ID NO:8 utilizes alternative codons for mammalian expression. A polyligand of structure X-Y-S2-Z-S3-A-S4-B-S6-C-S5-D-S7-E-S8-F is also called herein a heteropolyligand, shown generically in FIG. 4E.

SEQ ID NOS:9-27 are full length ERK protein substrates. These sequences have the following public database accession numbers: NP004032, NP001871, NP149129, NP001781, O75956, NP005220, NP536739, CAI17445, AAF65618, NP001006666, NP035353, NP062651, Q07666, AAL68976, NP644805, NP003174, Q15648, NP033411, and AAA42258. Each of the sequences represented by these accession numbers is incorporated by reference herein. In SEQ ID NOS:9-27, the positions of the amino acid(s) phosphorylatable by ERK are represented by Xaa. In wild-type proteins, Xaa is serine or threonine. In the ligands of the invention, Xaa is any amino acid.

SEQ ID NOS:28-90 are peptide sequences including subsequences of SEQ ID NOS:9-27, which represent examples of kinase active site blocker peptide ligand sequences where the location of the ERK phosphorylatable serine or threonine in the natural polypeptide is designated as Xaa.

SEQ ID NOS:91-108 are polypeptide inhibitors of ERK (see FIG. 15). Specifically, SEQ ID NOS:91-96 are ERK activation site blockers, and SEQ ID NOS:97-108 are ERK docking site blockers.

SEQ ID NOS:28-108 represent examples of monomeric polypeptide ligand sequences.

Amino acid sequences containing Xaa encompass polypeptides where Xaa is any amino acid.

DETAILED DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1C show examples of homopolymeric ligands without spacers.

FIGS. 2A-2C show examples of homopolymeric ligands with spacers.

FIGS. 3A-3E show examples of heteropolymeric ligands without spacers.

FIGS. 4A-4F show examples of heteropolymeric ligands with spacers. In FIG. 4E, the abbreviation, S, stands for SPACER.

FIGS. 7A-7G show examples of ligands and polymeric ligands linked to an optional localization signal.

FIGS. 8A-8G show examples of ligands and polymeric ligands linked to an optional localization signal and an optional epitope tag.

FIGS. 9A-9G show examples of gene constructs where ligands and polyligands are linked to an optional localization signal, an optional epitope tag, and an optional reporter.

Figure 12:
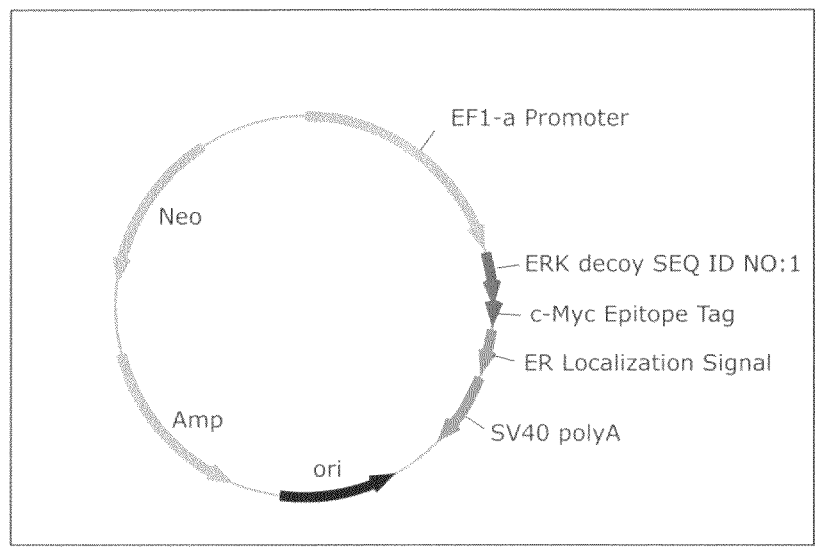
FIG. 12 shows a diagram of a vector for cell transformation.
Figure 13:
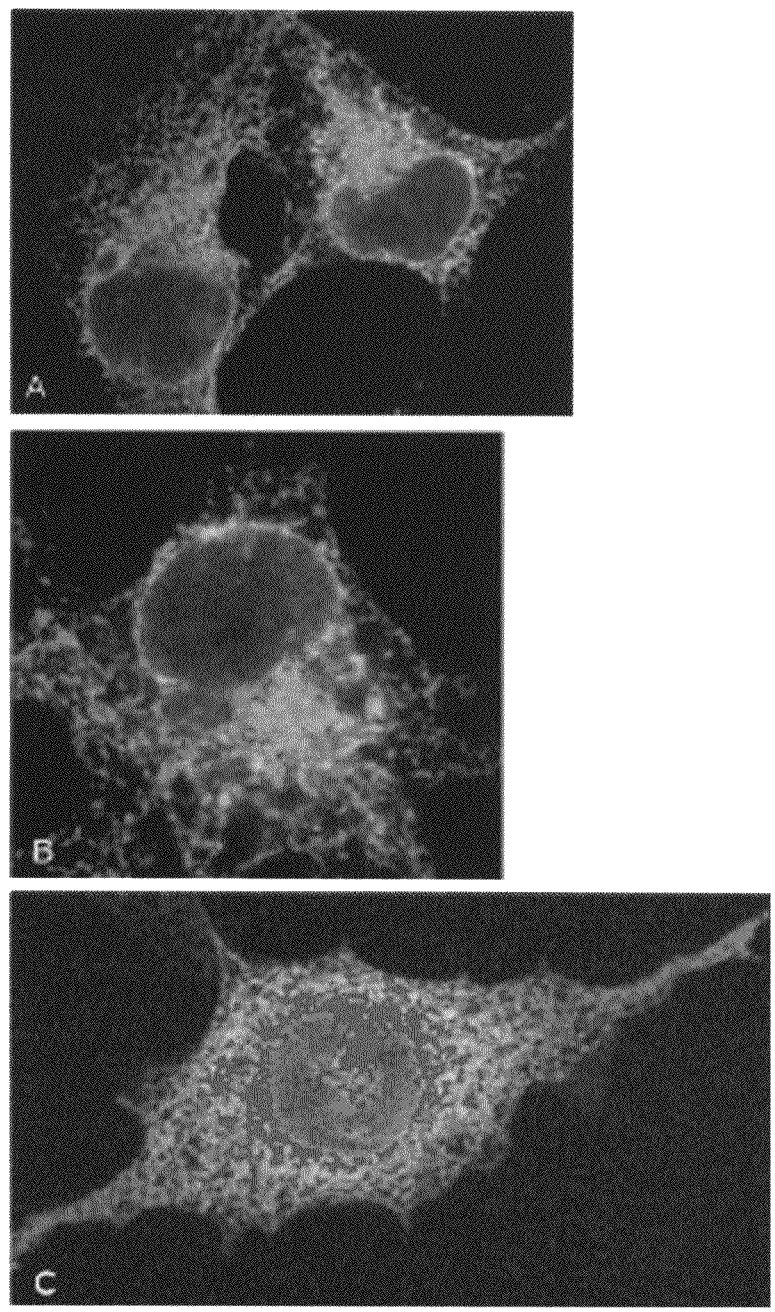

FIG. 13 shows Cos7 cells transformed with the vector depicted in FIG. 12, wherein the vector includes SEQ ID NO:4 which encodes the ERK polyligand of SEQ ID NO:1. This figure demonstrates endoplasmic reticulum (ER) localization of an ERK polyligand: Cos7 cells were transfected with vector containing an ER localization signal, a c-Myc epitope tag, and the ERK polyligand of SEQ ID NO:1 (ERK decoy). Panels A and B depict Cos7 cells transfected with the ERK decoy while Panel C depicts a Cos7 cell transfected with a localization signal control vector lacking an ERK polyligand. The cells in each panel were treated with a stain for the ER-resident protein calreticulin (red) as well as anti-c-Myc antibody staining specific to the c-Myc epitope tag (green). Panels A, B and C show concentrated protein expression to the endoplasmic reticulum as evidenced by the co-localization between both the ERK decoy and localization control with the ER-resident protein calreticulin (yellow).

Figure 14:
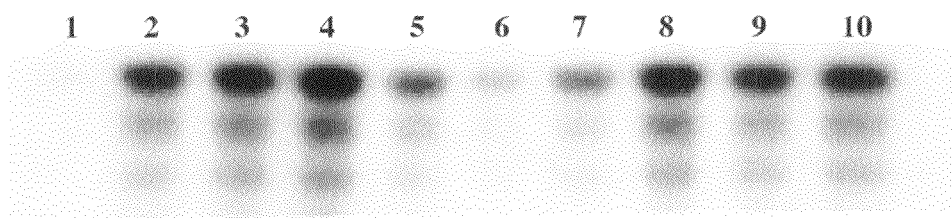

FIG. 14 shows localized inhibition of ERK-mediated myelin basic protein phosphorylation by the ERK polyligand of SEQ ID NO: 1 (decoy). A constitutively-active form of the RasV12 protein, a known activator of MAPK signaling pathways, was used to activate ERK kinase in defined regions of Cos7 cells. Several fusion proteins as described by Matallanas et al. *Mol Cell Biol.* 2006 January; 26(1):100-116 (hereby incorporated by reference), were used to activate ERK kinase in specific subcellular compartments. The constitutively-active RasV12 protein promoted cell-wide activation of ERK. The Lck-RasV12 fusion protein activated ERK-protein associated with lipid rafts in or near the plasma membrane. The M1-RasV12 fusion protein activated ERK in the endoplasmic reticulum. Lane 1: control. Lane 2: ERK activity in cells expressing active Lck-RasV12 fusion protein. Lane 3: ERK activity in cells co-expressing active Lck-RasV12 fusion protein, and ERK decoy protein (ER localization signal, a c-Myc epitope tag, and the ERK polyligand of SEQ ID NO:1). Lane 4: ERK activity in cells co-expressing active Lck-RasV12 fusion protein, and CAT fragment-containing ER localization control protein. Lane 5: ERK activity in cells expressing active M1-RasV12 fusion protein. Lane 6: ERK activity in cells co-expressing active M1-RasV12 fusion protein, and ERK decoy protein. Lane 7: ERK activity in cells co-expressing active M1-RasV12 fusion protein, and CAT fragment-containing ER localization control protein. Lane 8: ERK activity cells expressing active RasV12 protein. Lane 9:

ERK activity in cells co-expressing active RasV12 fusion protein, and ERK decoy protein. Lane 10: ERK activity in cells co-expressing active RasV12 protein, and CAT fragment-containing ER localization control protein. This figure represents compartmentalized ERK activity in the plasma membrane (Lanes 24), in the endoplasmic reticulum (Lanes 5-7), and cell wide (Lanes 8-10) in Cos-7 cells. The bands on the gel represent varying phosphorylation states of ERK substrate, myelin basic protein (MBP); darker bands represent higher levels of ERK activity. When SEQ ID NO:1 was added to cells with ER-active ERK, ERK activity in the endoplasmic reticulum was reduced by approximately 60%. Again, Lane 1 is the control. Lanes 24 show activated ERK at the plasma membrane. Lanes 5-7 show activated ERK in the ER. Lanes 8-10 show activated ERK in the entire cell. Lanes 2, 5, & 8 show normal ERK activity. Lanes 3, 6, & 9 show ERK activity with co-expressed SEQ ID NO:1 fusion protein. Lanes 4, 7, & 10 show ERK activity with co-expressed control.

Figure 15:
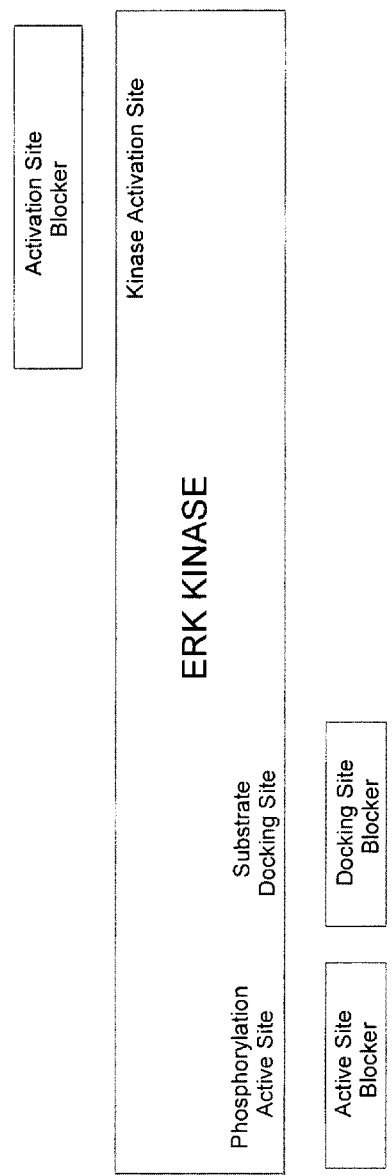

FIG. 15 shows a diagram of the ERK interaction sites of the different categories of ERK monomeric ligands including active site blockers, docking site blockers, and activation site blockers.

Figure 16:

FIG. 16 shows nuclear localization of SEQ ID NO:1 fused to a nuclear localization signal and c-Myc epitope tag. Location was detected by immunostaining for c-Myc (green).

Figure 17:

FIG. 17 shows cytoplasmic localization of SEQ ID NO:1 fused to a nuclear-exclusion localization signal and c-Myc epitope tag. Location was detected by immunostaining for c-Myc (green).

Figure 18:
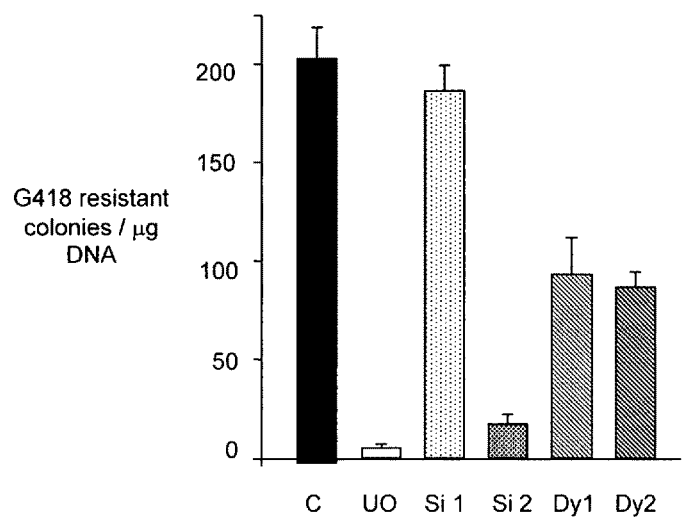

FIG. 18 shows inhibition of cell proliferation using ERK polyligands of SEQ ID NO:1 and SEQ ID NO:5 as compared to siRNA and a small molecule inhibitor. G418-resistant colony formation was assayed in NIH3T3 cells using siRNA specific for ERK1 or ERK2 isoforms; a small molecule inhibitor; and pancellular (no localization signal) polyligands of SEQ ID NO:1 and SEQ ID NO:5. G418-resistant colony formation was assayed in NIH3T3 cells transfected with vector (C) (1 μg) plus: siRNA oligonucleotides for ERK isoform 1 (Si1) or ERK isoform 2 (Si2) (25 ng); or vectors encoding for SEQ ID NO:1 (Dy1) or SEQ ID NO:5 (Dy2) (1 μg); or treated with the MEK inhibitor UO126 (1 μM). Colonies were stained and counted after 15 days in culture.

Figure 19:
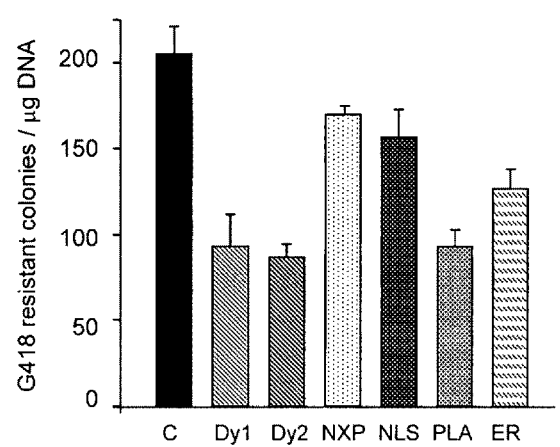

FIG. 19 shows inhibition of cell proliferation using localized ERK polyligand SEQ ID NO:1 fused to different localization signals. G418-resistant colony formation was assayed in NIH3T3 cells using pancellular SEQ ID NO:1 and SEQ ID NO:5, or SEQ ID NO:1 targeted to either the cytoplasm (NXP, nuclear exclusion), nucleus (NLS), plasma membrane (PLA), or endoplasmic reticulum (ER). G418-resistant colony formation was assayed in NIH3T3 cells transfected with vector (C) (1 μg) plus constructs (1 μg each) encoding for SEQ ID NO:1 (Dy1), SEQ ID NO:5, (Dy2) or SEQ ID NO:1 targeted to: cytoplasm (NXP), nucleus (NLS), plasma membrane (PLA), and endoplasmic reticulum (ER). Colonies were stained and counted after 15 days in culture.

Figure 20:
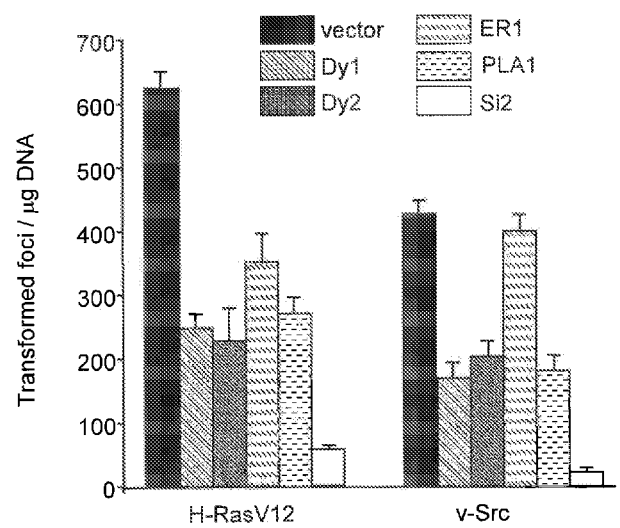

FIG. 20 shows inhibition of cell transformation with pancellular SEQ ID NO:1 (Dy1), pancellular SEQ ID NO:5 (Dy2), and ER-localized SEQ ID NO:1 (ER1), and plasma membrane-localized SEQ ID NO:1 (PLA1) as compared to siRNA against ERK isoform 2 (Si2). Transformed foci formation was assayed in NIH3T3 cells transfected with H-ras V12 or v-Src (0.25 ng) plus constructs (1 μg each).

BRIEF DESCRIPTION OF THE INVENTION

The invention relates to polypeptide ligands and polyligands for ERK. Various embodiments of the ERK ligands and polyligands are represented in SEQ ID NOS:1-108. More specifically, the invention relates to ligands, homopolyligands, and heteropolyligands that comprise any one or more of SEQ ID NOS:28-108. Additionally, the invention relates to ligands and polyligands comprising one or more subsequences of SEQ ID NOS:9-27 or any portion thereof. Furthermore, the invention relates to polyligands with at least about 80%, 85%, 90%, 95%, 96%, 97%, 98% and 99% sequence identity to a polyligand comprising one or more of SEQ ID NOS:28-108 or any portion thereof. Furthermore, the invention relates to polyligands with at least about 80%, 85%, 90%, 95%, 96%, 97%, 98% and 99% sequence identity to a polyligand comprising one or more subsequences of SEQ ID NOS:9-27.

Polyligands, which can be homopolyligands or heteropolyligands, are chimeric ligands composed of two or more monomeric polypeptide ligands. An example of a monomeric ligand is the polypeptide represented by SEQ ID NO:38, wherein Xaa is any amino acid. SEQ ID NO:38 is a selected subsequence of wild-type full length SEQ ID NO:9, wherein the amino acid corresponding to Xaa in the wild-type sequence is a serine or threonine phosphorylatable by ERK. An example of a homopolyligand is a polypeptide comprising a dimer or multimer of SEQ ID NO:38, wherein Xaa is any amino acid. An example of a heteropolyligand is a polypeptide comprising SEQ ID NO:28 and one or more of SEQ ID NOS:29-108, wherein Xaa is any amino acid. There are numerous ways to combine SEQ ID NOS:28-108 into homopolymeric or heteropolymeric ligands. Furthermore, there are numerous ways to combine additional subsequences of SEQ ID NOS:9-27 with each other and with SEQ ID NOS:28-108 to make polymeric ligands.

The polyligands of the invention optionally comprise spacer amino acids before, after, or between monomers. SEQ ID NO:1 is an embodiment of a polyligand of the structure A-S1-B-S2-C-S3-D-S4-E-S5-F, wherein A is SEQ ID NO:91, B is SEQ ID NO:97, C is SEQ ID NO:28, D is SEQ ID NO:29, E is SEQ ID NO:30, and F is SEQ ID NO:31, wherein Xaa is alanine, and wherein S1, S2, S3, S4 and S5 are spacers. This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands.

Monomeric ligands can be categorized into types (FIG. 15). One type of monomeric ligand is a polypeptide where at least a portion of the polypeptide is capable of being recognized by ERK as a substrate or pseudosubstrate (active site blocker). The portion of the polypeptide capable of recognition is termed the recognition motif. In the present invention, recognition motifs can be natural or synthetic. Examples of recognition motifs are well known in the art and include, but are not limited to, naturally occurring ERK substrates and pseudosubstrate motifs (SEQ ID NOS:28-90 and subsequences of SEQ ID NOS:9-27 containing a recognition motif). Another type of monomeric ligand is a polypeptide where at least a portion of the polypeptide is capable of associating with ERK at a substrate or pseudosubstrate docking site (docking site blocker). A docking site type of monomeric ligand prevents ERK substrate phosphorylation by interfering with substrate association and alignment (SEQ ID NOS:97-108). Yet another type of monomeric ligand is a polypeptide where at least a portion of the polypeptide is capable of associating with ERK at ERK's activation site (SEQ ID NOS: 91-96), thereby blocking ERK activation (activation site blocker), thereby preventing ERK from phosphorylating a substrate.

A polymeric ligand comprises two or more monomeric ligands linked together.

A homopolymeric ligand is a polymeric ligand where each of the monomeric ligands is identical in amino acid sequence, except that a phosphorylatable residue may be substituted or modified in one or more of the monomeric ligands.

A heteropolymeric ligand is a polymeric ligand where some of the monomeric ligands do not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclese activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

Terms used in the specification and claims are intended to have meanings consistent with that known in the art. For example, as used herein, G418 is an aminoglycoside antibiotic also known as Geneticin. Resistance to G418 is conferred by the neo gene. HEK293 cells are human embryonic kidney 293 cell line. H-RasV12 is a constitutively active mutant form of Ras. NIH3T3 is a mouse fibroblast cell line. Raf stand for Ras-activated factor. Ras is a small GTPase or G protein. RNA stands for ribonucleic acid. SiRNA stands for small interfering RNA. Transfection is the introduction of foreign material (such as DNA) into eukaryotic cells. Transformation is a process of tumorigenesis whereby normal cells become cancerous and possess phenotypes including but not limited to excessive growth, plasticity, chromosome abnormalities, foci formation, cell cycle abnormalities, among others. V-Src is a tyrosine kinase encoded by the viral oncogene isolated from Rous sarcoma virus.

DETAILED DESCRIPTION OF THE INVENTION

The present invention relates to ligands and polyligands that are ERK modulators. Various embodiments of ligands and polyligands are represented in SEQ ID NOS:1-108. Polyligands are chimeric ligands comprising two or more monomeric polypeptide ligands. An example of a monomeric ligand is the polypeptide represented by SEQ ID NO:43, wherein Xaa is any amino acid. SEQ ID NO:43 is a selected subsequence of wild-type full length SEQ ID NO:11, wherein the amino acid corresponding to Xaa in the wild-type sequence is a serine or threonine phosphorylatable by ERK. Another example of a monomeric ligand is the polypeptide represented by SEQ ID NO:99. Another example of a monomeric ligand is the polypeptide represented by SEQ ID NO:94. Each of SEQ ID NOS:28-108 represents an individual polypeptide ligand in monomeric form, wherein Xaa is any amino acid. SEQ ID NOS:28-90 are selected examples of subsequences of SEQ ID NOS:9-27, however, other subsequences of SEQ ID NOS:9-27 containing a recognition motif may also be utilized as monomeric ligands. Monomeric ligand subsequences of SEQ ID NOS:9-27 may be wild-type subsequences. Additionally, monomeric ligand subsequences of SEQ ID NOS:9-27 may have the ERK phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:28-108. Furthermore, monomeric ligands and polyligands may have at least about 80%, 85%, 90%, 95%, 96%, 97%, 98% and 99% sequence identity to a subsequence of SEQ ID NOS:9-27.

An example of a homopolyligand is a polypeptide comprising a dimer or multimer of SEQ ID NO:86, wherein Xaa is any amino acid. Another example of a homopolyligand is a polypeptide comprising a dimer or multimer of SEQ ID NO:95. Another example of a homopolyligand is a polypeptide comprising a dimer or multimer of SEQ ID NO:106.

An example of a heteropolyligand is a polypeptide comprising SEQ ID NO:108 and one or more of SEQ ID NOS:28-107, wherein Xaa is any amino acid. There are numerous ways to combine SEQ ID NOS:28-108 into homopolymeric or heteropolymeric ligands. Furthermore, there are numerous ways to combine additional subsequences of SEQ ID NOS:9-27 with each other and with SEQ ID NOS:28-108 to make polymeric ligands.

Polyligands may comprise any two or more of SEQ ID NOS:28-108, wherein Xaa is any amino acid. A dimer or multimer of SEQ ID NO:91 is an example of a homopolyligand. An example of a heteropolyligand is a polypeptide comprising SEQ ID NO:28 and one or more of SEQ ID NOS:29-108. There are numerous ways to combine SEQ ID NOS:28-108 into homopolymeric or heteropolymeric ligands. SEQ ID NOS:28-90 are selected examples of subsequences of SEQ ID NOS:9-27, however, additional subsequences, wild-type or mutated, may be utilized to form polyligands. The instant invention is directed to all possible combinations of homopolyligands and heteropolyligands without limitation.

SEQ ID NOS:9-27 show proteins that contain at least one serine or threonine residue phosphorylatable by ERK, the positions of which are represented by Xaa. SEQ ID NOS:28-90 are subsequences of SEQ ID NOS:9-27 where, again, the locations of the ERK phosphorylatable residues are represented by Xaa. In nature, Xaa is, generally speaking, serine or threonine. In one embodiment of the instant invention, Xaa can be any amino acid. Ligands where Xaa is serine or threonine can be used as part of a polyligand, however in one embodiment, at least one phosphorylatable serine or threonine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, or tyrosine. The Xaa may also be a non-naturally occurring amino acid. In another embodiment, the ERK phosphorylatable serine(s) or threonine(s) are replaced by alanine. The ligands and polyligands of the invention are designed to modulate the endogenous effects of one or more isoforms of ERK.

In general, ligand monomers based on natural ERK substrates are built by isolating a putative ERK phosphorylation recognition motif in a ERK substrate. Sometimes it is desirable to modify the phosphorylatable residue to an amino acid other than serine or threonine. Additional monomers include the ERK recognition motif as well as amino acids adjacent and contiguous on either side of the ERK recognition motif. Monomeric ligands may therefore be any length provided the monomer includes the ERK recognition motif. For example, the monomer may comprise an ERK recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises an inhibitor of ERK comprising at least one copy of a peptide selected from the group consisting of:
a) a peptide at least 80% identical to a peptide comprising amino acid residues corresponding to amino acid residues 407-415 of SEQ ID NO:9, wherein the amino acid residue corresponding to amino acid residue 412 of SEQ ID NO:9 is an amino acid residue other than serine or threonine;
b) a peptide at least 80% identical to a peptide comprising amino acid residues corresponding to amino acid residues 403-416 of SEQ ID NO:9, wherein the amino acid residue corresponding to amino acid residue 412 of SEQ ID NO:9 is an amino acid residue other than serine or threonine;
c) a peptide at least 80% identical to a peptide comprising amino acid residues corresponding to amino acid residues 400-417 of SEQ ID NO:9, wherein the amino acid residue corresponding to amino acid residue 412 of SEQ ID NO:9 is an amino acid residue other than serine or threonine; and
d) a peptide at least 80% identical to a peptide comprising amino acid residues corresponding to amino acid residues 399-418 of SEQ ID NO:9, wherein the amino acid residue corresponding to amino acid residue 412 of SEQ ID NO:9 is an amino acid residue other than serine or threonine.

As used herein, the terms "correspond(s) to" and "corresponding to," as they relate to sequence alignment, are intended to mean enumerated positions within a reference protein, e.g., CDC25c (SEQ ID NO:12), and those positions that align with the positions on the reference protein. Thus, when the amino acid sequence of a subject peptide is aligned with the amino acid sequence of a reference peptide, e.g., SEQ ID NO:12, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for ERK, such as substrates identified by SEQ ID NOS: 9-27. Furthermore, if the substrate has more than one recognition motif, then more than one monomer may be identified therein.

Further embodiments of the invention include monomers based on ERK inhibitors, regulators, or binding partners, such as those identified by SEQ ID NOS:91-108 (ERK activation site blockers and ERK substrate docking site blockers) and subsequences thereof.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting ERK in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring ERK recognition motif that has been modified by addition, deletion, or substitution of one or more amino acids in the primary structure (amino acid sequence) of the motif. For example, a modified ERK recognition motif may be a motif where the phosphorylatable amino acid has been modified to a non-phosphorylatable amino acid. The terms "protein" and "polypeptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of amino acids of the query sequence that are N- and C-terminus to the reference sequence that are not matched/aligned, as a percent of the total amino acids of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The polyligands of the invention optionally comprise spacer amino acids before, after, or between monomers. The length and composition of the spacer may vary. An example of a spacer is glycine, alanine, polyglycine, or polyalanine. Specific examples of spacers used between monomers in SEQ ID NO:5 are the four amino acid spacers AAAA (SEQ ID NO:109), GAGA (SEQ ID NO:110), GGGG (SEQ ID NO:111), AGAG (SEQ ID NO:112), AAGG (SEQ ID NO:114). GGAA (SEQ ID NO:115), and the six amino acid spacer AGPGAEF (SEQ ID NO:113). In the instance of SEQ ID NO:5, the proline-containing spacer is intended to break an alpha helical secondary structure. Spacer amino acids may be any amino acid and are not limited to alanine, glycine and proline. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5G, FIGS. 6A-6G, FIGS. 7A-7G, and FIGS. 8A-8G). Non-limiting examples of epitope tags are FLAG™ (Kodak; Rochester, N.Y.), HA (hemagluttinin), c-Myc and His 6. Non-limiting examples of reporters are alkaline phosphatase, galactosidase, peroxidase, luciferase and green fluorescent protein (GFP). Non-limiting examples of cellular localizations are sarcoplamic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide sythesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. However, ligands linked to localization signals have utility as subcellular tools or therapeutics. For example, ligands depicted generically in FIGS. 7A-7G represent ligands with utility as subcellular tools or therapeutics. ERK ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 5A:
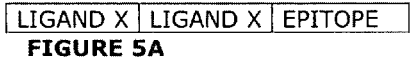
FIGS. 5A-5G show examples of ligands and polymeric ligands linked to an optional epitope tag.
Figure 5B:
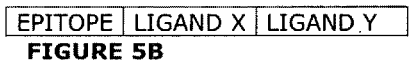
Figure 5C:
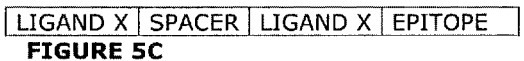
Figure 5D:
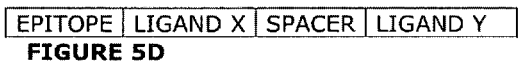
Figure 5E:
Figure 5F:
Figure 5G:
Figure 6A:
FIGS. 6A-6G show examples of ligands and polymeric ligands linked to an optional reporter.
Figure 6B:
Figure 6C:
Figure 6D:
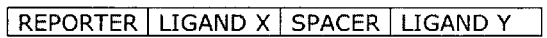
Figure 6E:
Figure 6F:
Figure 6G:
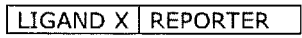
Figure 10A:
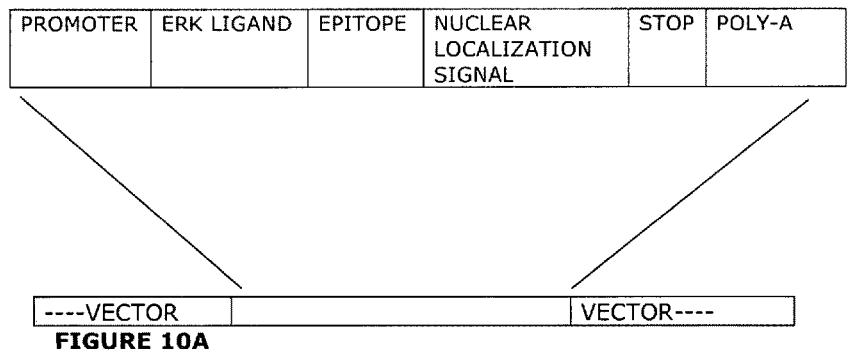
FIGS. 10A-10D show examples of vectors containing ligand gene constructs.
Figure 10B:
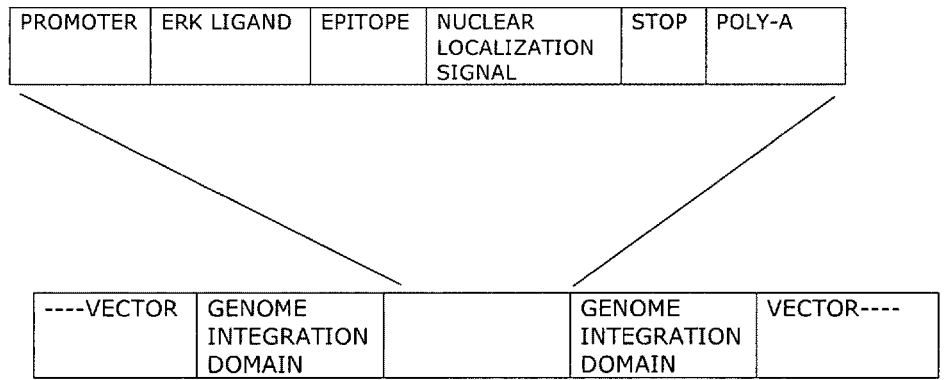
Figure 10C:
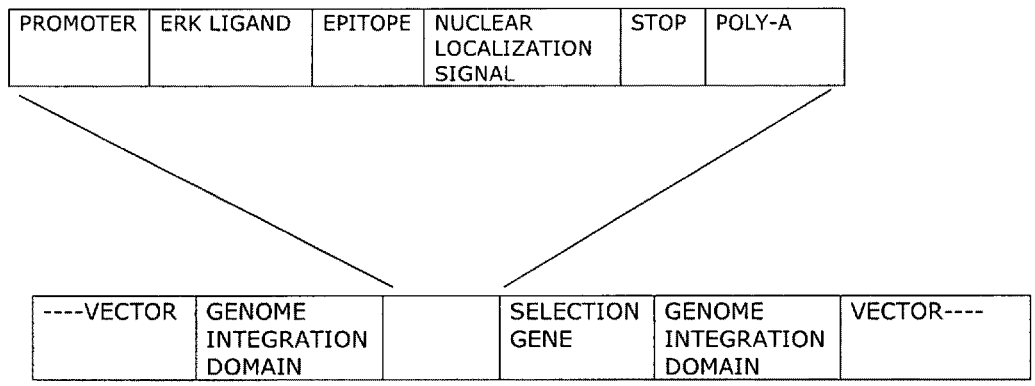

FIG. 10A shows a vector containing an ERK ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the trangene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
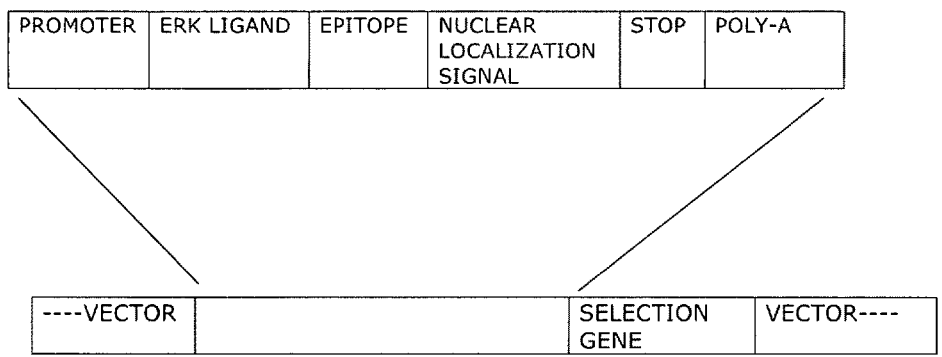

FIG. 10D shows a vector containing an ERK ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclese activity. The flanking sequences optionally provide cloning sites within a vector. The restriction sites can include, but are not limited to, any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealed. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. For example, RHEOSWITCH is an inducible promotor system available from New England Biolabs (Ipswich, Mass.). Temperature sensitive promoters can also be used to increase or decrease gene expression. An embodiment of the invention comprises a ligand or polyligand gene construct whose expression is controlled by an inducible promotor. In one embodiment, the inducible promotor is tetracycline controllable.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular subsequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

Figure 11:
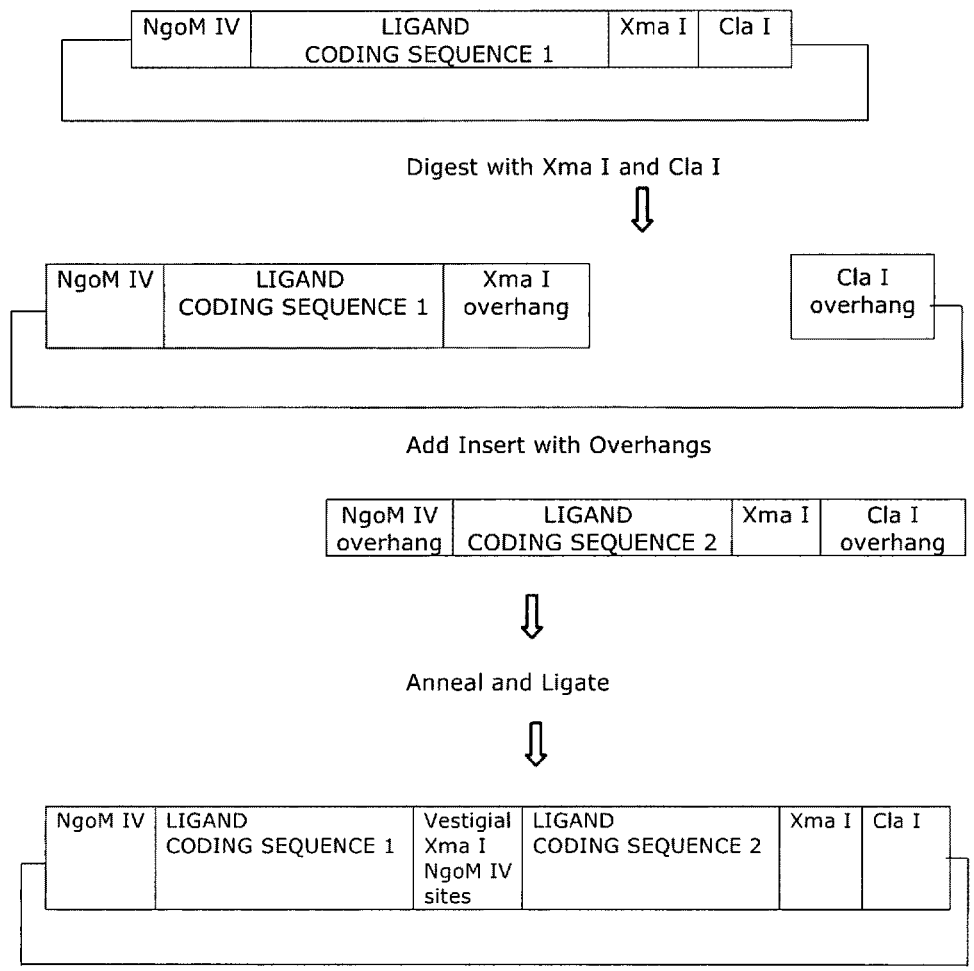
FIG. 11 shows an example of a sequential cloning process useful for combinatorial synthesis of polyligands.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endonuclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate ERK activity are disclosed. Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

Methods

Assays. Ligands of the invention are assayed for kinase modulating activity using one or more of the following methods.

Method 1. A biochemical assay is performed employing commercially-obtained kinase, commercially-obtained substrate, commercially-obtained kinase inhibitor (control), and semi-purified inhibitor ligand of the invention (decoy ligand). Decoy ligands are linked to an epitope tag at one end of the polypeptide for purification and/or immobilization, for example, on a microtiter plate. The tagged decoy ligand is made using an in vitro transcription/translation system such as a reticulocyte lysate system well known in the art. A vector polynucleotide comprising a promotor, such as T7 and/or T3 and/or SP6 promotor, a decoy ligand coding sequence, and an epitope tag coding sequence is employed to synthesize the tagged decoy ligand in an in vitro transcription/translation system. In vitro transcription/translation protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Immunoreagent-containing methods such as western blots, elisas, and immunoprecipitations are performed as described in: Using Antibodies: A Laboratory Manual (Harlow and Lane Cold Spring Harbor Laboratory Press, 1999).

Specifically, tagged decoy ligand synthesized using an in vitro transcription/translation system is semi-purified and added to a microtiter plate containing kinase enzyme and substrate immobilized by an anti-substrate specific antibody. Microtiter plates are rinsed to substantially remove non-immobilized components. Kinase activity is a direct measure of the phosphorylation of substrate by kinase employing a phospho-substrate specific secondary antibody conjugated to horseradish peroxidase (HRP) followed by the addition of 3,3',5,5'-tetramethylbenzidine (TMB) substrate solution. The catalysis of TMB by HRP results in a blue color that changes to yellow upon addition of phosphoric or sulfuric acid with a maximum absorbance at 450 nm. The Control experiments include absence of kinase enzyme, and/or absence of decoy ligand, and/or presence/absence of known kinase inhibitors. A known kinase inhibitor useful in the assay is staurosporine.

Method 2. A similar assay is performed employing the same reagents as above but the substrate is biotinylated and immobilized by binding to a streptavidin-coated plate.

Method 3. A biochemical assay is performed employing commercially-obtained kinase, commercially-obtained substrate, commercially-obtained kinase inhibitor (control), and semi-purified inhibitor ligand of the invention (decoy ligand) in a microtiter plate. A luminescent-based detection system, such as Promega's Kinase-Glo, is then added to inversely measure kinase activity.

Specifically, tagged decoy ligand synthesized using an in vitro transcription/translation system is semi-purified and added to a microtiter plate containing kinase enzyme and substrate. After the kinase assay is performed, luciferase and luciferin are added to the reaction. Luciferase utilizes any remaining ATP not used by the kinase to catalyze luciferin. The luciferase reaction results in the production of light which is inversely related to kinase activity. Control experiments include absence of kinase enzyme, and/or absence of decoy ligand, and/or presence/absence of known kinase inhibitors. A known kinase inhibitor useful in the assay is staurosporine.

Method 4. A similar cell-based assay is performed employing same reagents as above, but synthesizing the decoy ligand in a mammalian cell system instead of an in vitro transcription/translation system. Decoy ligands are linked to an epitope tag at one end of the polypeptide for immobilization and/or for purification and/or for identification in a western blot. Optionally, tagged decoy ligands are also linked to a cellular localization signal for phenotypic comparison of pan-cellular and localized kinase modulation. A vector polynucleotide comprising a constitutive promotor, such as the CMV promotor, a decoy ligand coding sequence, an epitope tag coding sequence, and optionally a localization signal coding sequence is employed to express the decoy ligand in cells. Transfection and expression protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Western Blots and Immunoreagent-containing methods are performed as described in: Using Antibodies: A Laboratory Manual (Harlow and Lane Cold Spring Harbor Laboratory Press, 1999).

EXAMPLES

Example 1

A polypeptide comprising a heteropolyligand, an endoplasmic reticulum cellular localization signal, and a His6 epitope is synthesized. Examples of such polypeptides are generically represented by FIGS. 8A, 8B, 8D, 8E and 8F. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

Example 2

A transgene is constructed using a human cytomegalovirus (CMV) promoter to direct expression of a fusion protein comprising SEQ ID NO:96, SEQ ID NO:99, SEQ ID NO:89, wherein Xaa is alanine (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein (GFP) by confocal microscopy.

Example 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode an ERK ligand, a FLAG™ epitope, and a nuclear localization signal. The ERK ligand is a monomeric ligand, homopolymeric ligand or heteropolymeric ligand as described herein. Nucleotide sequences encoding a FLAG™ epitope are placed downstream of nucleotide sequences encoding the ERK ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

Example 4

Modulation of ERK cellular function by subcellularly localized ERK polyligand is illustrated. A transgene construct containing nucleic acids that encode a polyligand fusion protein, epitope, and endoplasmic reticulum localization signal is made. The expression unit contains nucleotides that encode SEQ ID NO:1 (POLYLIGAND), a c-Myc epitope (EPITOPE), and an endoplasmic reticulum localization signal (LOCALIZATION SIGNAL). This expression unit is subsequently subcloned into a vector between a EF1 alpha promoter and an SV40 polyadenylation signal (depicted in FIG. 12). The completed transgene-containing expression vector is then used to transfect cells. Inhibition of ERK activity is demonstrated by measuring phosphorylation of endogenous substrates against controls (see FIG. 14).

Example 5

Ligand function and localization is demonstrated in vivo by making a transgene construct used to generate mice expressing a ligand fusion protein targeted to the endoplasmic reticulum. The transgene construct is shown generically in FIG. 10B. The expression unit contains nucleotides that encode a tetramer of SEQ ID NO:65, a hemagluttinin epitope, and a nuclear localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 5 harbor the transgene in their genomes.

Test 2: Tissue homogenates are prepared for Western blot analysis. This experiment demonstrates the transgene is expressed in tissues of transgenic mice because hemagluttinin epitope is detected in transgenic homogenates but not in non-transgenic homogenates.

Test 3: Function is assessed by phenotypic observation or analysis against controls.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Results

Results show that the ERK polyligands of the invention (decoys) localized to the appropriate subcellular compartments and inhibited ERK activity at those locations. Localized inhibition caused distinct functional changes in the treated cells, including inhibition of oncogene-induced cell proliferation and transformation. Furthermore, depending on the source of the activation signal for the ERK pathway, the specific subcellular site of inhibition (endoplasmic reticulum or plasma membrane) had a differentiating effect on transformation phenotype of the cells. In contrast, inhibition of ERK by siRNA or a small molecule inhibitor did not reveal this functional difference.

Fluorescence microscopy of the ligand of SEQ ID NO:1 is shown localized to the nucleus (FIG. 16), cytoplasm (FIG. 17), and endoplasmic reticulum (FIG. 13A). The localized ERK ligands were detected by immunostaining for the c-myc epitope tag. FIG. 14 shows ERK activity localized to specific compartments with localized Ras overexpression and SEQ ID NO:1 expressed pancellularly (lanes 8-9) or targeted to the endoplasmic reticulum (lanes 5-7) or plasma membrane (lanes 2-4). The result was location-selective inhibition of ERK activity at the endoplasmic reticulum as measured by phosphorylation of the ERK substrate myelin basic protein (MBP).

Additionally, experiments where inhibition of ERK signaling using ERK ligands of the invention was compared to siRNAs and a small molecule inhibitor. The commercial siRNAs were designed for target specificity to either the ERK1 (sc-29307) or ERK2 (sc-35335) isoforms (Santa Cruz Biotechnology, Inc.). The small molecule inhibitor, UO126 (1,4-diamino-2,3-dicyano-1,4-bis(2-aminophenylthio) butadiene), inhibits ERK signaling through its upstream effector, MEK, and ERK is the only known substrate for MEK. Assays performed were phenotypic assays. The effects of inhibiting ERK activity were measured by looking at functional properties of the cells associated with the MAPK signaling pathway, such as, cell proliferation and transformation. The MAPK signaling cascade in these experiments is initiated by transfection of the cells with a vector containing a constitutively active proto-oncogene, either H-RasV12 or v-Src, which eventually causes the cells to acquire enhanced growth rate (colony formation) and cell transformation rate (foci formation). Inhibition of ERK activity in this cascade will result in reduced rates of proliferation or transformation as measured by numbers of G418-resitant colonies or foci.

Data for colony formation inhibition with the various treatments is presented in FIG. 18. UO126 is very effective at inhibiting the pathway due to its high potency for MEK (~70 nM) and its stability. Furthermore, the siRNAs targeted against ERK1 or ERK2 show isoform specificity as to the effects on proliferation. This is consistent with a recent report that showed interplay between ERK1 and ERK2 in regulating Ras-mediated signaling, wherein ERK2 has a positive role in controlling cell proliferation and ERK1 can affect signal output by counteracting ERK2 activity (Vantaggiato et al. 2006 J. of Biol. 5:14). The two ERK ligands (SEQ ID NO:1 and SEQ ID NO:5, both fused to c-Myc and FLAG tags) used in this experiment are not targeted to a specific subcellular location but are expressed throughout the cell under the control of a constitutive promoter. The ERK ligands, as described herein, are designed with multiple domains (usually mutated substrates) believed capable of competing with the normal endogenous ERK substrates. Thus, unlike siRNAs, which can have RNA sequence specificity for each of the two isoforms of ERK, the ERK decoy ligands may bind to both ERK1 and ERK2 proteins, which may result in only partial inhibition of cell proliferation. Possible reasons for partial inhibition may include a titration effect whereby some of the decoy ligand is "trapped" by ERK1 and unavailable to inhibit ERK2. Partial inhibition may also be due to the inhibition of the ERK1, possibly antagonizing or mitigating the inhibitory effects on ERK2.

Based on the similar effectiveness of SEQ ID NO:1 and SEQ ID NO:5 in inhibiting Ras-mediated cell proliferation, a similar experiment was conducted with SEQ ID NO:1 localized to the nucleus (NLS), the cytoplasm (NXP, nuclear exclusion), the endoplasmic reticulum (ER), and the plasma membrane (PLA). In all cases, location-specific SEQ ID NO:1 causes some inhibition of cell proliferation, with the greatest degree of inhibition arising when the decoy is localized to the plasma membrane (FIG. 19). ER-localized inhibition was also significant, consistent with the results previously reported using dominant negative location-targeted Ras inhibitors (Matallanas et al. (2006) Mol. Cell. Biol. 26: 100-116). SEQ ID NO:1 targeted to the nucleus and cytoplasm gives slight inhibition of proliferation.

Next, the effect of ERK inhibition on cell transformation was investigated using two means of initiating signaling cascades that lead to this biological property (FIG. 20). The first method is the constitutively active Ras mutant used herein above. The second is a constitutively active nonreceptor tyrosine kinase v-Src mutant (pp 60v-src) that also leads to cell transformation, potentially by multiple signaling pathways including the Ras-Raf-MEK-ERK pathway. As shown in FIG. 20, the pancellular decoys (SEQ ID NO:1 and SEQ ID NO:5), ERK2 siRNA, and localized decoy (SEQ ID NO:1 fused to localization signals indicated) all inhibited cell transformation. Treatment of H-RasV12 transformed cells with ER-localized and PLA-localized SEQ ID NO:1 inhibited cell transformation rates by ~50%, similar to results obtained with the pancellularly expressed SEQ ID NO:1 and SEQ ID NO:5. However, when transformation was initiated with v-Src, there was a difference in the inhibition specificity arising from use of SEQ ID NO:1 localized to the ER and PLA. The ER-localized SEQ ID NO:1 caused little to no inhibition relative to the untreated control, while the PLA-localized SEQ ID NO:1 caused ~60% decrease in transformation. That is, ER-localized SEQ ID NO:1 has a significant effect on transformation induced by H-RasV12 but little to no effect when transformation is induced by v-Src. In contrast, inhibition of ERK by siRNA was identical for both the H-Ras and v-Src pathways. Thus, siRNA does not differentiate the effects on transformation induced by distinct oncogenes H-Ras and v-Src.

Disclosed are ligands and polyligands that modulate ERK activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

What is claimed is:

1. An isolated polypeptide heteropolyligand comprising an amino acid sequence at least 80% identical to the amino acid sequence of SEQ ID NO:1, wherein the heteropolyligand inhibits the kinase activity of extracellular-signal-regulated kinase (ERK).

2. The isolated polypeptide heteropolyligand of claim 1 further comprising one or more of: a localization signal, an epitope tag, or a reporter.

3. The isolated polypeptide heteropolyligand of claim 1, comprising an amino acid sequence at least 85% identical to the amino acid sequence of SEQ ID NO:1.

4. The isolated polypeptide heteropolyligand of claim 1, comprising an amino acid sequence at least 90% identical to the amino acid sequence of SEQ ID NO:1.

5. The isolated polypeptide heteropolyligand of claim 1, comprising an amino acid sequence at least 95% identical to the amino acid sequence of SEQ ID NO:1.

6. The isolated polypeptide heteropolyligand of claim 1, comprising an amino acid sequence at least 96% identical to the amino acid sequence of SEQ ID NO:1.

7. The isolated polypeptide heteropolyligand of claim 1, comprising an amino acid sequence at least 97% identical to the amino acid sequence of SEQ ID NO:1.

8. The isolated polypeptide heteropolyligand of claim 1, comprising an amino acid sequence at least 98% identical to the amino acid sequence of SEQ ID NO:1.

9. The isolated polypeptide heteropolyligand of claim 1, comprising an amino acid sequence at least 99% identical to the amino acid sequence of SEQ ID NO:1.

10. The isolated polypeptide heteropolyligand of claim 1, comprising the amino acid sequence of SEQ ID NO:1.

* * * * *

UNITED STATES PATENT AND TRADEMARK OFFICE
CERTIFICATE OF CORRECTION

| | | |
|---|---|---|
| PATENT NO. | : 8,283,445 B2 | Page 1 of 1 |
| APPLICATION NO. | : 11/983235 | |
| DATED | : October 9, 2012 | |
| INVENTOR(S) | : Reed | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 922 days.

Signed and Sealed this
Second Day of September, 2014

Michelle K. Lee
*Deputy Director of the United States Patent and Trademark Office*